United States Patent [19]

Ashton et al.

[11] Patent Number: 5,538,991
[45] Date of Patent: Jul. 23, 1996

[54] ENDOTHELIN ANTAGONISTS BEARING 5-MEMBERED HETEROCYCLIC AMIDES

[75] Inventors: Wallace T. Ashton, Clark; Linda L. Chang, Wayne; William J. Greenlee, Teaneck, all of N.J.

[73] Assignee: Merck & Co., Inc., Rahway, N.J.

[21] Appl. No.: 306,275

[22] Filed: Sep. 14, 1994

[51] Int. Cl.$^6$ .................. C07D 417/12; A61K 31/41
[52] U.S. Cl. .................. 514/397; 514/363; 514/370; 514/377; 514/383; 548/133; 548/139; 548/185; 548/195; 548/214; 548/233; 548/265.4; 548/256; 548/311.7; 548/364.4; 548/526; 549/60; 549/435
[58] Field of Search .................. 548/185, 195, 548/214, 133, 134, 233, 526, 364.4, 311.7, 256, 265.4; 549/60, 435; 514/363, 370, 377, 383, 397

[56] References Cited

U.S. PATENT DOCUMENTS

| | | |
|---|---|---|
| 3,499,008 | 3/1970 | Talet et al. |
| 4,748,272 | 5/1988 | Youssefyeh |
| 5,082,838 | 1/1992 | Naka et al. |
| 5,114,918 | 5/1992 | Ishikawa et al. |
| 5,187,195 | 2/1993 | Oohata et al. |

FOREIGN PATENT DOCUMENTS

| | | |
|---|---|---|
| 436189A1 | 7/1990 | European Pat. Off. |
| 405421A2 | 1/1991 | European Pat. Off. |
| 457195A2 | 11/1991 | European Pat. Off. |
| 460679A2 | 12/1991 | European Pat. Off. |
| 496452A1 | 7/1992 | European Pat. Off. |
| 510526A1 | 10/1992 | European Pat. Off. |
| 526642A1 | 2/1993 | European Pat. Off. |
| 526708A1 | 2/1993 | European Pat. Off. |
| 528312A2 | 2/1993 | European Pat. Off. |
| 534539A1 | 3/1993 | European Pat. Off. |
| 543425A1 | 5/1993 | European Pat. Off. |
| 547317A1 | 6/1993 | European Pat. Off. |
| 558258A1 | 9/1993 | European Pat. Off. |
| 562599A1 | 9/1993 | European Pat. Off. |
| 569193A1 | 11/1993 | European Pat. Off. |
| 601386A1 | 6/1994 | European Pat. Off. |
| 617001 | 9/1994 | European Pat. Off. |
| 06122625 | 6/1994 | Japan. |
| 88450 | 1/1986 | Romania. |
| 2259540 | 3/1993 | United Kingdom. |
| WO9200952 | 1/1992 | WIPO. |
| WO9312991 | 6/1992 | WIPO. |
| WO92/15321 | 9/1992 | WIPO. |
| WO92/20706 | 11/1992 | WIPO. |
| WO9310144 | 5/1993 | WIPO. |
| WO9308799 | 5/1993 | WIPO. |
| WO9313052 | 7/1993 | WIPO. |
| WO9313069 | 7/1993 | WIPO. |
| WO9323404 | 11/1993 | WIPO. |
| WO9414796 | 12/1993 | WIPO. |
| WO9402474 | 2/1994 | WIPO. |
| WO9414434 | 7/1994 | WIPO. |
| WO9421590 | 9/1994 | WIPO. |

OTHER PUBLICATIONS

J. Med. Chem, vol. 35, No. 9, pp. 1493–1508 (1992), by Doherty.
Chem. Pharm. Bulletin, vol. 31, No. 9, pp. 3039–3055 (1983), by Ishii, et al.
"Antihypertensive Effects of the Endothelin Receptor Antagonist BQ–123 in Conscious Spontaneously Hypetensive Rats" E. H. Ohlstein, et al. Journal of Cardiovascular Pharmacology, vol. 22, (Suppl. 8), 1993, pp. S321–S324.
"Direct and Sympathetically Mediated Vasoconstriction in Essential Hypertension" W. G. Haynes, et al. J. Clin. Invest., vol. 94, Oct. 1994, pp. 1359–1364.
"Role of Endothelin in Hypertension" B. K. Krämer, et al. Clin. Investig., vol. 72, (1994), pp. 88–93.
"Potential Role of Endothelin in Hypertension" T. F. Lüscher, et al. Hypertension, vol. 21, No. 6, Part 1, Jun. 1993, pp. 752–757.
"BQ123, An ET(A) Receptor Antagonist, Attenuates Hypoxic Pulmonary–Hypertension in Rats" Bonvallet, S. T., et al. American Journal of Physiology, 266, No. 4, (Apr. 1994), pp. H1327–1331.
"Endothelin—A Receptor Antagonist Prevents Acute Hypoxia–Induced Pulmonary–Hypertension in the Rat" Oparil, S., et al. American Journal of Physiology—Lung Cellular and Molecular Physiology, vol. 12., No. 1, (Jan. 1995), pp. L95–L100.
"Protection from Pulmonary Hypertension with an Orally Active Endothelin Receptor Antagonist in Hypoxic Rats" American Journal of Physiology—Heart and Circulatory Physiology, vol. 37, No. 2, (Feb. 1995), pp. H828–H835.

(List continued on next page.)

Primary Examiner—Robert Gerstl
Attorney, Agent, or Firm—Valerie J. Camara; Mark R. Daniel

[57] ABSTRACT

Phenoxyphenylacetic acids and derivatives of the general structural formula I

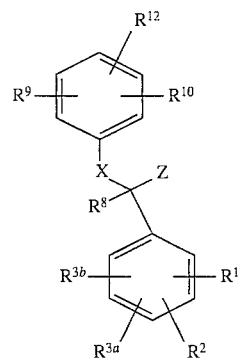

have endothelin antagonist activity and are useful in treating cardiovascular disorders, such as hypertension, postischemic renal failure, vasospasm, cerebral and cardiac ischemia, myocardial infarction, endotoxic shock, benign prostatic hyperplasia, inflammatory diseases including Raynaud's disease and asthma.

22 Claims, No Drawings

OTHER PUBLICATIONS

Endothelial Dysfunction and Remodeling of the Pulmonary Ciculation in Chronic Hypoxic Pulmonary–Hypertension" Dinhxuan, A. T., et al. ACP–Applied Cardiopulmonary Pathophysiology, vol. 5, No. 2, (1994), pp. 93–99.

"Cyclosporine–Induced Elevation in Circulating Endothelin–1 in Patients with Solid–Organ Transplants" Grieff, M., et al. Transplantation vol. 54, No. 4, (Oct. 1993), pp. 880–884.

Cyclosporine–Induced Hypertension After Transplantation" Textor, CS. C., et al. Mayo Clinical Proceedings, vol. 69, (1994), pp. 1182–1193.

"A Role for Endogenous Endothelin–1 in Neointimal Formation After Rat Carotid Artery Balloon Angioplasty" Douglas S. A., et al. Circulation Research, vol. 75, (1994), pp. 190–197.

[125I]–Endothelin–1 Binding to Vasa Vasorum and Regions of Neovascularization in Human and Porcine Blood Vessels: A Possible Role for Endothelin in Intimal Hyperplasia and Atheroscelerosis "Dashwood, M. R., et al. Journal of Cardiovascular Pharmacology", vol. 22, (Suppl. 8), (1993), pp. S343–347.

"The Endothelin–1 Receptor Antagonist BQ–123 Reduces Infarct Size in a a Canine Model of Coronary Occlusion and Reperfusion" Grover, G. J., et al. Cardiovascular Research, vol. 75, No. 9, (Sep. 1993), pp. 1613–1618.

"The Effects of the Endothelin ETa Receptor Antagonist, FR139317, on Infarct Size in a Rabbit Model of Acute Myocardial Ischemia and Reperfusion" McMurdo, L., et al. British Journal of Pharmacology, (1994), vol. 112, pp. 75–80.

"Pharmacology of a Nonselective ET(A) and ET(B) Receptor Antagonist, TAK–044 and the Inhibition of Myocardial Infarct Size in Rats", Watanabe, T., et al. British Journal of Pharmacology, vol. 114, No. 5 (Mar. 1995), pp. 949–954.

"Vasodilator Effects of the Endothelin–1 Receptor Antagonist Bosentan in Patients with Severe Chronic Heart Failure" Kiowski, W., et al. Journal Am. College of Cardiology, Feb. 1995, pp. 296A, abstract No. 779–1.

"Nonpeptide Endothelin Receptor Antagonists. III. Effect of SB 209670 and BQ123 on Acute Renal Failure in Anesthetized Dogs" Brooks, D. P., et al. Journal of Pharmacology and Experimental Therapeutics, vol. 271, (1994), pp. 769–775.

"Reversal of Postischemic Acute Renal Failure with a Selective Endothelin$_A$ Receptor Antagonist in the Rat" Gellai, M., et al. Journal of Clinical Investigator, vol. 93, (1994), pp. 900–906.

"Effects of BQ–123 on Renal–Function and Acute Cyclosporine Induced Renal Dysfunction", Kivlighn, S. D., et al. Kidney International, vol. 45, No. 1, (Jan. 1994), pp. 131–136.

"Endotoxin–Mediated Changes In Plasma Endothelin Concentrations, Renal Endothelin Receptor And Renal–Function", Nambi, P. et al., vol. 48, No. 3, (Mar. 1994), pp. 147–156.

"Effect of Total–Body Cold–Exposure on Plasma–Concentrations of Vonwillebrand–Factor, Endothelin–1 and Thrombomodulin in Systemic Lupus–Erythematosus Patients with or without Raynauds–Phenomenon", Matsuda, J., et al. Acta Haematologica, vol. 88, No. 4, (1992), pp. 189–193.

"Localization of Endothelin–1 and Its Binding–Sites in Scleroderma Skin" Vancheeswaran, R., et al. Journal of Rheumatology, vol. 21, No. 7, (Jul. 1994), pp. 1268–1276.

"Increased Endothelin–1 Production in Fibroblasts Derived from Patients with Systemic–Sclerosis" Kawaguchi, Y., et al. Annals of the Rheumatic Diseases, vol. 53, No. 8, (Aug. 1994), pp. 506–510.

"Characterization of Endothelin–Binding Sites in Human Skin and Their Regulation in Primary Raynauds–Phenomenon and Systemic–Sclerosis" Knock G. A., et al. Journal of Investigative Dermatology, vol. 101, No. 1, (Jul. 1993), pp. 73–78.

"Raynaud Phenomenon" Coffman, J. D., et al. Current Opinion in Cardiology, vol. 8, No. 5, (Sep. 1993), pp. 821–828.

"Parameters of Vascular Function in Idiopathic and Silica–Induced Systemic–Sclerosis" Haustein, U. F. et al. Hautarzt, vol. 44, No. 11, (Nov. 1993), pp. 717–722.

"Circulating Endothelin–1 Levels in Systemic–Sclerosis Subsets—A Marker of Fibrosis or Vascular Dysfunction" Vancheeswaran, R., et al. Journal of Rheumatology, vol. 21, No. 10, (Oct. 1994). pp. 1838–1844.

"Endothelin and Collagen Vascular Disease: A Review with Special Reference to Raynauds–Phenomenon and Systemic––Sclerosis" Yamane, K. Internal Medicine, vol. 33, No. 10, (Oct. 1994), pp. 570–582.

"A Pathogenic Role for Endothelin in Raynauds–Phenomenon" Bottomley, W., et al. Acta Dermato–Venereologica, vol. 74, No. 6, (Nov. 1994), pp. 433–434.

BQ 123, A Peptidic Endothelin ETA Receptor Antagonist, Prevents the Early Cerebral Vasospasm Following Subarachnoid Hemorrage After Interacisternal but not Intravenous–Injection" Clozel, M., et al. Life Sciences, vol. 52, No. 9, (1993), pp. 825–834.

"An Endothelin ET(A) Receptor Antagonist, FR139317, Ameliorates Cerebral Vasospasm in Dogs" Nirei, H., et al. Life Sciences, vol. 52, No. 23, (1993), pp. 1869–1874.

"Reversal of Subarachnoid Hemorrhage–Induced Vasoconstriction with an Endothelin Receptor Antagonist" Foley, P. L. et al. Neurosurgery, vol. 34, No. 1, (Jan. 1994), pp. 108–113.

"Endothelin Levels Increase in Rat Focal and Flobal–Ischemia" Barone, F. C. et al. Journal of Cerebral Blood Flow and Metabolism, vol. 14, No. 2, (Mar. 1994), pp. 337–342.

"Endothelin ET(A) and ET(B) Receptors in Subarachnoid Hemorrhage–Induced Cerebral Vasospasm" Zuccarello, M., et al. European Journal of Pharmacology, vol. 259, No. 1, (Jun. 23, 1994), pp. R1–2.

"Changes of Endothelin Concentration in Cerebrospinal–Fluid and Plasma of Patients with Aneurysmal Subarachnoid Hemorrhage" Shirakami, G., et al. Acta Anaesthesiologica Scandinavica, vol. 38, No. 5, (Jul. 1994), pp. 457–461.

"Prevention of Delayed Vasospasm by an Endothelin ET(A) Receptor Antagonist, BQ–123—Change of ET(A) Receptor Messenger–RNA Expression in a Canine Subarachnoid Hemorrhage Model" Itoh, S., et al. Journal of Neurosurgery, vol. 81, No. 5, (Nov. 1994), pp. 759–764.

"Endothelin Concentrations in Patients with Aneurysmal Subarachnoid Hemorrhage—Correlation with Cerebral Vasospasm, Delayed Ischemic Neurological Deficits, and Volume of Hematoma" Seifert V., et al. Journal of Neurosurgery, vol. 82, No. 1, (Jan. 1995), pp. 55–62.

ENDOTHELIN ANTAGONISTS BEARING 5-MEMBERED HETEROCYCLIC AMIDES

BACKGROUND OF THE INVENTION

Endothelin is a 21-amino acid peptide produced by endothelial cells. The peptide is secreted not only by endothelial cells but also by tracheal epithelial cells or from kidney cells. Endothelin (ET-1) has a potent vasoconstrictor effect. The vasoconstricting effect is caused by the binding of endothelin to its receptor on the vascular smooth muscle cells. [Nature, 332, 411–415 (1988); FEBS Letters, 231, 440–444 (1988); Biochem. Biophys. Res. Commun. 154, 868–875 (1988).]

Endothelin-1 (ET-1) is one of three recently identified potent vasoconstricting peptides which also includes endothelin-2 (ET-2) and endothelin-3 (ET-3) whose sequences differ from ET-1 by two and six amino acids, respectively. [TiPS, 13, 103–108, March 1992.]

Increased levels of endothelin are found in the blood of patients with essential hypertension, acute myocardial infarction, pulmonary hypertension, Raynaud's disease or atherosclerosis or in the washing fluids of the respiratory tract of patients with asthma compared to normal levels. [Japan J. Hypertension 12, 79 (1989); J. Vascular Medicine Biology, 2, 207 (1990); J. Am. Med. Association, 264, 2868 (1990); and The Lancet, ii, 207 (1990) and The Lancet, ii, 747–748 (1989).]

An experimental model of cerebral vasospasm and a second model of acute renal failure have led to the conclusion that endothelin is one of the mediators causing cerebral vasospasm following a subarachnoid hemorrhage, and renal failure. [Japan. Soc. Cereb. Blood Flow & Metabol. 1, 73 (1989); and J. Clin. Invest., 83, 1762–1767 (1989).]

Endothelin was also found to control the release of many physiological substances such as renin, atrial natriuretic peptide, endothelium-derived relaxing factor (EDRF), thromboxane $A_2$, prostacyclin, norepinephrine, angiotensin II and substance P. [Biochem. Biophys. Res. Comm. 157, 1164–1168 (1988); Biochem. Biophys. Res. Comm. 155, 167–172 (1989); Proc. Natl. Acad. Sci. USA, 85, 9797–9800 (1989); J. Cardiovasc. Pharmacol., 13,589–592 (1989); Japan. J. Hypertension 12, 76 (1989); and Neuroscience Letters, 102, 179–184 (1989).] Further, endothelin causes contraction of the smooth muscle of the gastrointestinal tract and the uterine smooth muscle. [FEBS Letters, 247, 337–340 (1989); Eur. J. Pharmacol. 154, 227–228 (1988); Biochem. Biophys. Res. Commun., 159, 317–323 (1989).] Endothelin has also been shown to promote the growth of rat vascular smooth muscle cells which would suggest a possible relevance to arterial hypertrophy. [Atherosclerosis, 78, 225–228 (1989).]

Endothelin receptors are present in high concentration in the peripheral tissues and also in the central nervous system, and cerebral administration of endothelin has been shown to induce behavioral changes in animals, suggesting that endothelin may play an important role in controlling neural functions. [Neuroscience Letters, 97, 276–279 (1989).]

Endotoxin has been shown to promote the release of endothelin. This finding has suggested that endothelin is an important mediator for endotoxin-induced diseases. [Biochem. Biophys. Res. Commun. 161, 1220–1227 (1989); and Acta. Physiol. Scand., 137, 317–318 (1989).]

A study has shown that cyclosporin added to a renal cell culture, increased endothelin secretion. [Eur. J. Pharmacol., 180, 191–192 (1990).] Another study has shown that administration of cyclosporin to rats, led to a decrease in the glomerular filtration rate and an increase in the blood pressure, in association with a remarkable increase in the circulating endothelin level. This cyclosporin-induced renal failure can be suppressed by the administration of anti-endothelin antibody. [Kidney Int. 37, 1487–1491 (1990).] These studies suggest that endothelin is significantly involved in the pathogenesis of cyclosporin-induced renal disease.

A recent study in patients with congestive heart failure demonstrated a good correlation between the elevated levels of endothelin in the plasma and the severity of the disease. [Mayo Clinic Proc., 67, 719–724 (1992).]

Endothelin is an endogenous substance which directly or indirectly (through the controlled release of various other endogenous substances) induces sustained contraction of vascular or non-vascular smooth muscles. Its excess production or excess secretion is believed to be one of the factors responsible for hypertension, pulmonary hypertension, Raynaud's disease, bronchial asthma, acute renal failure, myocardial infarction, angina pectoris, arteriosclerosis, cerebral vasospasm and cerebral infarction. See A. M. Doherty, *Endothelin: A New Challenge*, J. Med. Chem., 35, 1493–1508 (1992).

Substances which specifically inhibit the binding of endothelin to its receptor are believed to block the physiological effects of endothelin and are useful in treating patients with endothelin related disorders.

The novel compounds of the present invention are useful as a non-peptidic endothelin antagonists, and have not been disclosed in any issued patents or published patent applications. Among the published patent applications disclosing linear and cyclic peptidic compounds as endothelin antagonists are the following: Fujisawa in European Patent Application EP-457,195 and Patent Cooperation Treaty (PCT) International Application No. WO 93/10144, Banyu in EP-436,189 and 460,679, Immunopharmaceutics Inc. in WO 93/225580, Warner Lambert Co. WO 92/20706 and Takeda Chemical Ind. in EP-528,312, EP-543,425, EP-547, 317 and WO 91/13089.

Fujisawa has also disclosed two nonpeptidic endothelin antagonist compounds: anthraquinone derivatives produced by a fermentation process using Streptomyces sp. No. 89009 in EP-405,421 and U.S. Pat. No. 5,187,195; and a 4-phenoxyphenol derivative produced by a fermentation process using *Penicillium citreonigrum* F-12880 in a UK Patent Application GB 2259450. Shionogi and Co. has also disclosed nonpeptidic endothelin antagonist triterpene compounds which were produced by a fermentation process using *Myrica cerifera* in WO 92/12991.

Among the non-peptidic endothelin antagonist compounds which are known in the patent literature are: 1) a series of substituted (1,4-quinolinoxy)methylbiphenylcarboxylic acids disclosed by Roussel-Uclaf in EP-498,723; 2) a series of of N-(4-pyrimidinyl)benzenesulfonamides with different substitution patterns from Hoffmann-La Roche published in EP-510,526, EP-526,708 and EP-601,386; 3) a series of naphthalenesulfonamides and benzenesulfonamides disclosed by E. R. Squibb & Sons in EP-558,258 and EP-569,193, respectively; 4) a series of compounds represented by 3-(3-indolylmethyl)-1,4-diaza-2,5-dioxobicyclo [4.3.0]nonane-9-carboxylic acid from Immunopharmaceutics Inc. in WO 93/23404; 5) a series of fused [1,2,4] thiadiazole substituted with an iminosulfonyl substituent from Takeda Chemical Ind. has been disclosed in EP-562, 599; and 6) a series of indane and indene derivatives and 3-substd. indole or indoline from Smith-Kline Beecham Corp. disclosed in WO 93/08779 and WO 94/14434, respectively.

SUMMARY OF THE INVENTION

This invention is concerned with non-peptidic endothelin receptor antagonists represented by the compound of Formula I, pharmaceutical compositions containing these compounds, as well as combination therapies which include a compound of the present invention. The compounds of the present invention are therapeutic agents particularly useful for the treatment of asthma, hypertension, pulmonary hypertension, arteriosclerosis, congestive heart failure, renal failure, particularly post-ischemic renal failure, cyclosporin nephrotoxicity, vasospasm, vascular restenosis, cerebral and cardiac ischemia and other ischemic states, myocardial infarction, Raynaud's disease, benign prostatic hyperplasia, inflammatory bowel diseases, including Crohn's disease and ulcerative colitis, as well as other inflammatory diseases, or endotoxic shock caused by or associated with endothelin.

This invention further constitutes a method for antagonizing endothelin receptors in a mammal, including humans, which comprises administering to a mammal in need of such treatment an effective amount of a compound of Formula I.

DETAILED DESCRIPTION OF THE INVENTION

This invention is concerned with novel compounds of structural formula I:

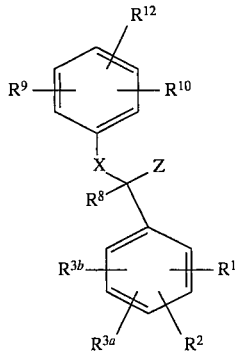

or a pharmaceutically acceptable salt thereof, wherein:

$R^1$, $R^2$, $R^{3a}$ and $R^{3b}$ are independently:
(a) H,
(b) F, Cl, Br, or I,
(c) —$NO_2$,
(d) —$NH_2$,
(e) —NH($C_1$–$C_4$)-alkyl,
(f) —N[($C_1$–$C_4$)-alkyl]$_2$,
(g) —$SO_2NHR^7$,
(h) —$CF_3$,
(i) ($C_1$–$C_6$)-alkyl,
(j) —$OR^7$,
(k) —S(O)$_n$—($C_1$–$C_4$)-alkyl,
(l) —NHCO—($C_1$–$C_4$)-alkyl,
(m) —NHCO—O($C_1$–$C_4$)-alkyl,
(n) —$CH_{10}$—($C_1$–$C_4$)-alkyl,
(o) —O—($CH_2$)$_m$—$OR^7$,
(p) —$CONR^7R^{11}$,
(q) —$COOR^7$, or
(r) -phenyl;

$R^1$ and $R^2$ on adjacent carbon atoms can be joined together to form a ring structure:

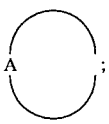

A represents:
a) —Y—C($R^4$)=C($R^5$)—,
b) —Y—C($R^4$)=N—,
c) —Y—N=C($R^4$)—,
d) —Y—[C($R^6$)($R^6$)]$_s$—Y—,
e) —Y—C($R^6$)($R^6$)—C($R^6$)($R^6$)—,
f) —C($R^4$)=C($R^5$)—Y—,
g) —N=C($R^4$)—Y—,
h) —C($R^6$)($R^6$)—C($R^6$)($R^6$)—Y—, or
i) —C($R^4$)=C($R^5$)—C($R^4$)=C($R^5$)—;

n is 0, 1 or 2;

m is 2, 3 or 4;

s is 1 or 2;

Y is —O—, —S(O)$_n$— and $NR^7$;

$R^4$ and $R^5$ are independently:
(a) H,
(b) ($C_1$–$C_6$)-alkyl or ($C_2$–$C_6$)-alkenyl each of which is unsubstituted or substituted with one or two substituents selected from the group consisting of:
  i) —OH,
  ii) —O—($C_1$–$C_4$)-alkyl,
  iii) —S(O)$_n$—($C_1$–$C_4$)-alkyl,
  iv) —$NR^7$—($C_1$–$C_4$)-alkyl,
  v) —$NHR^7$,
  vi) —$COOR^7$,
  vii) —$CONHR^7$,
  viii) —$OCOR^{11}$, or
  ix) —$CONR^7R^{11}$,
(c) ($C_3$–$C_7$)-cycloalkyl,
(d) F, Cl, Br, I,
(e) $CF_3$,
(f) —$COOR^7$,
(g) —$CONR^7R^{11}$,
(h) —$NR^7R^{11}$,
(i) —$NR^7CONR^7R^{11}$,
(j) —$NR^7COOR^{11}$,
(k) —$SO_2NR^7R^{11}$,
(l) —O—($C_1$–$C_4$)-alkyl,
(m) —S(O)$_n$—($C_1$–$C_4$)-alkyl, or
(n) —$NHSO_2R^{11}$;

$R^6$ is:
(a) H,
(b) ($C_1$–$C_4$)-alkyl unsubstituted or substituted with one of the following substituents:
  i) —OH,
  ii) —$NR^7R^{11}$,
  iii) —$COOR^7$,
  iv) —$CONHR^7$, or
  v) —$CONR^7R^{11}$, or
(c) Cl, or F;

$R^7$ is:
(a) H,
(b) ($C_1$–$C_6$)-alkyl,
(c) phenyl,
(d) ($C_1$–$C_6$)-alkylphenyl, or
(e) ($C_3$–$C_7$)-cycloalkyl;

$R^8$ is:
(a) H, (b) $(C_1-C_6)$-alkyl, unsubstituted or substituted with a substituent selected from the group consisting of:
  (i) -phenyl,
  (ii) —$(C_3-C_7)$-cycloalkyl,
  (iii) —$NR^7R^{11}$,
  (iv) -morpholin-4-yl,
  (v) —OH,
  (vi) —$CO_2R^7$, or
  (vii) —$CON(R^7)_2$,
(c) phenyl, unsubstituted or substituted with a substituent selected from the group consisting of:
  i) $(C_1-C_4)$-alkyl
  ii) —O—$(C_1-C_4)$-alkyl
  iii) —$CONR^7R^{11}$,
  iv) F, Cl, Br or I, or
  v) —$COOR^7$;

$R^9$ and $R^{10}$ are independently:
(a) H,
(b) $(C_1-C_6)$-alkyl, unsubstituted or substituted with $(C_3-C_7)$-cycloalkyl or —$CO_2R^7$,
(c) $(C_2-C_6)$-alkenyl,
(d) $(C_2-C_6)$-alkynyl,
(e) Cl, Br, F, I,
(f) $(C_1-C_6)$-alkoxy,
(g) perfluoro-$(C_1-C_6)$-alkyl,
(h) $(C_3-C_7)$-cycloalkyl, unsubstituted or substituted with $(C_1-C_6)$-alkyl,
(i) phenyl,
(j) $(C_1-C_6)$-alkyl—$S(O)_n$—$(CH_2)_n$—,
(k) hydroxy-$(C_1-C_6)$-alkyl,
(l) —CN,
(m) —$CO_2R^7$,
(n) —OH,
(o) —$NR^7R^{11}$,
(p) —$[(C_1-C_6)$-alkyl$]NR^7R^{11}$,
(q) —$NO_2$,
(r) —$(CH_2)_n$—$SO_2$—$N(R^7)_2$,
(s) —$NR^7CO$—$(C_1-C_4)$-alkyl, or
(t) —$CON(R^7)_2$;

$R^9$ and $R^{10}$ on adjacent carbons can join together to form a fused phenyl ring, unsubstituted or substituted with a substituent selected from the group consisting of: $(C_1-C_6)$-alkyl, $(C_1-C_6)$-alkoxy, $(C_3-C_7)$-cycloalkyl and $(C_1-C_6)$-alkyl—$(C_3-C_7)$-cycloalkyl, $R^{11}$ is
(a) $(C_1-C_6)$-alkyl, unsubstituted or substituted with a substituent selected from the group consisting of:
  i) —$OR^7$,
  ii) —$N[R^7]_2$,
  iii) —$NH_2$,
  iv —$COOR^7$,
  v) —$N[CH_2CH_2]_2Q$,
  vi) —$CF_3$, or
  vii) —$CON(R^7)_2$;
(b) aryl, wherein aryl is defined as phenyl or naphthyl which is unsubstituted or substituted with one or two substituents selected from the group consisting of:
  i) $(C_1-C_4)$-alkyl,
  ii) —O—$(C_1-C_4)$-alkyl,
  iii) —$CO[NR^7]_2$,
  iv) F, Cl, Br or I,
  v) —$COOR^7$,
  vi) —$NH_2$,
  vii) —$NH[(C_1-C_4)$-alkyl],
  viii) —$N[(C_1-C_4)$-alkyl$]_2$, or
  ix) —$CON[CH_2CH_2]_2Q$;
(c) —$(C_1-C_4)$-alkylaryl, wherein aryl is as defined above, (d) $(C_3-C_7)$-cycloalkyl,
(e)

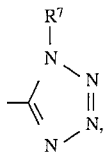

or
(f) $CF_3$;

$R^7$ and $R^{11}$ on the same nitrogen atom they can join together to form a ring selected from the group consisting of: morpholinyl, piperazinyl, or pyrrolyl, or Q is O, S or —$NR^7$;

$R^{12}$ is —$CONR^7(CH_2)_p$-E—$R^{16}$;

p is 0 to 4;

E is a single bond, NH, O, S, with the proviso that E is a single bond when p is 0 or 1;

X is
(a) —O—,
(b) —$S(O)_n$—,
(c) —$NR^7$—,
(d) —$CH_2O$—,
(e) —$CH_2S(O)_n$—,
(f) —$CH_2NR^7$—,
(g) —$OCH_2$—,
(h) —$N(R^7)CH_2$—,
(i) —$S(O)_nCH_2$—, or
(j) -single bond;

Z is:
(a) —$CO_2H$,
(b) —$CO_2R^{13}$,
(c) —CONH-(tetrazol-5-yl),
(d) —$CONHSO_2OR^{11}$,
(e) —$CONHSO_2NR^7R^{11}$
(f) —$CONHSO_2$-aryl, wherein aryl is defined as phenyl or naphthyl which is unsubstituted or substituted with one, two or three substituents selected from the group consisting of:
  i) $(C_1-C_4)$-alkyl,
  ii) —O—$(C_1-C_4)$-alkyl,
  iii) —$CONR^7R^{11}$,
  iv) F, Cl, Br or I,
  v) —$COOR^7$,
  vi) —$NH_2$,
  vii) —$NH[(C_1-C_4)$-alkyl],
  viii) —$N[(C_1-C_4)$-alkyl$]_2$,
  ix) -phenyl,
  x) —OH,
  xi) —$OCH_2CH_2OH$,
  xii) —$CF_3$;
(g) —$CONHSO_2$—$(C_1-C_8)$-alkyl, wherein the alkyl group is unsubstituted or substituted as defined in $R^4(b)$,
(h) —$CONHSO_2$—$(C_1-C_4)$-perfluoroalkyl,
(i) -tetrazol-5-yl,
(j) —$CONHSO_2$-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl or quinolinyl, which is unsubstituted or substituted with one, two or three substituents selected from the group consisting of:
  i) $(C_1-C_4)$-alkyl,
  ii) —O—$(C_1-C_4)$-alkyl, iii) —CONR⁷R¹¹,
iv) F, Cl, Br or I,
v) —COOR⁷,
vi) —NR⁷CONR⁷R¹¹, and
vii) —NR⁷COOR¹¹;

(k) —SO₂NHCO-aryl, wherein aryl is defined in Z(d) above, (l) —SO₂NHCO—(C₁-C₈)-alkyl, wherein the alkyl group is unsubstituted or substituted as defined in R⁴(b), (m) —SO₂NHCO—(C₁-C₄)-perfluoroalkyl, (n) —SO₂NHCO-heteroaryl, wherein heteroaryl is as defined in Z(g) above, (o) —SO₂NHCON(R¹¹)₂ wherein the R¹¹ groups are the same or different, (p) —PO(OR⁷)₂, wherein the R⁷ groups are the same or different, or (q) —PO(R¹¹)OR⁷;

R¹³ is:
(a) (C₁-C₄)-alkyl,
(b) CHR¹⁴—O—COR¹⁵,
(c) CH₂CH₂—N[(C₁-C₂)-alkyl]₂,
(d) CH₂CH₂—N[CH₂CH₂]₂O,
(e) (CH₂CH₂O)ᵧ-O-[(C₁-C₄)-alkyl], wherein y is 1 or 2,
(f) phenyl, naphthyl, CH₂-phenyl or CH₂-naphthyl, where phenyl or naphthyl is substituted or unsubstituted with CO₂—(C₁-C₄)-alkyl,

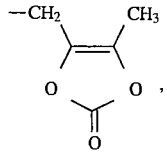 (g)

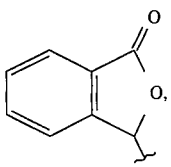 (h)

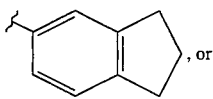 (i) , or

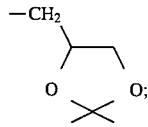 (j)

and

R¹⁴ and R¹⁵ independently are (C₁-C₆)-alkyl or phenyl;

R¹⁶ is a saturated or partially or fully unsaturated 5-membered heterocycle substituted with one, two or three heteroatoms selected from: N, O, and S, wherein the carbon skeleton of the heterocycle is mono- or di-substituted with R⁹ or an oxo group and the sp³ nitrogen atoms of the saturated or partially unsaturated heterocycle are substituted with R⁸, and with the proviso that R¹⁶ is not an N-linked pyrrolidine; and R¹⁷ is:
(a) H,
(b) (C₁-C₆)-alkyl, unsubstituted or substituted with (C₃-C₇)-cycloalkyl or —CO₂R⁷,
(c) (C₂-C₆)-alkenyl,
(d) (C₂-C₆)-alkynyl, (e) Cl, Br, F, I,
(f) (C₁-C₆)-alkoxy,
(g) perfluoro-(C₁-C₆)-alkyl,
(h) (C₃-C₇)-cycloalkyl, unsubstituted or substituted with (C₁-C₆)-alkyl,
(i) phenyl,
(j) (C₁-C₆)-alkyl—S(O)ₙ—(CH₂)ₙ—,
(k) hydroxy-(C₁-C₆)-alkyl,
(l) —CN,
(m) —CO₂R⁷,
(n) —OH,
(o) —NR⁷R¹¹,
(p) —[(C₁-C₆)-alkyl]NR⁷R¹¹,
(q) —NO₂,
(r) —(CH₂)ₙ—SO₂—N(R⁷)₂,
(s) —NR⁷CO—(C₁-C₄)-alkyl, or
(t) —CON(R⁷)₂.

An embodiment of this invention is concerned with novel compounds of structural formula I:

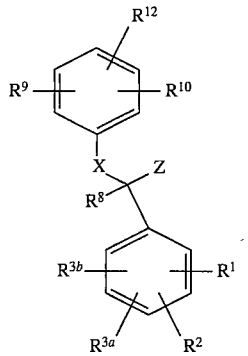 I or a pharmaceutically acceptable salt thereof, wherein:

R¹, R², R³ᵃ and R³ᵇ are independently:
(a) H,
(b) F, Cl, Br, or I,
(c) —NO₂,
(d) —NH₂,
(e) —NH(C₁-C₄)-alkyl,
(f) —N[(C₁-C₄)-alkyl]₂,
(g) —SO₂NHR⁷,
(h) —CF₃,
(i) (C₁-C₆)-alkyl,
(j) —OR⁷,
(k) —S(O)ₙ—(C₁-C₄)-alkyl,
(l) —NHCO—(C₁-C₄)-alkyl,
(m) —NHCO—O(C₁-C₄)-alkyl,
(n) —CH₂O—(C₁-C₄)-alkyl,
(o) —O—(CH₂)ₘ—OR⁷,
(p) —CONR⁷R¹¹, or
(q) —COOR⁷;

R¹ and R² on adjacent carbon atoms can be joined together to form a ring structure:

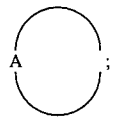

A represents:
a) —Y—C(R⁴)=C(R⁵)—,
b) —Y—C(R⁴)=N—,
c) —Y—N=C(R⁴)—,
d) —Y—[C(R⁶)(R⁶)]ₛ—Y—,
e) —Y—C(R⁶)(R⁶)—C(R⁶)(R⁶)—, f) —C(R⁴)=C(R⁵)—Y—,
g) —N=C(R⁴)—Y—,
h) —C(R⁶)(R⁶)—C(R⁶)(R⁶)—Y—, or
i) —C(R⁴)=C(R⁵)—C(R⁴)=C(R⁵)—;

m is 2, 3 or 4,
n is 0, 1 or 2,
s is 1 or 2,
Y is —O—, —S(O)$_n$— and NR⁷;
R⁴ and R⁵ are independently:
(a) H,
(b) ($C_1$–$C_6$)-alkyl or ($C_2$–$C_6$)-alkenyl each of which is unsubstituted or substituted with one or two substituents selected from the group consisting of:
  i) —OH,
  ii) —O—($C_1$–$C_4$)-alkyl,
  iii) —S(O)$_n$—($C_1$–$C_4$)-alkyl,
  iv) —NR⁷—($C_1$–$C_4$)-alkyl,
  v) —NHR⁷,
  vi) —COOR⁷,
  vii) —CONHR⁷,
  viii) —OCOR¹¹, or
  ix) —CONR⁷R¹¹,
(c) ($C_3$–$C_7$)-cycloalkyl,
(d) F, Cl, Br, I,
(e) CF₃,
(f) —COOR⁷,
(g) —CONR⁷R¹¹,
(h) —NR⁷R¹¹,
(i) —NR⁷CONR⁷R¹¹,
(j) —NR⁷COOR¹¹,
(k) —SO₂NR⁷R¹¹,
(l) —O—($C_1$–$C_4$)-alkyl,
(m) —S(O)$_n$—($C_1$–$C_4$)-alkyl, or
(n) —NHSO₂R¹¹;
R⁶ is:
(a) H,
(b) ($C_1$–$C_4$)-alkyl unsubstituted or substituted with one or two substituents selected from the group consisting of:
  i) —OH,
  ii) —NR⁷R¹¹,
  iii) —COOR⁷,
  iv) —CONHR⁷, or
  v) —CONR⁷R¹¹, or
(c) Cl, or F;
R⁷ is:
(a) H,
(b) ($C_1$–$C_6$)-alkyl,
(c) phenyl,
(d) ($C_1$–$C_6$)-alkylphenyl, or
(e) ($C_3$–$C_7$)-cycloalkyl;
R⁸ is:
(a) H,
(b) ($C_1$–$C_6$)-alkyl, unsubstituted or substituted with one or two substituents selected from the group consisting of:
  (i) -phenyl,
  (ii) —($C_3$–$C_7$)-cycloalkyl,
  (iii) —NR⁷R¹¹,
  (iv) -morpholin-4-yl,
  (v) —OH,
  (vi) —CO₂R⁷, or
  (vii) —CON(R⁷)₂, or
(c) phenyl;
R⁹ and R¹⁰ are independently:
(a) H,
(b) ($C_1$–$C_6$)-alkyl, unsubstituted or substituted with ($C_3$–$C_7$)-cycloalkyl or —CO₂R⁷,
(c) ($C_2$–$C_6$)-alkenyl,
(d) ($C_2$–$C_6$)-alkynyl,
(e) Cl, Br, F, I,
(f) ($C_1$–$C_6$)-alkoxy,
(g) perfluoro-($C_1$–$C_6$)-alkyl,
(h) ($C_3$–$C_7$)-cycloalkyl, unsubstituted or substituted with ($C_1$–$C_6$)-alkyl,
(i) phenyl,
(j) ($C_1$–$C_6$)-alkyl—S(O)$_n$—(CH₂)$_n$—,
(k) hydroxy-($C_1$–$C_6$)-alkyl,
(l) —CN,
(m) —CO₂R⁷,
(n) —OH,
(o) —NR⁷R¹¹,
(p)-[($C_1$–$C_6$)-alkyl]NR⁷R¹¹,
(q) —NO₂,
(r) —(CH₂)$_n$—SO₂—N(R⁷)₂,
(s) —NR⁷CO—($C_1$–$C_4$)-alkyl, or
(t) —CON(R⁷)₂;
R⁹ and R¹⁰ on adjacent carbons can join together to form a fused phenyl ring, unsubstituted or substituted with a substituent selected from the group consisting of: ($C_1$–$C_6$)-alkyl, ($C_1$–$C_6$)-alkoxy, ($C_3$–$C_7$)-cycloalkyl and ($C_1$–$C_6$)-alkyl—($C_3$–$C_7$)-cycloalkyl,
R¹¹ is
(a) ($C_1$–$C_6$)-alkyl, unsubstituted or substituted with a substituent selected from the group consisting of:
  i) —OR⁷,
  ii) —N[R⁷]₂,
  iii) —NH₂,
  iv) —COOR⁷,
  v) —N[CH₂CH₂]₂Q,
  vi) —CF₃, or
  vii) —CON(R⁷)₂;
(b) aryl, wherein aryl is defined as phenyl or naphthyl which is unsubstituted or substituted with one or two substituents selected from the group consisting of:
  i) ($C_1$–$C_4$)-alkyl,
  ii) —O—($C_1$–$C_4$)-alkyl,
  iii) —CO[NR⁷]₂,
  iv) F, Cl, Br or I,
  v) —COOR⁷,
  vi) —NH₂,
  vii) —NH[($C_1$–$C_4$)-alkyl],
  viii) —N[($C_1$–$C_4$)-alkyl]₂, or
  ix) —CON[CH₂CH₂]₂Q;
(c) —($C_1$–$C_4$)-alkylaryl, wherein aryl is as defined above,
($C_3$–$C_7$)-cycloalkyl,
(e)

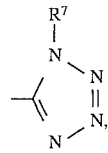

or
(f) CF₃;
R⁷ and R¹¹ on the same nitrogen atom they can join together to form a ring selected from the group consisting of: morpholinyl, piperazinyl, or pyrrolyl, or
Q is O, S or —NR⁷;
R¹² is —CONR⁷(CH₂)$_p$—E—R¹⁶;

p is 0 to 4;

E is a single bond, NH, O, S, with the proviso that E is a single bond when p is 0 or 1;

X is
- (a) —O—,
- (b) —S(O)$_n$—,
- (c) —NR$^7$—,
- (d) —CH$_2$O—,
- (e) —CH$_2$S(O)$_n$—,
- (f) —CH$_2$NR$^7$—,
- (g) —OCH$_2$—,
- (h) —N(R$^7$)CH$_2$—,
- (i) —S(O)$_n$CH$_2$—, or
- (j) -single bond;

Z is:
- (a) —CO$_2$H,
- (b) —CO$_2$R$^{13}$,
- (c) —CONH-(tetrazol-5-yl),
- (d) —CONHSO$_2$OR$^{11}$,
- (e) —CONHSO$_2$NR$^7$R$^{11}$,
- (f) —CONHSO$_2$-aryl, wherein aryl is defined as phenyl or naphthyl which is unsubstituted or substituted with one, two or three substituents selected from the group consisting of:
  - i) (C$_1$–C$_4$)-alkyl,
  - ii) —O—(C$_1$–C$_4$)-alkyl,
  - iii) —CONR$^7$R$^{11}$,
  - iv) F, Cl, Br or I,
  - v) —COOR$^7$,
  - vi) —NH$_2$,
  - vii) —NH[(C$_1$–C$_4$)-alkyl],
  - viii) —N[(C$_1$–C$_4$)-alkyl]$_2$,
  - ix) -phenyl,
  - x) —OH,
  - xi) —OCH$_2$CH$_2$OH,
  - xii) —CF$_3$;
- (g) —CONHSO$_2$—(C$_1$–C$_8$)-alkyl, wherein the alkyl group is unsubstituted or substituted as defined in R$^4$(b),
- (h) —CONHSO$_2$—(C$_1$–C$_4$)-perfluoroalkyl,
- (i) -tetrazol-5-yl,
- (j) —CONHSO$_2$-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl or quinolinyl, which is unsubstituted or substituted with one, two or three substituents selected from the group consisting of:
  - i) (C$_1$–C$_4$)-alkyl,
  - ii) —O—(C$_1$–C$_4$)-alkyl,
  - iii) —CONR$^7$R$^{11}$,
  - iv) F, Cl, Br or I,
  - v) —COOR$^7$,
  - vi) —NR$^7$CONR$^7$R$^{11}$, and
  - vii) —NR$^7$COOR$^{11}$;
- (k) —SO$_2$NHCO-aryl, wherein aryl is defined in Z(d) above,
- (l) —SO$_2$NHCO—(C$_1$–C$_8$)-alkyl, wherein the alkyl group is unsubstituted or substituted as defined in R$^4$(b),
- (m) —SO$_2$NHCO—(C$_1$–C$_4$)-perfluoroalkyl,
- (n) —SO$_2$NHCO—heteroaryl, wherein heteroaryl is as defined in Z(g) above,
- (o) —SO$_2$NHCON(R$^{11}$)$_2$ wherein the R$^{11}$ groups are the same or different,
- (p) —PO(OR$^7$)$_2$, wherein the R$^7$ groups are the same or different, or
- (q) —PO(R$^{11}$)OR$^7$;

R$^{13}$ is:
- (a) (C$_1$–C$_4$)-alkyl,
- (b) CHR$^{14}$—O—COR$^{15}$,
- (c) CH$_2$CH$_2$—N[(C$_1$–C$_2$)-alkyl]$_2$,
- (d) CH$_2$CH$_2$—N[CH$_2$CH$_2$]$_2$O,
- (e) (CH$_2$CH$_2$O)$_y$—O—[(C$_1$–C$_4$)-alkyl], wherein y is 1 or 2,
- (f) phenyl, naphthyl, CH$_2$-phenyl or CH$_2$-naphthyl, where phenyl or naphthyl is substituted or unsubstituted with CO$_2$—(C$_1$–C$_4$)-alkyl,

and

R$^{14}$ and R$^{15}$ independently are (C$_1$–C$_6$)-alkyl or phenyl; and

R$^{16}$ is a saturated or partially or fully unsaturated 5-membered heterocycle substituted with one, two or three heteroatoms selected from: N, O, and S, which is selected from the group consisting of:

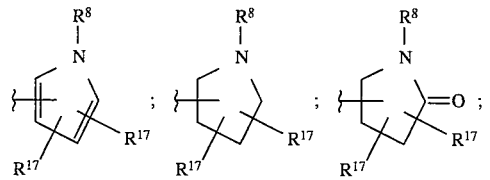

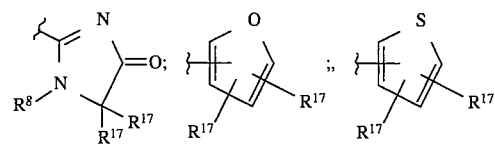

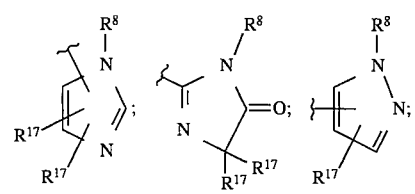

-continued

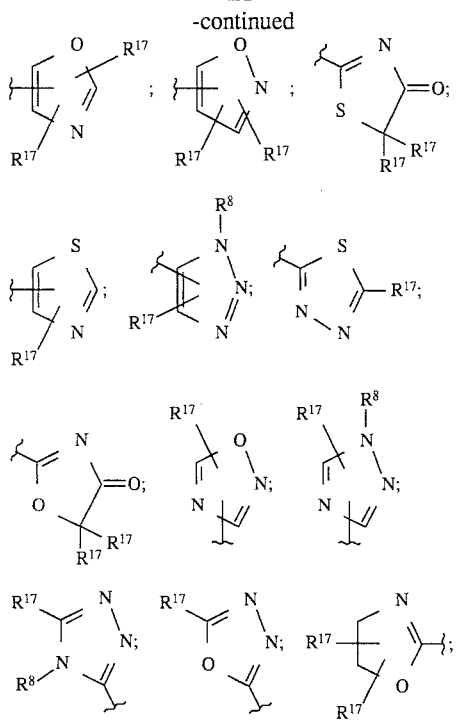

and

R¹⁷ is:
(a) H,
(b) (C₁–C₆)-alkyl, unsubstituted or substituted with (C₃–C₇)-cycloalkyl or —CO₂R⁷,
(c) (C₂–C₆)-alkenyl,
(d) (C₂–C₆)-alkynyl,
(e) Cl, Br, F, I,
(f) (C₁–C₆)-alkoxy,
(g) perfluoro-(C₁–C₆)-alkyl,
(h) (C₃–C₇)-cycloalkyl, unsubstituted or substituted with (C₁–C₆)-alkyl,
(i) phenyl,
(j) (C₁–C₆)-alkyl—S(O)ₙ—(CH₂)ₙ—,
(k) hydroxy-(C₁–C₆)-alkyl,
(l) —CN,
(m) —CO₂R⁷,
(n) —OH,
(o) —NR⁷R¹¹,
(p) —[(C₁–C₆)-alkyl]NR⁷R¹¹,
(q) —NO₂,
(r) —(CH₂)ₙ—SO₂—N (R⁷)₂,
(s) —NR⁷CO—(C₁–C₄)-alkyl, or
(t) —CON(R⁷)₂.

A second embodiment of the invention is the compound of structural formula II:

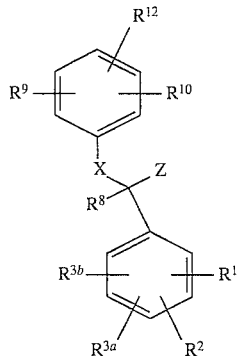

or a pharmaceutically acceptable salt thereof, wherein:
R¹, R², R³ᵃ and R³ᵇ are independently:
(a) H,
(b) F, Cl, Br, or I,
(c) —NO₂,
(d) —NH₂,
(e) —NH(C₁–C₄)-alkyl,
(f) —N[(C₁–C₄)-alkyl]₂,
(g) —SO₂NHR⁷,
(h) —CF₃,
(i) (C₁–C₆)-alkyl,
(j) —OR⁷,
(k) —S(O)ₙ—(C₁–C₄)-alkyl,
(l) —NHCO—(C₁–C₄)-alkyl,
(m) —NHCO—O(C₁–C₄)-alkyl,
(n) —CH₂O—(C₁–C₄)-alkyl,
(o) —(CH₂)ₘ—OR⁷,
(p) —CONR⁷R¹¹, or
(q) —COOR⁷;

R¹ and R² on adjacent carbon atoms can be joined together to form a ring structure:

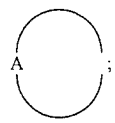

A represents:
a) —Y—C(R⁴)=C(R⁵)—,
b) —Y—C(R⁴)=N—,
c) —Y—N=C(R⁴)—,
d) —Y—[C(R⁶)(R⁶)]ₛ—Y—,
e) —Y—C(R⁶)(R⁶)—C(R⁶)(R⁶)—,
f) —C(R⁴)=C(R⁵)—Y—,
g) —N=C(R⁴)—Y—,
h) —C(R⁶)(R⁶)—C(R⁶)(R⁶)—Y—, or
i) —C(R⁴)=C(R⁵)—C(R⁴)=C(R⁵)—;

m is 2, 3 or 4,
n is 0, 1 or 2,
s is 1 or 2,
Y is —O—, —S(O)ₙ— and NR⁷;

$R^4$ and $R^5$ are independently: (a) H,
  (b) $(C_1–C_6)$-alkyl or $(C_2–C_6)$-alkenyl each of which is unsubstituted or substituted with one or two substituents selected from the group consisting of:
    i) —OH,
    ii) —O—$(C_1–C_4)$-alkyl,
    iii) —S(O)$_n$—$(C_1–C_4)$-alkyl,
    iv) —NR$^7$—$(C_1–C_4)$-alkyl,
    v) —NHR$^7$,
    vi) —COOR$^7$,
    vii) —CONHR$^7$,
    viii) —OCOR$^{11}$, or
    ix) —CONR$^7$R$^{11}$,
  (c) $(C_3–C_7)$-cycloalkyl,
  (d) F, Cl, Br, I,
  (e) CF$_3$,
  (f) —COOR$^7$,
  (g) —CONR$^7$R$^{11}$,
  (h) —NR$^7$R$^{11}$,
  (i) —NR$^7$CONR$^7$R$^{11}$,
  (j) —NR$^7$COOR$^{11}$,
  (k) —SO$_2$NR$^7$R$^{11}$,
  (l) —O—$(C_1–C_4)$-alkyl,
  (m) —S(O)$_n$—$(C_1–C_4)$-alkyl, or
  (n) —NHSO$_2$R$^{11}$;

$R^6$ is:
  (a) H,
  (b) $(C_1–C_4)$-alkyl unsubstituted or substituted with one or two substituents selected from the group consisting of:
    i) —OH,
    ii) —NR$^7$ R$^{11}$,
    iii) —COOR$^7$,
    iv) —CONHR$^7$, or
    v) —CONR$^7$R$^{11}$, or
  (c) Cl, or F;

$R^7$ is:
  (a) H,
  (b) $(C_1–C_6)$-alkyl,
  (c) phenyl,
  (d) $(C_1–C_6)$-alkylphenyl, or
  (e) $(C_3–C_7)$-cycloalkyl;

$R^8$ is:
  (a) H,
  (b) $(C_1–C_6)$-alkyl, unsubstituted or substituted with one or two substituents selected from the group consisting of:
    (i) -phenyl,
    (ii) —$(C_3–C_7)$-cycloalkyl,
    (iii) —NR$^7$R$^{11}$,
    (iv) -morpholin-4-yl,
    (v) —OH,
    (vi) —CO$_2$R$^7$, or
    (vii) —CON(R$^7$)$_2$, or
  (c) phenyl;

$R^9$ and $R^{10}$ are independently:
  (a) H,
  (b) $(C_1–C_6)$-alkyl, unsubstituted or substituted with $(C_3–C_7)$-cycloalkyl or —CO$_2$R$^7$,
  (c) $(C_2–C_6)$-alkenyl,
  (d) $(C_2–C_6)$-alkynyl,
  (e) Cl, Br, F, I,
  (f) $(C_1–C_6)$-alkoxy,
  (g) perfluoro-$(C_1–C_6)$-alkyl,
  (h) $(C_3–C_7)$-cycloalkyl, unsubstituted or substituted with $(C_1–C_6)$-alkyl,
  (i) phenyl,
  (j) $(C_1–C_6)$-alkyl—S(O)$_n$—(CH$_2$)$_n$—,
  (k) hydroxy-$(C_1–C_6)$-alkyl,
  (l) —CN,
  (m) —CO$_2$R$^7$,
  (n) —OH,
  (o) —NR$^7$R$^{11}$,
  (p) —[$(C_1–C_6)$-alkyl]NR$^7$R$^{11}$,
  (q) —NO$_2$,
  (r) —(CH$_2$)$_n$—SO$_2$—N(R$^7$)$_2$,
  (s) —NR$^7$CO—$(C_1–C_4)$-alkyl, or
  (t) —CON(R$^7$)$_2$;

$R^9$ and $R^{10}$ on adjacent carbons can join together to form a fused phenyl ring, unsubstituted or substituted with a substituent selected from the group consisting of: $(C_1–C_6)$-alkyl, $(C_1–C_6)$-alkoxy, $(C_3–C_7)$-cycloalkyl and $(C_1–C_6)$-alkyl-$(C_3–C_7)$-cycloalkyl, $R^{11}$ is
  (a) $(C_1–C_6)$-alkyl, unsubstituted or substituted with a substituent selected from the group consisting of:
    i) —OR$^7$,
    ii) —N[R$^7$]$_2$,
    iii) —NH$_2$,
    iv) —COOR$^7$,
    v) —N[CH$_2$CH$_2$]$_2$Q,
    vi) —CF$_3$, or
    vii) —CON(R$^7$)$_2$;
  (b) aryl, wherein aryl is defined as phenyl or naphthyl which is unsubstituted or substituted with one or two substituents selected from the group consisting of:
    i) $(C_1–C_4)$-alkyl,
    ii) —O—$(C_1–C_4)$-alkyl,
    iii) —CO[NR$^7$]$_2$,
    iv) F, Cl, B r or I,
    v) —COOR$^7$,
    vi) —NH$_2$,
    vii) —NH[$(C_1–C_4)$-alkyl],
    viii) —N[$(C_1–C_4)$-alkyl]$_2$, or
    ix) —CON[CH$_2$CH$_2$]$_2$Q;
  (c) —$(C_1–C_4)$-alkylaryl, wherein aryl is as defined above,
  (d) $(C_3–C_7)$-cycloalkyl,
  (e)

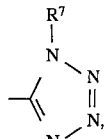

or
  (f) CF$_3$;

$R^7$ and $R^{11}$ on the same nitrogen atom they can join together to form a ring selected from the group consisting of: morpholinyl, piperazinyl, or pyrrolyl, or Q is O, or —NR$^7$;

$R^{12}$ is —CONR$^7$(CH$_2$)$_p$-E—R$^{16}$;

p is 0 to 4;

E is a single bond, NH, O, S, with the proviso that E is a single
bond when p is 0 or 1;

X is
  (a) —O—,
  (b) —S(O)$_n$—,
  (c) —NR$^7$—,
  (d) —CH$_2$O—, (e) —CH$_2$S(O)$_n$—,
(f) —CH$_2$NR$^7$—,
(g) —OCH$_2$—,
(h) —N(R$^7$)CH$_2$—,
(i) —S(O)$_n$CH$_2$—, or
(j) -single bond;

Z is:
(a) —CO$_2$H,
(b) —CO$_2$R$^{13}$,
(c) —CONH—(tetrazo 1-5-yl),
(d) —CONHSO$_2$OR$^{11}$,
(e) —CONHSO$_2$NR$^7$R$^{11}$,
(f) —CONHSO$_2$-aryl, wherein aryl is defined as phenyl or naphthyl which is unsubstituted or substituted with one, two or three substituents selected from the group consisting of:
  i) (C$_1$–C$_4$)-alkyl,
  ii) —O—(C$_1$–C$_4$)-alkyl,
  iii) —CONR$^7$R$^{11}$,
  iv) F, Cl, Br or I,
  v) —COOR$^7$,
  vi) —NH$_2$,
  vii) —NH[(C$_1$–C$_4$)-alkyl],
  viii) —N[(C$_1$–C$_4$)-alkyl]$_2$,
  ix) -phenyl,
  x) —OH,
  xi) —OCH$_2$CH$_2$OH,
  xii) —CF$_3$;
(g) —CONHSO$_2$—(C$_1$–C$_8$)-alkyl, wherein the alkyl group is unsubstituted or substituted as defined in R$^4$(b),
(h) —CONHSO$_2$—(C$_1$–C$_4$)-perfluoroalkyl,
(i) -tetrazol-5-yl,
(j) —CONHSO$_2$-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl or quinolinyl, which is unsubstituted or substituted with one, two or three substituents selected from the group consisting of:
  i) (C$_1$–C$_4$)-alkyl,
  ii) —O—(C$_1$–C$_4$)-alkyl,
  iii) —CONR$^7$R$^{11}$,
  iv) F, Cl, Br or I,
  v) —COOR$^7$,
  vi) —NR$^7$CONR$^7$R$^{11}$, and
  vii) —NR$^7$COOR$^{11}$,
(k) —SO$_2$NHCO-aryl, wherein aryl is defined in Z(d) above,
—SO$_2$NHCO—(C$_1$–C$_8$)-alkyl, wherein the alkyl group is unsubstituted or substituted as defined in R$^4$(b),
(m) —SO$_2$NHCO—(C$_1$–C$_4$)-perfluoroalkyl,
(n) —SO$_2$NHCO-heteroaryl, wherein heteroaryl is as defined in Z(g) above,
(o) —SO$_2$NHCON(R$^{11}$)$_2$ wherein the R$^{11}$ groups are the same or different,
(p) —PO(OR$^7$)$_2$, wherein the R$^7$ groups are the same or different, or
(q) —PO(R$^{11}$)OR$^7$;

R$^{13}$ is:
(a) (C$_1$–C$_4$)-alkyl,
(b) CHR$^{14}$—O—COR$^{15}$,
(c) CH$_2$CH$_2$—N[(C$_1$–C$_2$)-alkyl]$_2$,
(d) CH$_2$CH$_2$—N[CH$_2$CH$_2$]$_2$O,
(e) (CH$_2$CH$_2$O)$_y$—O—[(C$_1$–C$_4$)-alkyl], wherein y is 1 or 2, (f) phenyl, naphthyl, CH$_2$-phenyl or CH$_2$-naphthyl, where phenyl or naphthyl is substituted or unsubstituted with CO$_2$-(C$_1$–C$_4$)-alkyl,

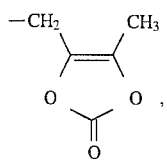 (g)

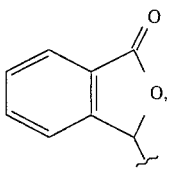 (h)

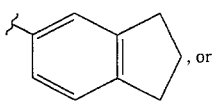, or (i)

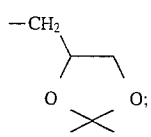 (j)

and

R$^{14}$ and R$^{15}$ independently are (C$_1$–C$_6$)-alkyl or phenyl; and

R$^{16}$ is a 5-membered partially or fully unsaturated heterocycle selected from the group consisting of:

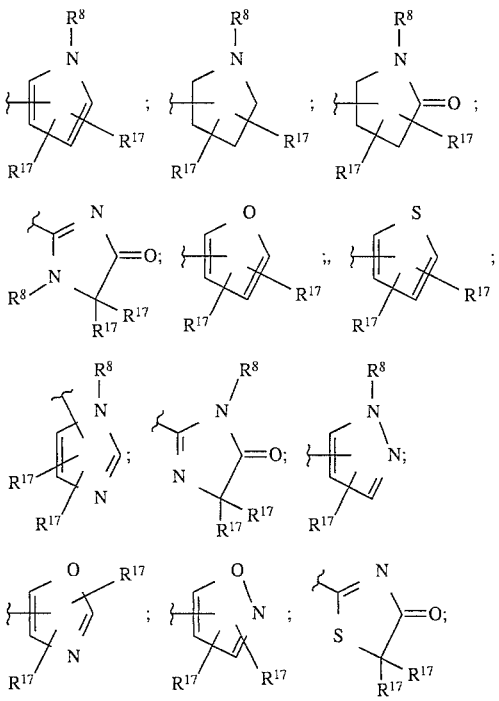

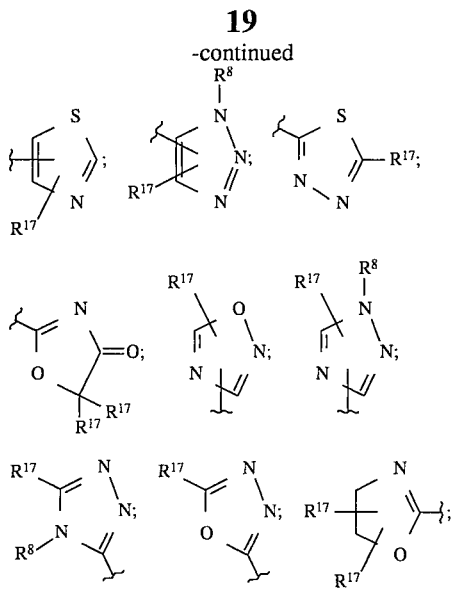

and

R¹⁷ is:
(a) H,
(b) $(C_1-C_6)$-alkyl, unsubstituted or substituted with $(C_3-C_7)$-cycloalkyl or $-CO_2R^7$,
(c) $(C_2-C_6)$-alkenyl,
(d) $(C_2-C_6)$-alkynyl,
(e) Cl, Br, F, I,
(f) $(C_1-C_6)$-alkoxy,
(g) perfluoro-$(C_1-C_6)$-alkyl,
(h) $(C_3-C_7)$-cycloalkyl, unsubstituted or substituted with $(C_1-C_6)$-alkyl,
(i) phenyl,
(j) $(C_1-C_6)$-alkyl—$S(O)_n$—$(CH_2)_n$—,
(k) hydroxy-$(C_1-C_6)$-alkyl,
(l) —CN,
(m) $-CO_2R^7$,
(n) —OH,
(o) $-NR^7R^{11}$,
(p) $-[(C_1-C_6)$-alkyl]$NR^7R^{11}$,
(q) $-NO_2$,
(r) $-(CH_2)_n-SO_2-N(R^7)_2$,
(s) $-NR^7CO-(C_1-C_4)$-alkyl, or
(t) $-CON(R^7)_2$.

An embodiment of the compounds of Formula II are the compounds of Formula III:

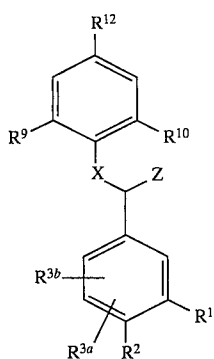    III or a pharmaceutically acceptable salt thereof, wherein:
$R^1$, $R^2$, $R^{3a}$ and $R^{3b}$ are independently:
(a) H,
(b) F, Cl, Br, or I,
(c) $-NO_2$,
(d) $(C_1-C_6)$-alkyl,
(e) $-OR^7$,
(f) $-NHCO-(C_1-C_4)$-alkyl,
(g) $-NHCO-O(C_1-C_4)$-alkyl,
(h) $-O-(CH_2)_m-OR^7$,
(i) $-CONR^7R^{11}$, or
(j) $-COOR^7$;

$R^1$ and $R^2$ on adjacent carbon atoms can be joined together to form a ring structure:

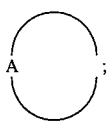

A represents:
a) $-Y-C(R^4)=C(R^5)-$,
b) $-Y-C(R^4)=N-$,
c) $-Y-N=C(R^4)-$,
d) $-Y-[C(R^6)(R^6)]_s-Y-$,
e) $-Y-C(R^6)(R^6)-C(R^6)(R^6)-$,
f) $-C(R^4)=C(R^5)-Y-$,
g) $-N=C(R^4)-Y-$,
h) $-C(R^6)(R^6)-C(R^6)(R^6)-Y-$, or
i) $-C(R^4)=C(R^5)-C(R^4)=C(R^5)-$;

m is 2, 3 or 4,
n is 0, 1 or 2,
s is 1 or 2,
Y is —O—, —S— and $NR^7$
$R^4$ and $R^5$ are independently:
(a) H,
(b) $(C_1-C_6)$-alkyl,
(c) $(C_3-C_7)$-cycloalkyl,
(d) F, Cl, Br, I,
(e) $-NR^7COOR^{11}$,
(f) $-SO_2NR^7R^{11}$,
(g) $-O-(C_1-C_4)$-alkyl,
(h) $-S(O)_n-(C_1-C_4)$-alkyl, or
(i) $-NHSO_2R^{11}$;

$R^6$ is:
(a) H, or
(b) $(C_1-C_4)$-alkyl, or
(c) Cl, or F;

$R^7$ is:
(a) H,
(b) $(C_1-C_6)$-alkyl,
(c) phenyl, or
(d) benzyl;

$R^8$ is:
(a) H,
(b) $(C_1-C_6)$-alkyl, or
(c) phenyl;

$R^9$ and $R^{10}$ are independently:
(a) H,
(b) $(C_1-C_6)$-alkyl, unsubstituted or substituted with $(C_3-C_7)$-cycloalkyl,
(c) Cl, Br, F, I,
(d) $(C_1-C_6)$-alkoxy, or
(e) hydroxy-$(C_1-C_6)$-alkyl;

$R^{11}$ is
(a) $(C_1-C_6)$-alkyl, unsubstituted or substituted with a substituent selected from the group consisting of:
i) $-OR^7$,
ii) $-N[R^7]_2$,
iii) $-NH_2$, iv) —COOR⁷,
v) —N[CH₂CH₂]₂Q,
vi) —CF₃, or
vii) —CON(R⁷)₂;
(b) aryl, wherein aryl is defined as phenyl or naphthyl which is unsubstituted or substituted with one or two substituents selected from the group consisting of:
i) (C₁-C₄)-alkyl,
ii) —O—(C₁-C₄)-alkyl,
iii) —CO[NR⁷]₂,
iv) F, Cl, Br or I,
v) —COOR⁷,
vi) —NH₂,
vii) —NH[(C₁-C₄)-alkyl],
viii) —N[(C₁-C₄)-alkyl]₂,
ix) —CON[CH₂CH₂]₂Q, or
(c) —(C₁-C₄)-alkylaryl, wherein aryl is as defined above,
(d) (C₃-C₇)-cycloalkyl,
(e)

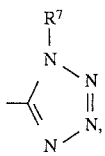

or
(f) CF₃;
R⁷ and R¹¹ on the same nitrogen atom they can join together to form a ring selected from the group consisting of: morpholinyl, piperazinyl, or pyrrolyl, or
Q is O, or —NR⁷;
R¹² is —CONR⁷(CH₂)$_p$—E—R¹⁶;
p is 0 to 4;
E is a single bond, NH, O, S, with the proviso that E is a single bond when p is 0 or 1;
X is
(a) —O—,
(b) —NR⁷, or
(c) -single bond;
Z is:
(a) —CO₂H,
(b) —CO₂R¹³,
(c) —CONH (tetrazol-5-yl),
(d) —CONHSO₂NR⁷R¹¹,
(e) —CONHSO₂-aryl, wherein aryl is defined as phenyl or naphthyl which is unsubstituted or substituted with one, two or three substituents selected from the group consisting of:
i) (C₁-C₄)-alkyl,
ii) —O—(C₁-C₄)-alkyl,
iii) —CONR⁷R¹¹,
iv) F, Cl, Br or I,
v) —COOR⁷,
vi) —NH₂,
vii) —NH[(C₁-C₄)-alkyl],
viii) —N[(C₁-C₄)-alkyl]₂,
ix) -phenyl;
(f) —CONHSO₂—(C₁-C₈)-alkyl, wherein alkyl is unsubstituted or substituted as defined in R⁴(b),
(g) —CONHSO₂-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl, or quinolinyl, which is unsubstituted or substituted with one, two or three substituents selected from the group consisting of:
i) (C₁-C₄)-alkyl,
ii) —O—(C₁-C₄)-alkyl,
iii) —CONR⁷R¹¹,
iv) F, Cl, Br or I,
v) —COOR⁷,
vi) —NR⁷CONR⁷R¹¹, and
vii) —NR⁷COOR¹¹;
(h) -tetrazol-5-yl;
R¹³ is: (C₁-C₄)-alkyl; and
R¹⁶ is a 5-membered partially or fully unsaturated heterocycle selected from the group consisting of:

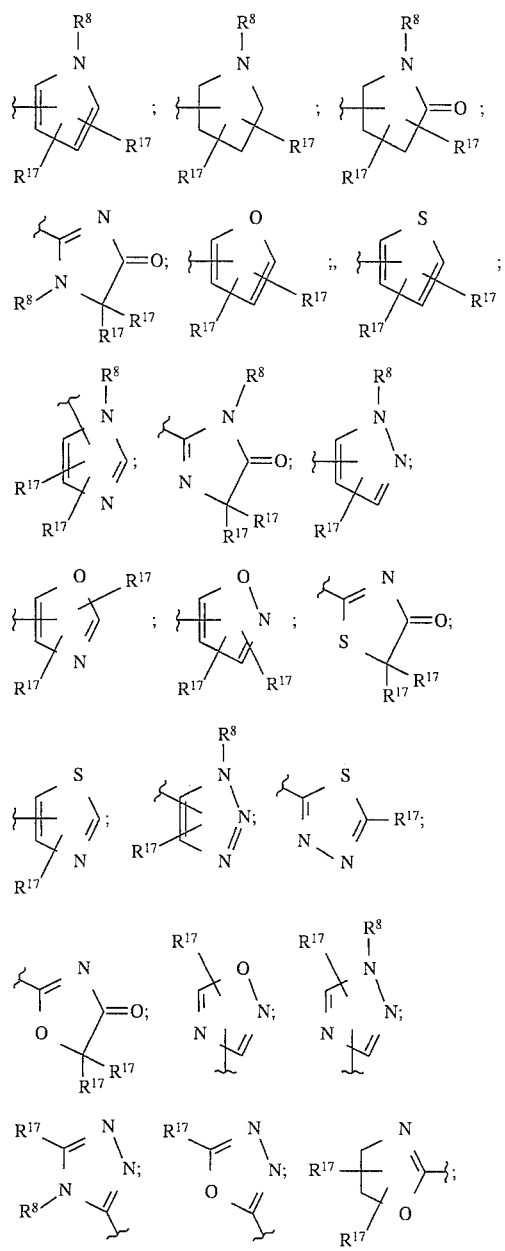

and
R¹⁷ is:
(a) H, (b) (C₁-C₆)-alkyl, unsubstituted or substituted with
(C₃-C₇)-cycloalkyl,
(c) Cl, Br, F, I, (d) $(C_1-C_6)$-alkoxy,
(e) perfluoro-$(C_1-C_6)$-alkyl,
(f) hydroxy-$(C_1-C_6)$-alkyl,
(g) —CN,
(h) —$CO_2R^7$,
(i) —OH,
(j) —$NR^7R^{11}$,
(k) —$CON(R^7)_2$.

A subclass of the compounds of Formula III are the compounds of Formula IV:

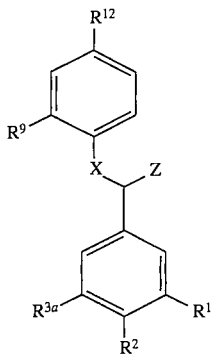

or a pharmaceutically acceptable salt thereof, wherein:
$R^1$ and $R^2$ taken together form the ring structure:

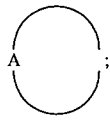

A represents:
a) —Y—$[C(R^6)(R^6)]_s$—Y—, or
b) —$C(R^4)$=$C(R^5)$—$C(R^4)$=$C(R^5)$—;
s is 1 or 2;
Y is —O—;
$R^{3a}$ is:
 (a) H,
 (b) F, Cl, Br, or I,
 (c) $(C_1-C_6)$-alkyl,
 (d) —$OR^7$,
 (e) —O—$(CH_2)_m$—$OR^7$,
 (f) —$CONR^7R^{11}$, or
 (g) —$COOR^7$;
m is 2, 3 or 4;
$R^4$ and $R^5$ are independently:
 (a) H,
 (b) $(C_1-C_6)$-alkyl,
 (c) $(C_3-C_7)$-cycloalkyl,
 (d) F, Cl, Br, I,
 (e) —$NR^7COOR^{11}$,
 (f) —$SO_2NR^7R^{11}$,
 (g) —O—$(C_1-C_4)$-alkyl,
 (h) —$S(O)_n$—$(C_1-C_4)$-alkyl, or
 (i) —$NHSO_2R^{11}$;
n is 0, 1 or 2,
$R^6$ is:
 (a) H, or
 (b) $(C_1-C_4)$-alkyl, or
 (c) Cl, or F;
$R^7$ is:
 (a) H,
 (b) $(C_1-C_6)$-alkyl,
 (c) phenyl, or
 (d) benzyl;
$R^8$ is:
 (a) H,
 (b) $(C_1-C_6)$-alkyl, or
 (c) phenyl;
$R^9$ is:
 (a) H,
 (b) $(C_1-C_6)$-alkyl, unsubstituted or substituted with $(C_3-C_7)$-cycloalkyl,
 (c) Cl, Br, F, I,
 (d) $(C_1-C_6)$-alkoxy, or
 (e) hydroxy-$(C_1-C_6)$-alkyl;
$R^{11}$ is
 (a) $(C_1-C_6)$-alkyl, unsubstituted or substituted with a substituent selected from the group consisting of:
  i) —$OR^7$,
  ii) —$N[R^7]_2$,
  iii) —$NH_2$,
  iv) —$COOR^7$,
  v) —$N[CH_2CH_2]_2Q$,
  vi) —$CF_3$, or
  vii) —$CON(R^7)_2$;
 (b) aryl, wherein aryl is defined as phenyl or naphthyl which is unsubstituted or substituted with one or two substituents selected from the group consisting of:
  i) $(C_1-C_4)$-alkyl,
  ii) —O—$(C_1-C_4)$-alkyl,
  iii) —$CO[NR^7]_2$,
  iv) F, Cl, Br or I,
  v) —$COOR^7$,
  vi) —$NH_2$,
  vii) —$NH[(C_1-C_4)$-alkyl],
  viii) —$N[(C_1-C_4)$-alkyl$]_2$, or
  ix) —$CON[CH_2CH_2]_2Q$;
 (c) —$(C_1-C_4)$-alkylaryl, wherein aryl is as defined above,
 (d) $(C_3-C_7)$-cycloalkyl,
 (e)

$$\begin{array}{c} R^7 \\ | \\ N \\ \diagdown \\ \diagup\diagdown \quad N \\ \quad \quad || \\ \quad \quad N, \\ N \diagup \end{array}$$

or
 (f) $CF_3$;
$R^7$ and $R^{11}$ on the same nitrogen atom they can join together to form a ring selected from the group consisting of: morpholinyl, piperazinyl, or pyrrolyl, or
Q is O, S or —$NR^7$;
$R^{12}$ is —$CONR^7(CH_2)_p$—E—$R^{16}$;
p is 0 to 4;
E is a single bond, NH, O, S, with the proviso that E is a single bond when p is 0 or 1;
X is
 (a) —O—,
 (b) —$NR^7$, —or
 (c) -single bond;
Z is:
 (a) —$CO_2H$,
 (b) —$CO_2R^{13}$,
 (c) —CONH-(tetrazol-5-yl),
 (d) —$CONHSO_2NR^7R^{11}$,
 (e) —$CONHSO_2$-aryl, wherein aryl is defined as phenyl or naphthyl which is unsubstituted or substituted with one, two or three substituents selected from the group consisting of:
i) $(C_1-C_4)$-alkyl,
ii) —O—$(C_1-C_4)$-alkyl,
iii) —CONR$^7$R$^{11}$,
iv) F, Cl, Br or I,
v) —COOR$^7$,
vi) —NH$_2$,
vii) —NH[$(C_1-C_4)$-alkyl],
viii) —N[$(C_1-C_4)$-alkyl]$_2$,
ix) -phenyl;
(f) —CONHSO$_2$—$(C_1-C_8)$-alkyl, wherein alkyl is unsubstituted or substituted as defined in R$^4$(b),
(g) —CONHSO$_2$-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl, or quinolinyl, which is unsubstituted or substituted with one, two, or three substituents selected from the group consisting of:
i) $(C_1-C_4)$-alkyl,
ii) —O—$(C_1-C_4)$-alkyl,
iii) —CONR$^7$R$^{11}$,
iv) F, Cl, Br or I,
v) —COOR$^7$,
vi) —NR$^7$CONR$^7$R$^{11}$, and
vii) —NR$^7$COOR$^{11}$;
(h) -tetrazol-5-yl;

R$^{13}$ is: $(C_1-C_4)$-alkyl; and

R$^{16}$ is a 5-membered partially or fully unsaturated heterocycle selected from the group consisting of:

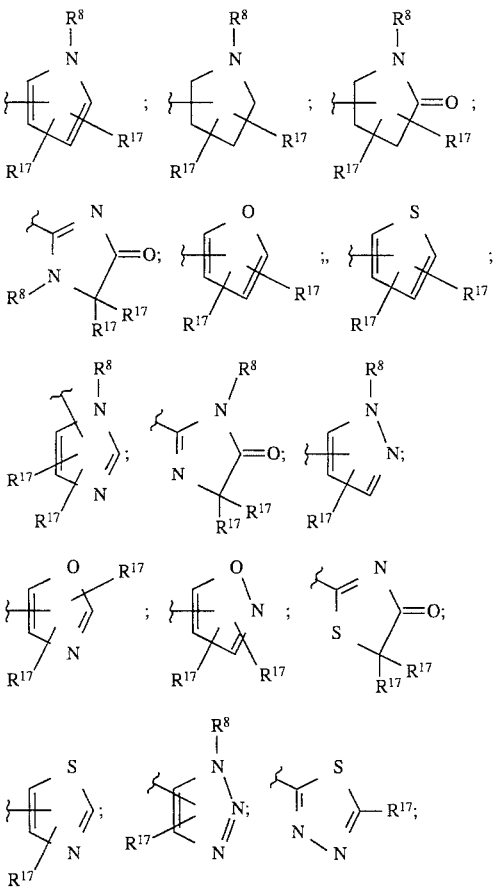

and
R$^{17}$ is:
(a) H,
(b) $(C_1-C_6)$-alkyl, unsubstituted or substituted with $(C_3-C_7)$-cycloalkyl,
(c) Cl, Br, F, I,
(d) $(C_1-C_6)$-alkoxy,
(e) perfluoro-$(C_1-C_6)$-alkyl,
(f) hydroxy-$(C_1-C_6)$-alkyl,
(g) —CN,
(h) —CO$_2$R$^7$,
(i) —OH,
(j) —NR$^7$R$^{11}$,
(k) —CON(R$^7$)$_2$.

Another subclass of the compounds of Formula IV are:

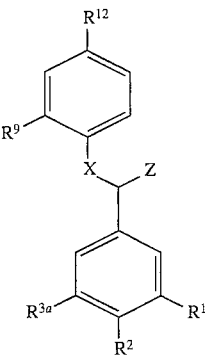

IV or a pharmaceutically acceptable salt thereof, wherein:
R$^1$, R$^2$, R$^{3a}$ and R$^{3b}$ are independently:
(a) H,
(b) F, Cl, Br, or I,
(c) —NO$_2$,
(d) $(C_1-C_6)$-alkyl,
(e) —OR$^7$,
(f) —NHCO—$(C_1-C_4)$-alkyl,
(g) —NHCO—O$(C_1-C_4)$-alkyl,
(h) —O—$(CH_2)_m$—OR$^7$,
(i) —CONR$^7$R$^{11}$, or
(j) —COOR$^7$;
m is 2, 3 or 4,
R$^4$ and R$^5$ are independently:
(a) H,
(b) $(C_1-C_6)$-alkyl,
(c) $(C_3-C_7)$-cycloalkyl,
(d) F, Cl, Br, I,
(e) —NR$^7$COOR$^{11}$,
(f) —SO$_2$NR$^7$R$^{11}$,
(g) —O—$(C_1-C_4)$-alkyl,
(h) —S(O)$_n$—$(C_1-C_4)$-alkyl, or
(i) —NHSO$_2$R$^{11}$;

n is 0, 1 or 2,

R⁶ is:
(a) H,
(b) ($C_1$–$C_4$)-alkyl, or
(c) Cl or F;

R⁷ is:
(a) H,
(b) ($C_1$–$C_6$)-alkyl,
(c) phenyl, or
(d) benzyl;

R⁸ is:
(a) H,
(b) ($C_1$–$C_6$)-alkyl, or
(c) phenyl;

R⁹ is:
(a) H,
(b) ($C_1$–$C_6$)-alkyl, unsubstituted or substituted with ($C_3$–$C_7$)-cycloalkyl,
(c) Cl, Br, F, I,
(d) ($C_1$–$C_6$)-alkoxy, or
(e) hydroxy-($C_1$–$C_6$)-alkyl;

R¹¹ is
(a) ($C_1$–$C_6$)-alkyl, unsubstituted or substituted with a substituent selected from the group consisting of:
  i) —OR⁷,
  ii) —N[R⁷]₂,
  iii) —NH₂,
  iv) —COOR⁷,
  v) —N[CH₂CH₂]₂Q,
  vi) —CF₃, or
  vii) —CON(R⁷)₂;
(b) aryl, wherein aryl is defined as phenyl or naphthyl which is unsubstituted or substituted with one or two substituents selected from the group consisting of:
  i) ($C_1$–$C_4$)-alkyl,
  ii) —O—($C_1$–$C_4$)-alkyl,
  iii) —CO[NR⁷]₂,
  iv) F, Cl, Br or I,
  v) —COOR⁷,
  vi) —NH₂,
  vii) —NH[($C_1$–$C_4$)-alkyl],
  viii) —N[($C_1$–$C_4$)-alkyl]₂, or
  ix) —CON[CH₂CH₂]₂Q;
(c) —($C_1$–$C_4$)-alkylaryl, wherein aryl is as defined above,
(d) ($C_3$–$C_7$)-cycloalkyl,
(e)

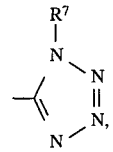

or
(f) CF₃;

R⁷ and R¹¹ on the same nitrogen atom they can join together to form a ring selected from the group consisting of: morpholinyl, piperazinyl, or pyrrolyl, or Q is O, or —NR⁷;

R¹² is —CONR⁷(CH₂)$_p$—E—R¹⁶;

p is 0 to 4;

E is a single bond, NH, O, S, with the proviso, that E is a single bond when p is 0 or 1;

X is (a) —O—,
(b) —NR⁷—, or
(c) -single bond;

Z is:
(a) —CO₂H,
(b) —CO₂R¹³,
(c) —CONH-(tetrazol-5-yl),
(d) —CONHSO₂NR⁷R¹¹,
(e) —CONHSO₂-aryl, wherein aryl is defined as phenyl or naphthyl which is unsubstituted or substituted with one, two or three substituents selected from the group consisting of:
  i) ($C_1$–$C_4$)-alkyl,
  ii) —O—($C_1$–$C_4$)-alkyl,
  iii) —CONR⁷R¹¹,
  iv) F, Cl, Br or I,
  v) —COOR⁷,
  vi) —NH₂,
  vii) —NH[($C_1$–$C_4$)-alkyl],
  viii) —N[($C_1$–$C_4$)-alkyl]₂,
  ix) -phenyl;
(f) —CONHSO₂—($C_1$–$C_8$)-alkyl, wherein alkyl is unsubstituted or substituted as defined in R⁴(b),
(g) —CONHSO₂-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl, or quinolinyl, which is unsubstituted or substituted with one, two or three substituents selected from the group consisting of:
  i) ($C_1$–$C_4$)-alkyl,
  ii) —O—($C_1$–$C_4$)-alkyl,
  iii) —CONR⁷R¹¹,
  iv) F, Cl, Br or I,
  v) —COOR⁷,
  vi) —NR⁷CONR⁷R¹¹, and
  vii) —NR⁷COOR¹¹;
(h) -tetrazol-5-yl;

R¹³ is: ($C_1$–$C_4$)-alkyl; and

R¹⁶ is a 5-membered partially or fully unsaturated heterocycle selected from the group consisting of:

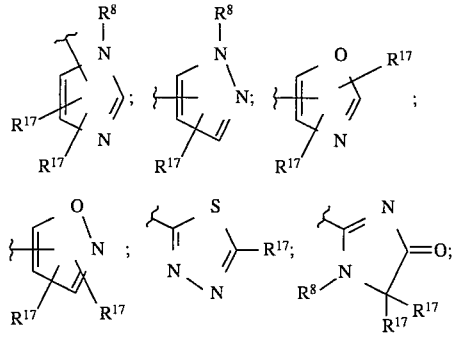

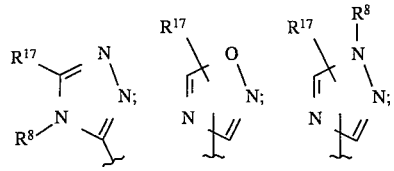

R¹⁷ is:
(a) H,
(b) ($C_1$–$C_6$)-alkyl, unsubstituted or substituted with ($C_3$–$C_7$)-cycloalkyl, (c) Cl, Br, F, I,
(d) $(C_1-C_6)$-alkoxy,
(e) perfluoro-$(C_1-C_6)$-alkyl,
(f) hydroxy-$(C_1-C_6)$-alkyl,
(g) —CN,
(h) —$CO_2R^7$,
(i) —OH
(j) —$NR^7R^{11}$,
(k) —$CON(R^7)_2$.

A second embodiment of the compounds of Formula II are the compounds of Formula V:

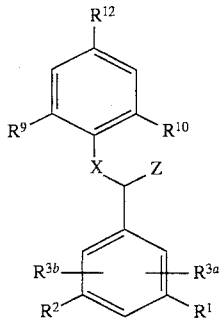 V or a pharmaceutically acceptable salt thereof, wherein:

$R^1$, $R^2$, $R^{3a}$ and $R^{3b}$ are independently:
(a) H,
(b) F, Cl, Br, or I,
(c) —$NO_2$,
(d) $(C_1-C_6)$-alkyl,
(e) —$OR^7$,
(f) —NHCO—$(C_1-C_4)$-alkyl,
(g) —NHCO—$O(C_1-C_4)$-alkyl,
(h) —O—$(CH_2)_m$—$OR^7$,
(i) —$CONR^7R^{11}$, or
(j) —$COOR^7$;

m is 2, 3 or 4, $R^4$ add $R^5$ are independently:
(a) H,
(b) $(C_1-C_6)$-alkyl,
(c) $(C_3-C_7)$-cycloalkyl,
(d) F, Cl, Br, I,
(e) —$NR^7 COOR^{11}$,
(f) —$SO_2NR^7R^{11}$,
(g) —O—$(C_1-C_4)$-alkyl,
(h) —$S(O)_n$—$(C_1-C_4)$-alkyl, or
(i) —$NHSO_2R^{11}$;

n is 0, 1 or 2, $R^6$ is:
(a) H,
(b) $(C_1-C_4)$-alkyl, or
(c) Cl or F;

$R^7$ is:
(a) H,
(b) $(C_1-C_6)$-alkyl,
(c) phenyl, or
(d) benzyl;

$R^8$ is:
(a) H,
(b) $(C_1-C_6)$-alkyl, or
(c) phenyl;

$R^9$ and $R^{10}$ are independently:
(a) H,
(b) $(C_1-C_6)$-alkyl, unsubstituted or substituted with $(C_3-C_7)$-cycloalkyl,
(c) Cl, Br, F, I,
(d) $(C_1-C_6)$-alkoxy, or
(e) hydroxy-$(C_1-C_6)$-alkyl;

$R^{11}$, is
(a) $(C_1-C_6)$-alkyl, unsubstituted or substituted with a substituent selected from the group consisting of:
  i) —$OR^7$,
  ii) —$N[R^7]2$,
  iii) —$NH_2$,
  iv) —$COOR^7$,
  v) —$N[CH_2CH_2]_2Q$,
  vi) —$CF_3$, or
  vii) —$CON(R^7)_2$;
(b) aryl, wherein aryl is defined as phenyl or naphthyl which is unsubstituted or substituted with one or two substituents selected from the group consisting of:
  i) $(C_1-C_4)$-alkyl,
  ii) —O—$(C_1-C_4)$-alkyl,
  iii) —$CO[NR^7]_2$,
  iv) F, Cl, Br or I,
  v) —$COOR^7$,
  vi) —$NH_2$,
  vii) —$NH[(C_1-C_4)$-alkyl],
  viii) —$N[(C_1-C_4)$-alkyl]$_2$, or
  ix) —$CON[CH_2CH_2]_2Q$;
(c) —$(C_1-C_4)$-alkylaryl, wherein aryl is as defined above,
(d) $(C_3-C_7)$-cycloalkyl,
(e)

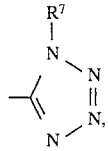

or
(f) $CF_3$;

$R^7$ and $R^{11}$ on the same nitrogen atom they can join together to form a ring selected from the group consisting of: morpholinyl, piperazinyl, or pyrrolyl, or Q is O, or —$NR^7$;

$R^{12}$ is —$CONR^7(CH_2)_p$—E—$R^{16}$;

p is 0 to 4;

E is a single bond, NH, O, S, with the proviso that E is a single bond when p is 0 or 1;

X is
(a) —O—,
(b) —$NR^7$—, or
(c) -single bond;

Z is:
(a) —$CO_2H$,
(b) —$CO_2R^{13}$,
(c) —CONH-(tetrazol-5-yl),
(d) —$CONHSO_2NR^7R^{11}$,
(e) —$CONHSO_2$-aryl, wherein aryl is defined as phenyl or naphthyl which is unsubstituted or substituted with one, two or three substituents selected from the group consisting of:
  i) $(C_1-C_4)$-alkyl,
  ii) —O—$(C_1-C_4)$-alkyl,
  iii) —$CONR^7R^{11}$,
  iv) F, Cl, Br or I,
  v) —$COOR^7$,
  vi) —$NH_2$,
  vii) —$NH[(C_1-C_4)$-alkyl], viii) —N[($C_1$–$C_4$)-alkyl]$_2$,
ix) -phenyl;
(f) —CONHSO$_2$—($C_1$–$C_8$)-alkyl, wherein alkyl is unsubstituted or substituted as defined in $R^4$(b),
(g) —CONHSO$_2$-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl, or quinolinyl which is unsubstituted or substituted with one, two or three substituents selected from the group consisting of:
  i) ($C_1$–$C_4$)-alkyl,
  ii) —O—($C_1$–$C_4$)-alkyl,
  iii) —CONR$^7$R$^{11}$,
  iv) F, Cl, Br or I,
  v) —COOR$^7$,
  vi) —NR$^7$CONR$^7$R$^{11}$, and
  vii) —NR$^7$COOR$^{11}$;
(h) -tetrazol-5-yl;

$R^{13}$ is: ($C_1$–$C_4$)-alkyl; and $R^{16}$ is a 5-membered partially or fully unsaturated heterocycle selected from the group consisting of:

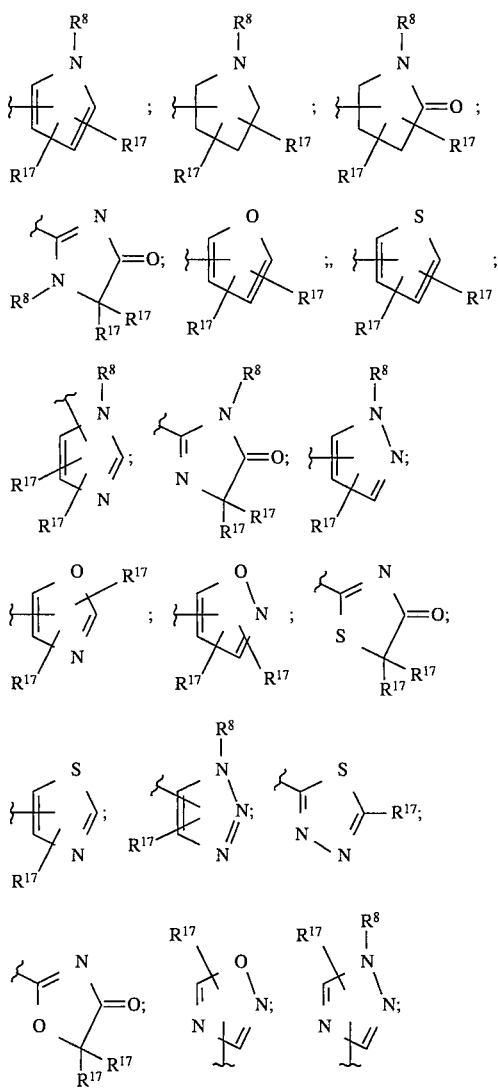

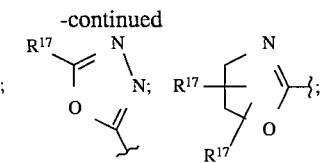

and $R^{17}$ is:
(a) H,
(b) ($C_1$–$C_6$)-alkyl, unsubstituted or substituted with ($C_3$–$C_7$)-cycloalkyl,
(c) Cl, Br, F, I,
(d) ($C_1$–$C_6$)-alkoxy,
(e) perfluoro-($C_1$–C6)-alkyl,
(f) hydroxy-($C_1$–$C_6$)-alkyl,
(g) —CN,
(h) —CO$_2$R$^7$,
(i) —OH,
(j) —NR$^7$R$^{11}$,
(k) —CON(R$^7$)$_2$.

A third embodiment of compounds of Formula II are the compounds of Formula VI:

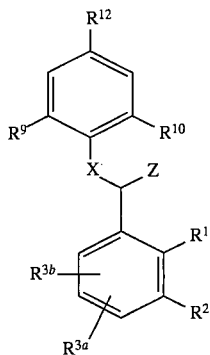

VI or a pharmaceutically acceptable salt thereof, wherein:
$R^1$ and $R^2$ are represented by the following ring structure:

A represents:
  a) —Y—[C(R$^6$)(R$^6$)]$_s$—Y—, or
  b) —C(R$^4$)=C(R$^5$)—C (R$^4$)=C(R$^5$)—;
s is 1 or 2,
Y is —O—, —S— and NR$^7$;
$R^{3a}$ and $R^{3b}$ are independently:
  (a) H,
  (b) F, Cl, Br, or I,
  (c) —NO$_2$,
  (d) ($C_1$–$C_6$)-alkyl,
  (e) —OR$^7$,
  (f) —NHCO—($C_1$–$C_4$)-alkyl,
  (g) —NHCO—O($C_1$–$C_4$)-alkyl,
  (h) —O—(CH$_2$)$_m$—OR$^7$,
  (i) —CONR$^7$R$^{11}$, or
  (j) —COOR$^7$;
m is 2, 3 or 4,
$R^4$ and $R^5$ are independently:
  (a) H,
  (b) ($C_1$–$C_6$)-alkyl,
  (c) ($C_3$–$C_7$)-cycloalkyl, (d) F, Cl, Br, I,
(e) —NR⁷COOR¹¹,
(f) —SO₂NR⁷R¹¹,
(g) —O—(C₁–C₄)-alkyl,
(h) —S(O)ₙ—(C₁–C₄)-alkyl, or
(i) —NHSO₂R¹¹;

n is 0, 1 or 2, $R^6$ is:
(a) H, or
(b) (C₁–C₄)-alkyl, or
(c) Cl or F;

$R^7$ is:
(a) H,
(b) (C₁–C₆)-alkyl,
(c) phenyl, or
(d) benzyl;

$R^8$ is:
(a) H,
(b) (C₁–C₆)-alkyl, or
phenyl;

$R^9$ and $R^{10}$ independently:
(a) H,
(b) (C₁–C₆)-alkyl, unsubstituted or substituted with (C₃–C₇)-cycloalkyl,
(c) Cl, Br, F, I,
(d) (C₁–C₆)-alkoxy, or
(e) hydroxy-(C₁–C₆)-alkyl;

$R^{11}$
(a) (C₁–C₆)-alkyl, unsubstituted or substituted with a substituent selected from the group consisting of:
 i) —OR⁷,
 ii) —N[R⁷]₂,
 iii) —NH₂,
 iv) —COOR⁷,
 v) —N[CH₂CH₂]₂Q,
 vi) —CF₃, or
 vii) —CON(R⁷)₂;
(b) aryl, wherein aryl is defined as phenyl or naphthyl which is unsubstituted or substituted with one or two substituents selected from the group consisting of:
 i) (C₁–C₄)-alkyl,
 ii) —O—(C₁–C₄)-alkyl,
 iii) —CO[NR⁷]₂,
 iv) F, Cl, Br or I,
 v) —COOR⁷,
 vi) —NH₂,
 vii) —NH[(C₁–C₄)-alkyl],
 viii) —N[(C₁–C₄)-alkyl]₂, or
 ix) —CON[CH₂CH₂]₂Q;
(c) —(C₁–C₄)-alkylaryl, wherein aryl is as defined above,
(d) (C₃–C₇)-cycloalkyl,
(e)

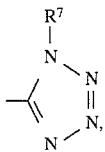

or
(f) CF₃;

$R^7$ and $R^{11}$ on the same nitrogen atom they can join together to form a ring selected from the group consisting of: morpholinyl, piperazinyl, or pyrrolyl, or Q is O, or —NR⁷;

$R^{12}$ is —CONR⁷(CH₂)ₚ—E—R¹⁶;

p is 0 to 4;

E is a single bond, NH, O, S, with the proviso that E is a single bond when p is 0 or 1;

X is
(a) —O—,
(b) —NR⁷—, or
(c) -single bond;

Z is:
(a) —CO₂H,
(b) —CO₂R¹³,
(c) —CONH—(tetrazol-5-yl),
(d) —CONHSO₂NR⁷R¹¹,
(e) —CONHSO₂—aryl, wherein aryl is defined as phenyl or naphthyl which is unsubstituted or substituted with one, two or three substituents selected from the group consisting of:
 i) (C₁–C₄)-alkyl,
 ii) —O—(C₁–C₄)-alkyl,
 iii) —CONR⁷R¹¹,
 iv), F, Cl, Br or I,
 v) —COOR⁷,
 vi) —NH₂,
 vii) —NH[(C₁–C₄)-alkyl],
 viii) —N[(C₁–C₄)-alkyl]₂,
 ix) -phenyl;
(f) —CONHSO₂—(C₁–C₈)-alkyl, wherein alkyl is unsubstituted or substituted as defined in R⁴(b),
(g) —CONHSO₂—heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl, or quinolinyl, which is unsubstituted or substituted with one, two or three substituents selected from the group consisting of:
 i) (C₁–C₄)-alkyl,
 ii) —O—(C₁–C₄)-alkyl,
 iii) —CONR⁷R¹¹,
 iv) F, Cl, B r or I,
 v) —COOR⁷,
 vi) —NR⁷CONR⁷R¹¹, and
 vii) —NR⁷COOR¹¹;
(h) -tetrazol-5-yl;

$R^{13}$: (C₁–C₄)-alkyl; and $R^{16}$ is a 5-membered partially or fully unsaturated heterocycle selected from the group consisting of:

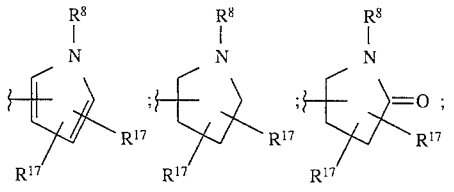

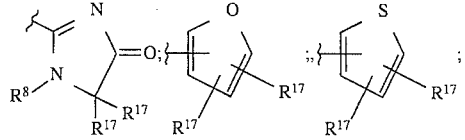

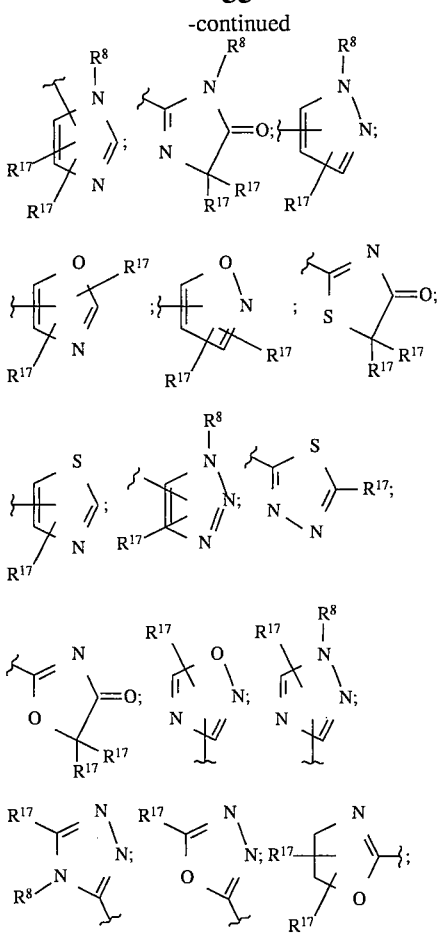

and
R¹⁷ is:
(a) H,
(b) (C₁-C₆)-alkyl, unsubstituted or substituted with (C₃-C₇)-cycloalkyl or —CO₂R⁷,
(c), (C₂-C₆)-alkenyl,
(d) (C₂-C₆)-alkynyl,
(e) Cl, Br, F, I,
(f) (C₁-C₆)-alkoxy,
(g) perfluoro-(C₁-C₆)-alkyl,
(h) (C₃-C₇)-cycloalkyl, unsubstituted or substituted with (C₁-C₆)-alkyl,
(i) phenyl,
(j) (C₁-C₆)- alkyl—S(O)ₙ—(CH₂)ₙ—,
(k) hydroxy-(C₁-C₆)-alkyl,
(l) —CN,
(m) —CO₂R⁷,
(n) —OH,
(o) —NR⁷R¹¹,
(p) —[(C₁C₆)-alkyl]NR⁷R¹¹,
(q) —NO₂,
(r) —(CH₂)ₙ—SO₂—N(R⁷)₂,
(s) —NR⁷CO—(C₁-C₄)-alkyl, or
(t) —CON(R⁷)₂.

A preferred embodiment of the compounds of this invention are:

N-(4-isopropylbenzenesulfonyl)-α-[2-n-propyl-4-[[(1,2,4-triazol-3-yl)amino]carbonyl]phenoxy]-3,4-(methylenedioxy)phenylacetamide;

N-(4-isopropylbenzenesulfonyl)-α-[2-n-propyl-4-[[(thiazol-2-yl)amino]carbonyl]phenoxy]-3,4-(methylenedioxy)phenylacetamide;

N-(4-isopropylbenzenesulfonyl)-α-[2-n-propyl-4-[[1,3,4-thiadiazol-2-yl)-amino]carbonyl]phenoxy]-3,4-(methylenedioxy)phenylacetamide;

N-(4-isopropylbenzenesulfonyl)-α-[2-n-propyl-4-[[(4,5-dimethyloxazol-2-yl)amino]carbonyl]phenoxy]-3,4-(methylenedioxy)phenylacetamide;

N-(4-isopropylbenzenesulfonyl)-α-[2-n-propyl-4-[[(4,5-dihydro-1-methyl-4-oxo-1H-imidazol-2-yl)amino]carbonyl]phenoxy]-3,4-(methylenedioxy)phenylacetamide;

N-(4-isopropylbenzenesulfonyl)-α-[2-n-propyl-4-[[(1-methyl-1H-imidazol-2-yl)amino]carbonyl]phenoxy]-3,4-(methylenedioxy)phenylacetamide;

N-(4-isopropylbenzenesulfonyl)-α-[2-n-propyl-4-[[(4,5-dihydro-4-oxothiazol-2-yl)amino]carbonyl]phenoxy]-3,4-(methylenedioxy)phenylacetamide;

N-(4-isopropylbenzenesulfonyl)-α-[2-n-propyl-4-[[[(2-furyl)methyl]amino]carbonyl]phenoxy]-3,4-(methylenedioxy)phenylacetamide;

N-(4-isopropylbenzenesulfonyl)-α-[2-n-propyl-4-[[(5-methylisoxazol-3-yl)amino]carbonyl]phenoxy]-3,4-(methylenedioxy)phenylacetamide;

N-(4-isopropylbenzenesulfonyl)-α-[2-n-propyl-4-[[(5-methyl-1H-pyrazol-3-yl)amino]carbonyl]phenoxy]-3,4-(methylenedioxy)phenylacetamide;

N-(4-isopropylbenzenesulfonyl)-α-[2-n-propyl-4-[[(1-methyl-1H-pyrazol-5-yl)amino]carbonyl]phenoxy]-3,4-(methylenedioxy)phenylacetamide;

N-(4-isopropylbenzenesulfonyl)-α-[2-n-propyl-4-[[(4-cyano-1H-pyrazol-3-yl)amino]carbonyl]phenoxy]-3,4-(methylenedioxy)phenylacetamide;

N-(4-isopropylbenzenesulfonyl)-α-[2-n-propyl-4-[[(Δ²-oxazolin-2-yl)amino]carbonyl]phenoxy]-3,4-(methylenedioxy)-phenylacetamide;

N-(4-isopropylbenzenesulfonyl)-α-[2-n-propyl-4-[[[(2-thienyl)methyl]amino]carbonyl]phenoxy]-3,4-(methylenedioxy)plenylactamide;

N-(4-isopropylbenzenesulfonyl)-α-[2-n-propyl-4-[[(4,5-dicyanoimidazol-2-yl)amino]carbonyl]phenoxy]-3,4-(methylenedioxy)phenylacetamide;

N-(4-isopropylbenzenesulfonyl)-α-[2-n-propyl4-[[(5-methyl-1,2,4-triazol-3-yl)amino]carbonyl]phenoxy]-3,4-(methylenedioxy)phenylacetamide;

N-(4-isopropylbenzenesulfonyl)-α-[2-n-propyl-4-[[(1-methyl-1H-1,2,4-triazol-3-yl)amino]carbonyl]phenoxy]-3,4-(methylenedioxy)phenylacetamide;

N-(4-isopropylbenzenesulfonyl)-α-[2-n-propyl-4-[[(4-methyl-4H-1,2,4-triazol-3-yl)amino]carbonyl]phenoxy]-3,4-(methylenedioxy)phenylacetamide;

N-(4-isopropylbenzenesulfonyl)-α-[2-n-propyl-4-[[(5-trifluoromethyl-4H-1,2,4-triazol-3-yl)amino]carbonyl]phenoxy]-3,4-(methylenedioxy)phenylacetamide;

N-(4-isopropylbenzenesulfonyl)-α-[2-n-propyl-4-[[(imidazol-2-yl)amino]carbonyl]phenoxy]-3,4-(methylenedioxy)phenylacetamide;

N-(4-isopropylbenzenesulfonyl)-α-[2-n-propyl-4-[[[(imidazol-2-yl)methyl]amino]carbonyl]phenoxy]-3,4-(methylenedioxy)phenylacetamide;

N-(4-isopropylbenzenesulfonyl)-α-[2-n-propyl-4-[[(4-(aminocarbonyl)-1,2,3-triazol-5-yl)amino]carbonyl]phenoxy]-3,4(methylenedioxy)phenylacetamide;

N-(4-isopropylbenzenesulfonyl)-α-[2-n-propyl-4-[[(4,5-dihydro-4-oxo-1H-imidazol-2-yl)amino]carbonyl]phenoxy]-3,4-(methylenedioxy)phenylacetamide;

N-(4-isopropylbenzenesulfonyl)-α-[2-n-propyl-4-[[[(1-ethylpyrrolidin-2-yl)methyl]amino]carbonyl]phenoxy]-3,4-(methylenedioxy)phenylacetamide;

N-(4-isopropylbenzenesulfonyl)-α-[2-n-propyl-4-[[[(1,2,4-oxadiazol-3-yl)methyl]amino]carbonyl]phenoxy]-3,4-(methylenedioxy)phenylacetamide.

A preferred embodiment of the compounds of this invention are:

N-(4-isopropylbenzenesulfonyl)-α-[2-n-propyl-4-[[(1,2,4-triazol-3yl)amino]carbonyl]phenoxy]-3,4-(methylenedioxy)phenylacetamide;

N-(4-isopropylbenzenesulfonyl)-α-[2-n-propyl-4-[[(thiazol-2-yl)amino]carbonyl]phenoxy]-3,4-(methylenedioxy)phenylacetamide;

N-(4-isopropylbenzenesulfonyl)-α-[2-n-propyl-4-[[(thiadiazol-3-yl)amino]carbonyl]phenoxy]-3,4-(methylenedioxy)phenylacetamide;

N-(4-isopropylbenzenesulfonyl)-α-[2-n-propyl-4-[[(4,5-dimethyloxazol-2-yl)amino]carbonyl]phenoxy]-3,4-(methylenedioxy)phenylacetamide;

N-(4-isopropylbenzenesulfonyl)-α-[2-n-propyl 4-[[(4,5-dihydro-1-methyl-4-oxo-1H-imidazol-2-yl)amino]carbonyl]phenoxy]-3,4-(methylenedioxy)phenylacetamide;

N-(4-isopropylbenzenesulfonyl)-α-[2-n-propyl-4-[[(1-methyl-1H-imidazol-2-yl)amino]carbonyl]phenoxy]-3,4-(methylenedioxy)phenylacetamide;

N-(4-isopropylbenzenesulfonyl)-α-[2-n-propyl-4-[[(4,5-dihydro-4-oxothiazol-2-yl)amino]carbonyl]phenoxy]-3,4-(methylenedioxy)phenylacetamide;

N-(4-isopropylbenzenesulfonyl)-α-[2-n-propyl-4-[[[(2-furyl)methyl]amino]carbonyl]phenoxy]-3,4-(methylenedioxy)phenylacetamide;

N-(4-isopropylbenzenesulfonyl)-α-[2-n-propyl-4-[[(5-methylisoxazol-3-yl) amino]carbonyl]phenoxyl]-3,4-(methylenedioxy)phenylacetamide;

N-(4-isopropylbenzenesulfonyl)-α-[2-n-propyl-4-[[(5-methyl-1H-pyrazol-3-yl)amino]carbonyl]phenoxy]-3,4-(methylenedioxy)phenylacetamide;

N-(4-isopropylbenzenesulfonyl)-α-[2-n-propyl-4-[[(1-methyl-1H-pyrazol-5-yl)amino]carbonyl]phenoxy]-3,4-(methylenedioxy)phenylacetamide;

N-(4-isopropylbenzenesulfonyl)-α-[2-n-propyl-4-[[[(2-thienyl)methyl]amino]carbonyl]phenoxy]-3,4-(methylenedioxy)phenylacetamide;

N-(4-isopropylbenzenesulfonyl)-α-[2n-propyl-4-[[(1-methyl-1H-1,2,4-triazol-3-yl)amino]carbonyl]phenoxy]-3,4-(methylenedioxy)phenylacetamide;

N-(4-isopropylbenzenesulfonyl)-α-[2-n-propyl-4-[[[(imidazol-2-yl)methyl]carbonyl]phenoxy]-3,4-(methylenedioxy)phenylacetamide;

N-(4-isopropylbenzenesulfonyl)-α-[2-n-propyl-4-[[(4-(aminocarbonyl)-1,2,3-triazol-5-yl)amino]carbonyl]phenoxy]-3,4-(methylenedioxy)phenylacetamide;

N-(4-isopropylbenzenesulfonyl)-α-[2-n-propyl-4-[[(4,5-dihydro-4-oxo-1H-imidazol-2-yl)amino]carbonyl]phenoxy]-3,4-(methylenedioxy)phenylacetamide;

N-(4-isopropylbenzenesulfonyl)-α-[2-n-propyl-4-[[[(1-ethylpyrrolidin-2-yl) methyl]amino]carbonyl]phenoxy]-3,4-methylenedioxy)phenylacetamide;

N-(4-isopropylbenzenesulfonyl)-α-[2-n-propyl-4-[[[(1,2,4-oxadiazol-3-yl)methyl]amino]carbonyl]phenoxy]-3,4-(methylenedioxy)phenylacetamide.

The alkyl substituents recited above denote straight and branched chain hydrocarbons of the length specified such as methyl, ethyl, isopropyl, isobutyl, neopentyl, isopentyl, etc.

The alkenyl-substituents denote alkyl groups as described above which are modified so that each contains a carbon to carbon double bond such as vinyl, allyl and 2-butenyl.

Cycloalkyl denotes rings composed of 3 to 8 methylene groups, each of which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl or quinolinyl.

The heterocyclic amides can exist in tautomeric forms as depicted below:

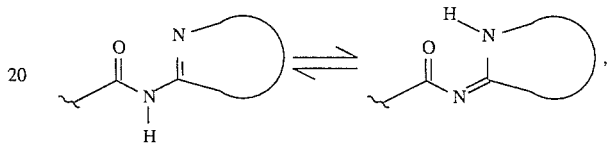

as well as the oxo substituted dihydro heterocycles as represented with the 4,5-dihydro-4-oxoimidazole shown below:

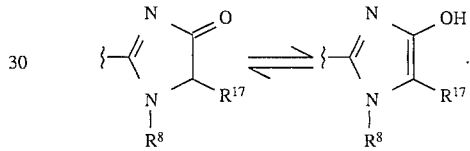

Although the reaction schemes described below are reasonably general, it will be understood by those skilled in the art of organic synthesis that one or more functional groups present in a given compound of Formula I may render the molecule incompatible with a particular synthetic sequence. In such a case an alternative synthetic route, an altered order of steps, or a strategy of protection and deprotection may be employed. In all cases the particular reaction conditions, including reagents, solvent, temperature and time, should be chosen so that they are consistent with the nature of the functionality present in the molecule.

The compounds of Formula I and specifically compounds of Formula III can be synthesized using the reactions and techniques described for the synthesis of the non-heterocyclic components in the patent application WO91/11999 (Merck & Co.; published on Aug. 22, 1991 under the Patent Cooperation Treaty) and also U.S. Pat. No. 5,177,095 (Merck & Co.; Jan. 5, 1993) and U.S. Pat. No. 5,240,938 (Merck & Co.; Aug. 31, 1993).

The reaction schemes described below have been generalized for simplicity. It is further to be understood that in the generalized schemes below, unless specified more narrowly in the text, the alkyl and aryl groups represent unfunctionalized or functionalized derivatives as described before. The leaving group Q present in the alkylating agents is either chloro, bromo, iodo, methanesulfonate, p-toluenesulfonate or triflate.

Scheme 1

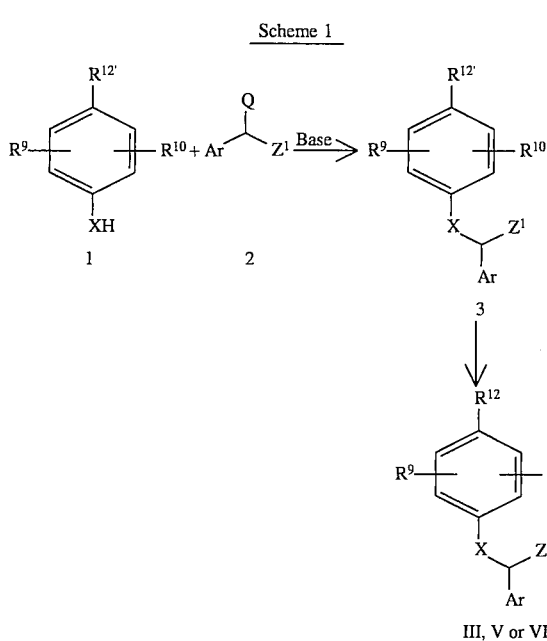

Q = Cl, Br, I, OMs, OTs or OTf
$Z^1$ = a precursor to Z
$R^{12'}$ = a precursor to $R^{12}$ More specifically, the compounds of Formula III, V or VI (where X is oxygen, sulphur or appropriately substituted nitrogen) can be synthesized as outlined in Scheme 1. The substituted compound 1 may be reacted with the alkylating agent 2 in an appropriate solvent such as alcohols (methanol, ethanol, isopropanol and like), dimethylformamide (DMF), dimethylsulfoxide (DMSO), tetrahydrofuran (THF) and acetone in the presence of an alkali metal salt such as alkoxides, carbonates, hydroxides and hydrides, or organic bases such as trialkylamines or alkyl lithiums to provide compound 3. The $R^{12'}$ and $Z^1$ groups present in compound 3 may then be further transformed to provide the appropriate compounds of Formula III, V or VI.

A preferred intermediate of structure 1, wherein $R^{12'}$ is $CO_2CH_3$, $R^9$ is n-propyl, and X is H, may be prepared according to the methods described in U.S. Pat. No. 5,240,938, as outlined in Scheme 1a.

Scheme 1a

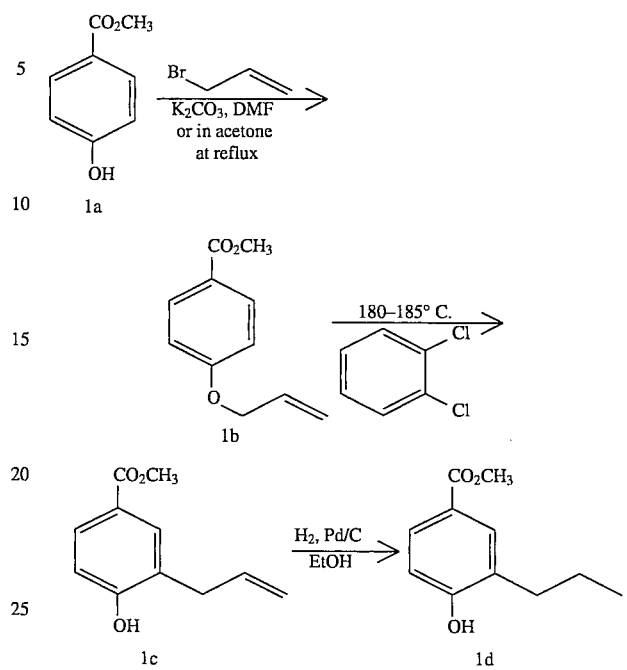

Methyl 4-hydroxybenzoate (1a) is alkylated with allyl bromide in the presence of a base such as potassium carbonate in a solvent such as dimethylformamide (DMF) at 20°–40° C. or in acetone at reflux, to give the alkyl ether 1b. The ally/ether undergoes a Claisen rearrangement to give 1c upon heating with 1,2-dichlorobenzene at approximately 180° to 185° C. Hydrogenation of the allyl group of 1c in the presence of a suitable catalyst such as palladium on carbon, affords methyl 4-hydroxy-3-n-propylbenzoate, compound 1d, which may then be reacted with a compound of structure 2, as described in Scheme 1.

In general, the alkylating agent 2 can be prepared using methods and techniques outlined in U.S. Pat. No. 5,177,095. More specifically, compound 2 (where $Z^1$ is COOR and Q is Br) can be synthesized from the substituted arylacetic acids t as outlined in Scheme 2. The substituted arylacetic acid 4 is convened to the corresponding ester either by refluxing the acid in an appropriate alcohol in the presence of a catalytic amount of conc. sulfuric acid, or using other conventional methods of esterification. The resulting ester is then refluxed in carbon tetrachloride with N-bromosuccinimide and a catalytic amount of a radical initiator (e.g., AIBN or benzoylperoxide) to provide the 2-bromo-arylacetic acid ester 5.

Scheme 2

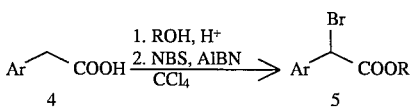

Alternatively, the ester 5 may also be prepared from appropriate aryl aldehydes (Scheme 3). The aldehyde 6 can be reacted with trimethylsilyl cyanide and catalytic amounts of KCN and 18-crown-6 to provide the corresponding trimethylsilyl cyanohydrin 7, which upon further treatment with the gaseous HCl and alcohol affords the 2-hydroxy ester 8. The ester 8 is treated with triphenylphosphine and carbon tetrabromide in methylene chloride to give the 2-bromoarylacetate derivatives 5.

Scheme 3

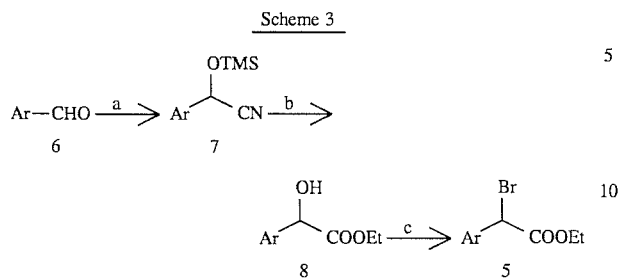

a. TMSCN, Cat. KCN, CH$_2$Cl$_2$, 18-Crown-6;
b. HCl(g), EtOH;
c. CBr$_4$, Ph$_3$P, CH$_2$Cl$_2$ Scheme 4 illustrates a typical synthesis of an alkylating agent 12 (where Ar represents a heterocycle such as an indole). The appropriately substituted cyanoindole 9 (for a general synthesis of substituted indoles refer to, R. K. Brown, *Indoles, Part One*, Ed. W. J. Houlihan, Vol. 25, Chapter II, Wiley-Interscience, New York, 1972) is reduced with DIBAL-H to provide the corresponding aldehyde, which is then convened into the N-Boc derivative 10. Reaction of 10 with the trichloromethane anion [generated from KOH and CHCl$_3$; J. M. Wyvratt et. al., *J. Org. Chem.*, 52, 944–945 (1987)] followed by treatment with aqueous NaOH in DMF provides the alcohol 11. Treatment of 11 with diazomethane followed by the reaction with CBr$_4$/Ph$_3$P yields the alkylating agent 12.

Scheme 4

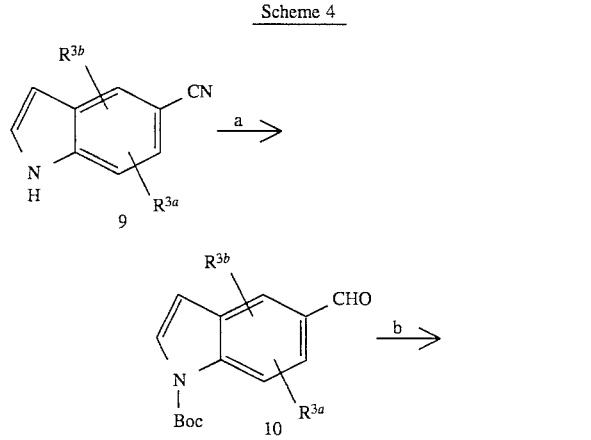

Scheme 4 -continued

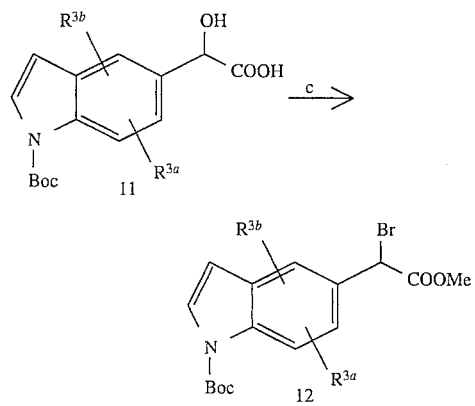

a. (i) DIBALH, Toluene; (ii) Boc$_2$O, DMAP, CH$_2$Cl$_2$
b. (i) CHCl$_3$, KOH, DMF, 0° C.; (ii) NaOH, DME/H$_2$O
c. (i) CH$_2$N$_2$; (ii) CBr$_4$/Ph$_3$P, CH$_2$Cl$_2$ A typical synthesis of alkylating agents bearing a substituted benzoxazole or benzthiazole ring is outlined in Scheme 5. The substituted benzoxazole 14 is prepared from the corresponding o-aminophenol 13 by the reaction of an appropriate orthoester under refluxing conditions (for other methods of synthesis of benzoxazoles see, S. A. Lang and Y. Lin, *Comprehensive Heterocyclic Chemistry*, Vol. 6, 1–130, Ed. C. W. Rees; and references cited therein). Reduction of 14 with NaBH$_4$ provides the alcohol 15 which is then subjected to pyridinium dichromate (PDC) oxidation to yield the corresponding aldehyde 16. Further elaboration of 16 as outlined provides the key intermediate 17. Similarly, the benzothiazole 19 can also be prepared form the appropriately substituted o-aminothiophenol 18.

Scheme 5

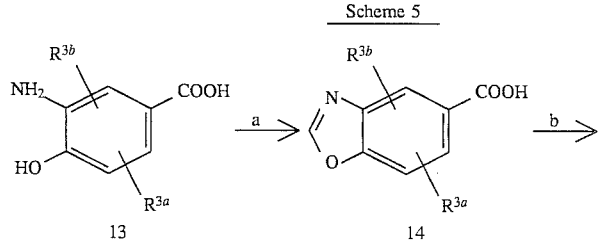

-continued
Scheme 5

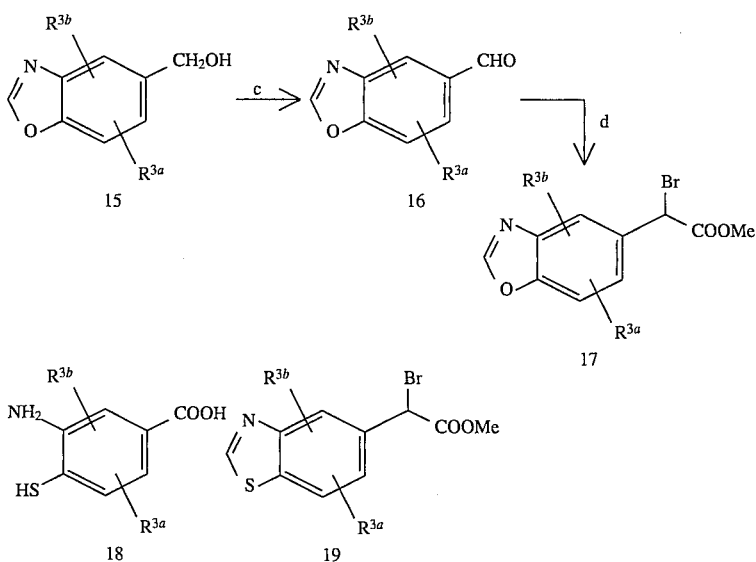

a. CH(OEt)₃, EtOH, reflux
b. (i)ClCOOEt, Et₃N, THF; (ii) NaBH₄, THF—H₂O
c. Pyridinium dichromate, CH₂Cl₂
d. (i) CHCl₃, KOH, DMF, 0° C.; (ii) NaOH, DME/H₂O;
   (iii)HCl/MeOH; (iv) CBr₄/Ph₃P, CH₂Cl₂

Scheme 6 illustrates the synthesis of benzofuran and dihydrobenzofuran alkylating agents 23 and 25. The benzofuran 21 can be prepared from the α-phenoxy carbonyl compound 20 via a ring closure reaction. [Stoermer and Wehln, *Chem. Ber.*, 35, 3549 (1902)] (for general methods of synthesis of benzofurans and dihydrobenzofurans see, R. C. Elderfield and V. B. Meyer, *Heterocyclic Compounds*, Vol. 2, Chapter 1, Ed. R. C. Elderfield, Wiley; and references cited therein). The ester 21 is reduced to provide the aldehyde 22 which is then transformed into the corresponding alkylating agent 23. The dihydrobenzofuran ester 24, obtained by catalytic reduction of 21, can also be transformed into the corresponding alkylating agent 25 using the sequence of reactions outlined in Scheme 6.

Benzothiophene 26 may be synthesized from the corresponding aldehyde 26b in a manner similar to that outlined in Scheme 6 for benzofuran 23. Benzothiophene 26b can be prepared by the oxidative cyclization (using an alkaline solution of potassium ferricyanide) of appropriately substituted o-mercaptocinnamic acid 26a [C. Chmelewsky and P. Friedlander, *Chem. Ber.*, 46, 1903 (1913)]. (For general methods of synthesis of benzothiophene, See, E. Champaigne in *Comprehensive Heterocyclic Chemistry*, vol. 4, Chapter 3–15; Eds. A. Katritzky and C. W. Rees.)

Scheme 6

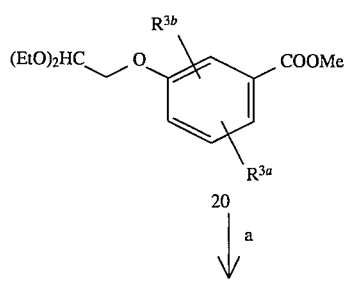

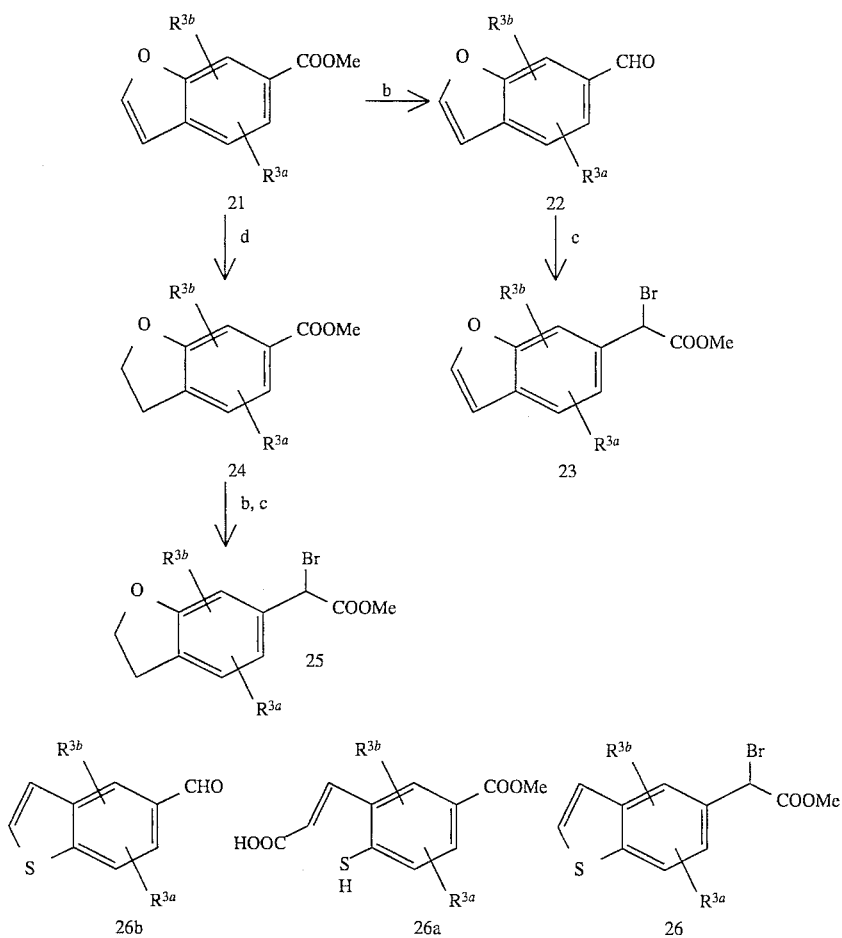

a. ZnCl₂
b. DIBALH, toluene
c. (i) CHCl₃, KOH, DMF, 0° C.;
   (ii) NaOH, DME/H₂O;
   (iii) HCl/MeOH;
   (iv) CBr₄/Ph₃P, CH₂Cl₂;
d. Ra—Ni/H₂

Scheme 7 outlines a typical synthesis of α-bromoarylacetates, 30 and 32, bearing appropriately substituted methylenedioxy or 1,4-dioxane rings. The substituted catechol derivative 27 is treated with an appropriate dibromide (where m is 1 or 2) in the presence of cesium carbonate in dimethylformamide to provide 28. Treatment of 28 with DIBALH yields the aldehyde 29 which is then transformed into the desired alkyl bromide as described.

Scheme 7

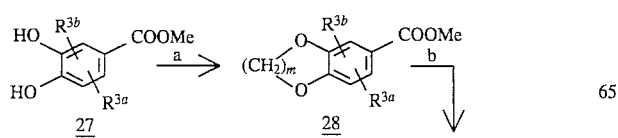

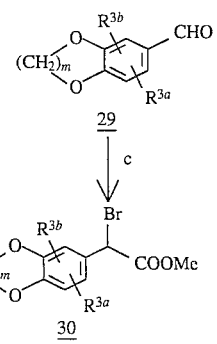

a. Br—(CH₂)ₘ—Br, Cs₂CO₃, DMF
b. DIBALH, toluene
c. (i) CHCl₃, KOH, DMF, 0° C.; (ii) NaOH, DME/H₂O;
   (iii) HCl/MeOH; (iv) CBr₄/Ph₃P, CH₂Cl₂;
d. NBS, AIBN, CCl₄

47
-continued
Scheme 7

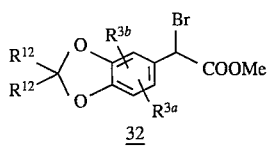

Following the general procedure described in Scheme 7 ethyl α-bromo-3,4-methylenedioxyphenylacetate, 30c can be prepared. The synthetic route for preparing this compound is specifically described below:

Scheme 7

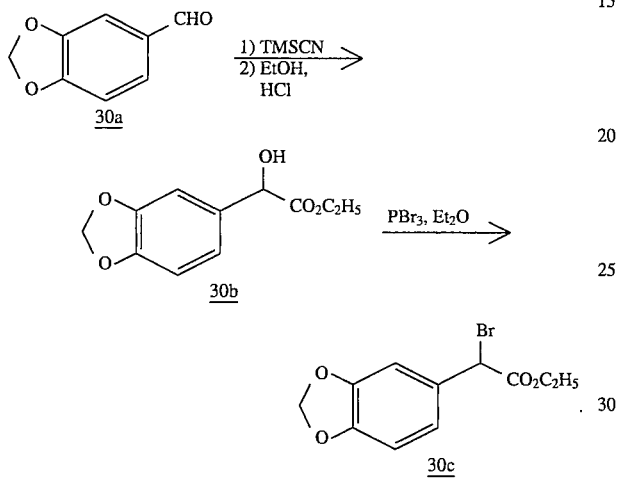

The compounds of Formula IV, wherein $R^1$ and $R^2$ represent a methylenedioxy group and Z represents an acylsulfonylamide, such as a 4-isopropylbenzensulfonamide, 34 which is prepared as described below using the commercially available sulfonylchloride, 33.

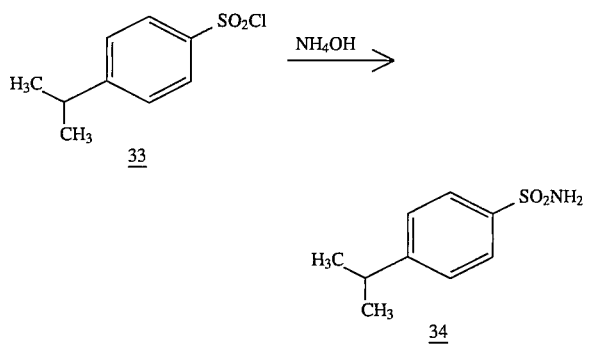

Following the procedure outlined in Scheme 8 below N-(4-iso-propylbenzenesulfonyl)-α-(4-carboxy-2-n-propylphenoxy)-3,4-methylenedioxyphenylacetamide, 38 is prepared. The methyl 4-hydroxy- 3-n-propylbenzoate was O-alkylated with ethyl α-bromo-3,4-methylenedioxyphenylacetate using potassium carbonate in acetone at reflux to give the diester 35. Under controlled conditions (typically at room temperature for a few minutes), selective saponification of 35 with excess sodium hydroxide in aqueous methanol yields the monoester 36. This is condensed with the acylsulfonamide, such as the 4-isopropylbenzensulfonamide, 34. One such coupling method is by formation of the acyl imidazolide via 1,1'-carbonyldiimidazole (CDI) and then reaction with the sulfonamide in the presence of 1,8-diazobicyclo-[5.4.0]undec-7ene (DBU), preferrably in THF at about 60° C. Another method is to form a mixed anhydride, for example, by reaction of 36 with pivaloyl chloride in the presence of triethylamine, in THF at –78° C., and then react this with the sulfonamide in the presence of a base such as lithium bis(trimethylsilyl)amide in THFDMSO at 0°–20° C. to give the acyl sulfonamide 37. The methyl ester of 37 is saponified with excess NaOH or KOH in aqueous methanol at 60° C. Acidification yields the carboxylic acid 38..

Scheme 8

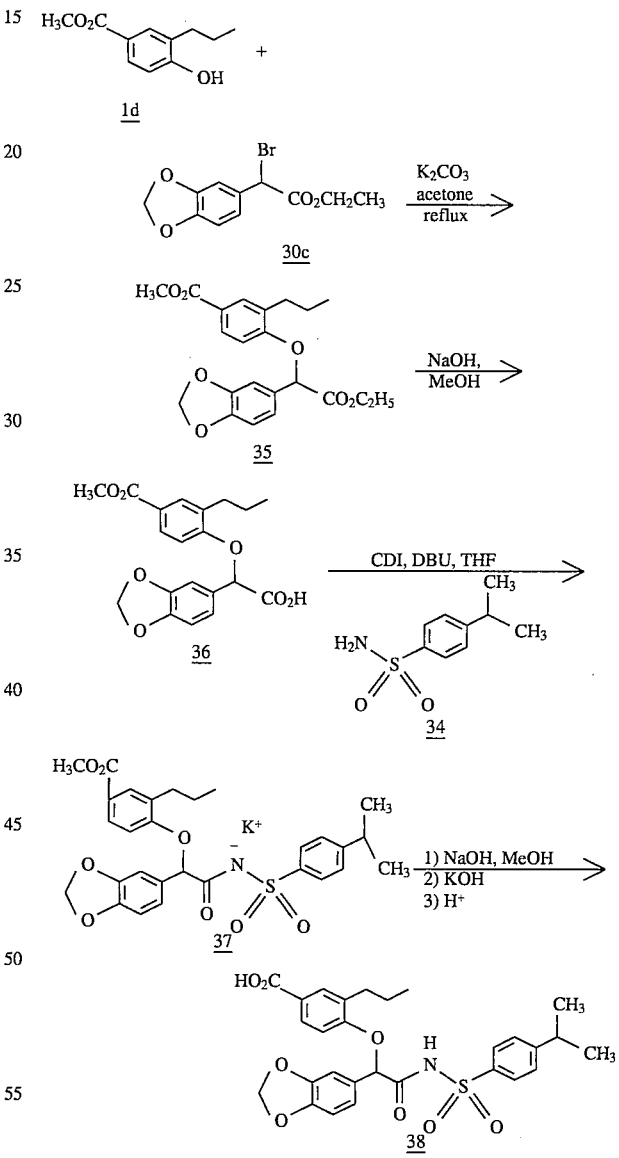

Scheme 9 generally describes the final step in the preparation of compounds of Formula I. Treatment of the free acid it with CDI in THF at 60° C. yields the acyl imidazolide, which is reacted in situ with the amine, $HNR^7(CH_2)_p$—E—$R^{16}$ in the presence of a base such as triethylamine in a solvent such as THF, acetonitrile or a THF-acetonitrile mixture at about 60°–80° C. to give the amide I.

Scheme 9

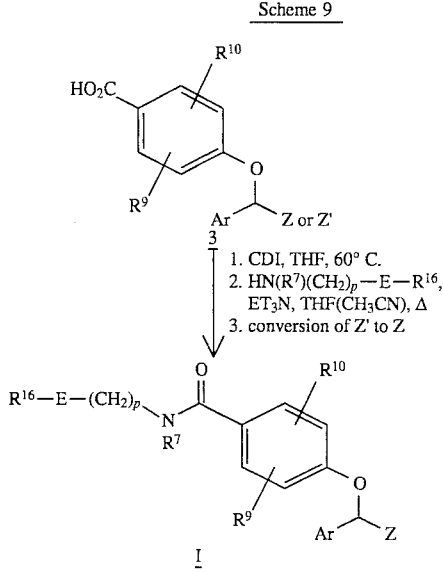

Scheme 10 describes the preparation of amides of Formula I starting with the free acid compound 38, N-(4-isopropylbenzenesulfonyl)-α-(4-carboxy-2-n-propylphenoxy)-3,4-methylenedioxyphenylacetamide.

Scheme 10

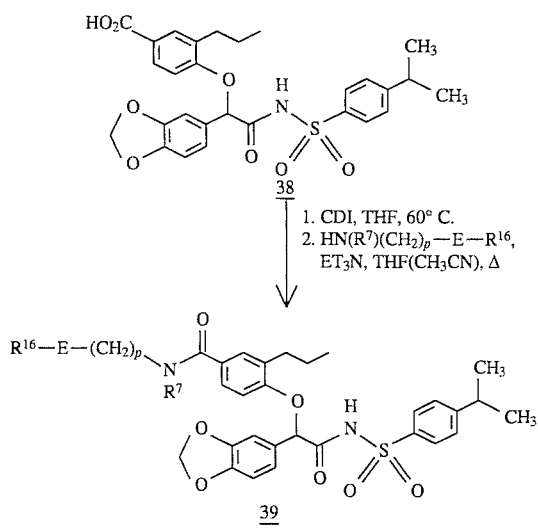

The compounds useful in the novel method treatment of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine salts, salts with amino acids like arginine, lysine, and the like. Also, salts with organic and inorganic acids may be prepared; e.g., HCl, HBr, $H_2SO_4$, $H_3PO_4$, methanesulfonic, toluenesulfonic, maleic, fumaric, camphorsulfonic.

The salts can be formed by conventional means, such as by reacting the free acid or free base forms of the product with one or more equivalent of the appropriate base or acid in a solvent or medium in which the salt is insoluble, or in a solvent such as water which is then removed in vacuo or by freeze-drying or by exchanging the cations of an existing salt for another cation on a suitable ion exchange resin.

It will be appreciated that the compounds of general Formula I in this invention may be derivatised at functional groups to provide prodrug derivatives which are capable of conversion back to the parent compounds in vivo. The concept of prodrug administration has been extensively reviewed (e.g. A. A. Sinkula in *Annual Reports in Medicinal Chemistry*, Vol 10, R. V. Heinzelman, Ed., Academic Press, New York London, 1975, Ch. 31, pp. 306–326, H. Ferres, *Drugs Of Today*, Vol 19, 499–538 (1983) and *J. Med. Chem,* 18, 172 (1975)). Examples of such prodrugs include the physiologically acceptable and metabolically labile ester derivatives, such as lower alkyl (e.g. methyl or ethyl esters), aryl (e.g. 5-indanyl esters), alkenyl (e.g. vinyl esters), alkoxyalkyl (e.g. methoxymethyl esters), alkylthioalkyl (e.g. methylthiomethyl esters), alkanoyloxyalkyl (e.g. pivaloyloxymethyl esters), and substituted or unsubstituted aminoethyl esters (e.g. 2-dimethylaminoethyl esters). Additionally, any physiologically acceptable equivalents of the compounds of general Formula I, similar to the metabolically labile esters, which are capable of producing the parent compounds of general Formula I in vivo, are within the scope of this invention.

It will be further appreciated that the majority of compounds of general Formula I claimed herein are asymmetric and are produced as racemic mixtures of enantiomers and that both the racemic compounds and the resolved individual enantiomers are considered to be within the scope of this invention. The racemic compounds of this invention may be resolved to provide individual enantiomers utilizing methods known to those skilled in the art of organic synthesis. For example, diastereoisomer salts, esters or imides may be obtained from a racemic compound of general Formula I and a suitable optically active amine, amino acid, alcohol or the like. The diastereoisomer salts, esters or imides are separated and purified, the optically active enantiomers are regenerated and the preferred enantiomer is the more potent isomer. The resolved enantiomers of the compounds of general Formula I, their pharmaceutically acceptable salts and their prodrug forms are also included within the scope of this invention.

Endothelin (ET-1), and two closely related bioactive peptides, ET-2 and ET-3, are widely distributed in mammalian tissues, and they can induce numerous biological responses in non-vascular as well as vascular tissues by binding to at least two distinct endothelin receptor subtypes. In addition to cardiovascular smooth muscle, neural and atrial sites, endothelin receptors may also be found in brain, gastrointestinal, kidney, lung, urogenital, uteral and placental tissues.

Endothelin is a potent vasoconstrictor peptide and thus plays a role in vivo in arterial pressure-volume homeostasis. Not only peripheral, but coronary vascular resistance as well, is increased by endothelin; cardiac output is decreased, while plasma renin activity is increased. Them is a reduction in renal blood flow and glomerular filtration ram, while levels of atrial natriuretic factor, vasopressin, and aldosterone become elevated.

It is also considered, in accordance with the present invention, that antagonists for the endothelin receptor may be useful in preventing or reducing restenosis subsequent to denudation following angioplasty. Such denudation results in myointimal thickening following angioplasty, due to increased endothelin release. Endothelin acts as a growth factor with respect to smooth muscle and fibroblastic cells, and possibly other types of cells, as well.

Endothelin is also a neuropeptide, acting on the posterior pituitary, where it modulates the release of the neurosecretory hormones vasopressin and oxytocin. Endothelin released from the posterior pituitary also acts as a circulating hormone, having a wide range of actions as discussed further above. This includes effects on the endocrine system, especially the adrenal glands. Endothelin increases plasma levels of epinephrine.

Consequently, the novel compounds of the present invention, which are receptor antagonists of endothelin, have therapeutic usefulness in preventing, decreasing or modulating the various physiological effects of endothelin discussed above, by wholly or partially blocking access of endothelin to its receptor.

Endothelin Receptor Binding Assays

The binding of the novel compounds of this invention to the endothelin receptor was determined in accordance with the assay described in detail immediately below. It is similar to the assay described in Ambar et al. (1989) *Biochem. Biophys. Res. Commun,* 158, 195–201; and Khoog et at. (1989) *FEBS Letters,* 253, 199–202.

The endothelins (ETs) have a number of potent effects on a variety of cells, and exert their action by interacting with specific receptors present on cell membranes. The compounds described in the present invention act as antagonists of ET at the receptors. In order to identify ET antagonists and determine their efficacy in vitro, the following three ligand receptor assays were established.

Receptor binding assay using cow aorta membrane preparation:

Thoracic aortae were obtained from freshly slaughtered calves and brought to the lab on wet ice. The adventitia were removed, and the aorta was opened up lengthwise. The lumenal surface of the tissue was scrubbed with cheesecloth to remove the endothelial layer. The tissue was ground in a meat grinder, and suspended in ice-cold 0.25M sucrose, 5 mM tris-HCl, pH 7.4, containing 0.5 mg/mL leupeptin and 7 mg/mL pepstatin A. Tissue was homogenized twice and then centrifuged for 10 minutes at 750×g at 4° C. The supernatant was filtered through cheesecloth and centrifuged again for 30 minutes at 48,000×g at 4° C. The pellet thus obtained was resuspended in the buffer solution described above (including the protease inhibitors), and aliquots were quick-frozen and stored at −70° C. until use. Membranes were diluted into 50 mM potassium phosphate (KPi), 5 mM EDTA pH 7.5 containing 0.01% human serum albumin. Assays were done in triplicate. Test compounds and 100 pM [$^{125}$I]-endothelin-1 (2000–2200 Ci/mmole, obtained from New England Nuclear or Amersham) were placed in a tube containing this buffer, and the membranes prepared above were added last. The samples were incubated for 60 min at 37° C. At the end of this incubation, samples were filtered onto prewetted (with 2% BSA in water) glass fiber filter pads and washed with 150 mM NaCl, 0.1% BSA. The filters were assayed for $^{125}$I radioactivity in a gamma counter. Nondisplaceable binding of [$^{125}$I]-endothelin-1 is measured in the presence of 100 nM unlabelled endothelin-1 [Endothelin-1 (ET-1) was purchased from Peptides International (Louisville, Ky.). $^{125}$I-ET-1 (2000 Ci/mMol) was purchased from Amersham (Arlington Heights, Ill.)]. Specific binding is total binding minus nondisplaceable binding. The inhibitory concentration (IC$_{50}$) which gives 50% displacement of the total specifically bound [$^{125}$I]-endothelin-1 was presented as a measure of the efficacy of such s compounds as ET antagonists.

Receptor binding assay using rat hippocampal membrane preparation:

Rat hippocampi were obtained from freshly sacrificed male Sprague-Dawley rats and placed in ice cold 0.25M sucrose, 5 mM tris-HCl, pH 7.4 containing 0.5 mg/mL leupeptin, 7 mg/mL pepstatin A. Hippocampi were weighed and placed in a Dounce homogenizer with 25 volumes (wet weight to volume) ice-cold sucrose buffer in the presence of protease inhibitors. Hippocampi were homogenized using a Dounce (glass-glass) homogenizer with type A pestle, with homogenizer in ice. Tissue homogenate was centrifuged at 750×g for 10 min at 4° C. Supernatant was filtered through dampened cheesecloth, and centrifuged again at 48,000×g for 30 min at 4° C. Pellets were resuspended in sucrose buffer with protease inhibitors. Aliquots of this preparation were quick frozen and stored at −70° C. until use. Membranes were diluted into 50 mM KPi, 5 mM EDTA pH 7.5 containing 0.01% human serum albumin. Assays were done in triplicate. Test compounds and 25 pM [$^{125}$I]-endothelin-1 (2000–2200 Ci/mmole, obtained from New England Nuclear or Amersham) were placed in a tube containing this buffer, and the membranes prepared above were added last. The samples were incubated for 60 min at 37° C. At the end of this incubation, samples were filtered onto prewetted (with 2% BSA in water) glass fiber filter pads and washed with 150 mM NaCl, 0.1% BSA. The filters were assayed for $^{125}$I radioactivity in a gamma counter. Nondisplaceable binding of [$^{125}$I]-endothelin-1 is measured in the presence of 100 nM unlabelled endothelin-1 [Endothelin-1 (ET-1) was purchased from Peptides International (Louisville, Ky.). $^{125}$I-ET-1 (2000 Ci/mMol) was purchased from Amersham (Arlington Heights, Ill.)]. Specific binding is total binding minus nondisplaceable binding. The inhibitory concentration (IC$_{50}$) which gives 50% displacement of the total specifically bound [$^{125}$I]-endothelin-1 was presented as a measure of the efficacy of such compounds as endothelin antagonists.

Receptor binding assay using cloned human ET receptors expressed in Chinese Hamster Ovary Cells:

Both endothelin receptor subtypes were cloned from a human cDNA library and were individually expressed in Chinese Hamster Ovary cells. Cells were harvested by addition of 126 mM NaCl, 5 mM KCl, 2 mM EDTA, 1 mM NaH$_2$PO$_4$, 15 mM glucose, 10 MM tris/HEPES pH 7.4 Cells were centrifuged at 250× g for 5 minutes. The supernatant was aspirated off, and the cells were resuspended in the 50 mM KPi, 5 mM EDTA pH 7.5 containing 0.01% human serum albumin. Assays were done in triplicate. Test compounds and 25–100 pM [$^{125}$I]-endothelin-1 (2000–2200 Ci/mmole, obtained from New England Nuclear or Amersham) were placed in a tube containing 50 mM KPi, 5 mM EDTA pH 7.5 containing 0.01% human serum albumin, and the cells prepared above were added last. The samples were incubated for 60 min at 37° C. At the end of this incubation, samples were filtered onto prewetted (with 2% BSA in water) glass fiber filter pads and washed with 150 mM NaCl, 0.1% BSA.

The filters Were assayed for $^{125}$I radioactivity in a gamma counter. Nondisplaceable binding of [$^{125}$I]-endothelin-1 is measured in the presence of 100 nM unlabelled endothelin-1 [Endothelin-1 (ET-1) was purchased from Peptides International (Louisville, Ky.). $^{125}$I-ET-1 (2000 Ci/mMol) was purchased from Amersham (Arlington Heights, Ill.)]. Specific binding is total binding minus nondisplaceable binding. The inhibitory concentration (IC$_{50}$) which gives 50% displacement of the total specifically bound [$^{125}$I]-endothelin-1 was presented as a measure of the efficacy of such compounds as endothelin antagonists.

The binding assays described above were used to evaluate the potency of interaction of representative compounds of the invention with endothelin receptors. To determine whether these compounds were endothelin antagonists, assays which measure the ability of the compounds to inhibit endothelin-stimulated phosphatidylinositol hydrolysis were established. Rat uterus contains predominantly one of the known endothelin receptor subtypes ($ET_A$).

Phosphatidylinositol hydrolysis assays using rat uterine slices:

Diethylstilbestrol primed female Sprague-Dawley rats were sacrificed and their uteri were collected, dissected of fat and connective tissue and minced. Minced tissue was added to oxygenated (95% $O_2$, 5% $CO_2$) 127 mM NaCl, 25 mM $NaHCO_3$, 10 mM Glucose, 2.5 mM KCl, 1.2 mM $KH_2PO_4$, 1.2 mM $MgSO_4$, 1.8 mM $CaCl_2$. To the tissue mince, 1.2 mM myo-[$^3$H]-inositol (Amersham) was added. The mince was incubated 90 min at 37° C., with constant oxygenation. After incubation, the loaded tissue mince was washed five times with the same oxygenated buffer to remove excess radiolabelled inositol. The tissue mince was resuspended in the above buffer, containing 10 mM LiCl, aliquotted into tubes, and 3 nM endothelin-1 with and without test compounds was added to start the assay. Assays were done in quadruplicate. Samples were incubated at 37° C. under blowing $O_2$ in a hooded water bath for 30 minutes. Reaction was stopped by addition of trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 mL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of endothelin minus the values in the absence of endothelin (basal). Test sample values are the values in the presence of endothelin and test sample minus basal. Inhibitory concentration ($IC_{50}$) is the concentration of test compound required to give a sample activity of 50% of control value.

Sarafotoxin S6c is a member of the endothelin family which binds preferentially to one of the known endothelin receptor subtypes ($ET_B$).

Phosphatidylinositol hydrolysis assays using rat lung slices:

Male Sprague-Dawley rats were sacrificed and their lungs were collected, dissected of fat and connective tissue and minced. Minced tissue was added to oxygenated (95% $O_2$, 5% $CO_2$) 127 mM NaCl, 25 mM $NaHCO_3$, 10 mM glucose, 2.5 mM KCl, 1.2 mM $KH_2PO_4$, 1.2 mM $MgSO_4$, 1.8 mM $CaCl_2$. To the tissue mince, 1.2 µM myo-[$^3$H]-inositol was added. The mince was incubated 60 min at 37° C., with constant oxygenation. After incubation, loaded tissue mince was washed five times with the same oxygenated buffer to remove excess radiolabelled inositol. Tissue mince was resuspended in the above buffer, containing 10 mM LiCl, aliquotted into tubes, and 3 nM sarafotoxin S6c with and without test compounds was added to start the assay. Assays were done in quadruplicate. Samples were incubated at 37° C. under blowing $O_2$ in a hooded water bath for 30 minutes. Reaction was stopped by addition of 0.5 mL 18% trichloroacetic acid to concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 mL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of sarafotoxin minus the values in the absence of sarafotoxin (basal). Test sample values are the values in the presence of sarafotoxin and test sample minus basal. Inhibitory concentration ($IC_{50}$) is the concentration of test compound required to give a sample activity of 50% of control value.

Phosphatidylinositol hydrolysis assays using cloned human endothelin receptors expressed in Chinese Hamster Ovary cells:

Endothelin receptors of both receptor subtypes were cloned from a human cDNA library and were individually expressed in Chinese Hamster Ovary cells. Cells were loaded overnight by the addition of 1.2 µm myo-[$^3$H]-inositol to their growth medium. Cells were harvested by addition of 126 mM NaCl, 5 mM KCl, 2 mM EDTA, 1 mM $NaH_2PO_4$, 15 mM glucose, 10 mM tris/HERPES pH 7.4. Cells were washed five times by centrifugation at 250×g for 5 minutes to remove excess radiolabelled inositol. The supernatant was aspirated off, and the cells were resuspended in the same oxygenated (95% $O_2$, 5% $CO_2$) buffer containing 10 mM LiCl, aliquotted into tubes, and 0.3 nM endothelin-1 with and without test compounds was added to start the assay. Assays were done in quadruplicate. Samples were incubated at 37° C. under blowing $O_2$ in a hooded water bath for 30 minutes. Reaction was stopped by addition of 0.5 mL 18% trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 mL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of endothelin minus the values in the absence of endothelin (basal). Test sample values are the values in the presence of endothelin and test sample minus basal. Inhibitory concentration. ($IC_{50}$) is the concentration of test compound required to give a sample activity of 50% of control value.

Using the methodology described above, representative compounds of the invention were evaluated and found to exhibit $IC_{50}$ values of at least <50 µM thereby demonstrating and confirming the utility of the compounds of the invention as effective endothelin antagonists.

Methodology for determining whether an ET-1 selective antagonist could inhibit the ET-1 mediated prostatic urethral contractions in a mongrel dog model:

On separate days, two fasted male mongrel dogs (HRP, Inc.) weighing 11.0 and 12.4 kg, were anesthetized with Sodium Pentobarbital (Steris Laboratories, Inc.) at 35 mg/kg (i.v.) to effect, followed by 4 mg/kg/hr (i.v.) infusion. A cuffed endotracheal tube was inserted and each animal was ventilated with room air using a positive displacement large animal ventilator (Harvard Apparatus) at a rate of 18 breaths/minute and an average tidal volume of 18 ml/kg body weight. Body temperature was maintained with a heating pad and heat lamp using a temperature controller (YSI) and esophageal probe. Two catheters (PE 260) were., placed in the aorta via the femoral arteries (one in each artery) for administration of endothelin or phenylephrine and for continuous direct monitoring of blood pressure and heart rate using a Statham blood pressure transducer (Spectramed) and a computer system (Modular Instruments, Inc.). Two other catheters (PE 260) were placed in the vena cava via the femoral veins (one catheter in each vein) for administration of pentobarbital and an ET-1 selective endothelin antagonist of Formula I. A supra-pubic incision approximately one-half inch lateral to the penis was made to expose the ureters, urinary bladder, prostate, and urethra. The dome of the bladder was retracted to facilitate dissection of the ureters. The ureters were cannulated with PE 90 and tied off to the bladder. Umbilical tape was passed beneath the urethra at the bladder neck and another piece of tape was placed approximately 1–2 cm. distal to the prostate. The bladder dome was incised and a Micro-tip® catheter transducer (Millar Instruments, Inc.) was advanced into the urethra. The neck of the bladder was ligated with the umbilical tape to hold the transducer. The bladder incision was sutured with 3-0 silk (purse string suture). The transducer was withdrawn until it was positioned in the prostatic urethra. The position of the Micro-tip® catheter was verified by gently squeezing the prostate and noting the large change in urethral pressure prior to lighting the distal urethra.

Experimental Protocol:

Phenylephrine (PE) (10 µg/kg, intra-arterial) was t3 administered and pressor effects on diastolic blood pressure (DBP) and intra-urethral pressure (IUP) were noted. When blood pressure returned to baseline, endothelin-1 (ET-1) (1 nmole/kg, intra-arterial) was administered. Changes in DBP and IUP were monitored for one hour and an ET-1 selective endothelin antagonist, such as a compound of Formula I (30 mg/kg, intra-venous) was administered. Ten to fifteen minutes later when blood pressure had stabilized, ET-1 was administered again, and inhibition of ET-1 induced effects were noted. PE was administered at the end of the experiment to verify specificity for ET-1 blockade. The dogs were euthanized with an overdose of pentobarbital followed by saturated KCl.

The drugs utilized in the experiment described above were:

1) Phenylephrine, HCl (PE) (Sigma Chemical, Co.) was given at a volume of 0.05 mL/kg;
2) Endothelin-1 (ET-1) (Human, Porcine, Canine, Rat, Mouse, Bovine) (Peninsula Laboratories, Inc.) was given at a volume of 0.05 mL/kg;
3) ET-1 selective antagonist, such as a compound of Formula I, was given at a volume of 0.3 mL/kg.

All drugs were dissolved in isotonic saline solution.

ET-1 causes constriction of the prostatic urethra, as well as a complex hemodynamic response comprised of an initial depressor and subsequent pressor response in anesthestized dogs. The hemodynamic and prostatic urethral responses to ET-1 are specifically inhibited by an ET-1 selective endothelin antagonist. The efficacy of an endothelin antagonist in inhibiting the prostatic urethral pressor effect of ET-1 suggests that selective antagonists of ET-1 will be useful in the treatment of urinary obstruction in benign prostatic hyperplasia.

In Situ Rat Prostate:

Male Sprague-Dawley rats (Taconic Farms) weighing 300–400 grams were anesthetized with urethane (1.75 g/kg, ip), a tracheal cannula was inserted, and the femoral artery was cannulated. Core body temperature was maintained at 37+0.5 ° C. A 4–5 cm midline abdominal incision was made m expose the bladder and prostate. The prostate was separated from the bladder and surrounding capsule by blunt dissection with a forcep. A length of surgical silk was gently secured around the anterior tips of the prostate lobes. A second length of surgical silk attached to an atraumatic needle was passed through and tied to the base of the prostate approximately 10–12 mm posterior to the first tie. The posterior ligature was secured to an anchor post whereas the anterior ligature was connected to a Grass FT03 transducer (Grass Instruments, Quincy, Mass.) and maintained at a tension of 1 g. Signals from the transducer were amplified and recorded on a polygraph (Hewlett-Packard 8805B amplifiers and 7758A recorder, Palo Alto, Calif.). After equilibrating for approximately 15 min, the rats were administered pretreatment drugs (atropine 1 mg/kg, (+) propranolol 1 mg/kg) 10 min apart through the intra-arterial (IA) cannula. Thirty minutes later, ET-1 (0.3 nmoles/kg) was injected intra-arterial every thirty minutes for a total of three times. Five minutes before the third injection of ET-1, vehicle with or without an endothelin antagonist was injected IA. The response of the prostate to ET-1 was quantified by measuring the change ($\Delta$) from baseline tension to the peak of the response during the 5-minute period after the third ET-1 injection.

The in situ rat postate protocol is utilized to determine the antagonist activity and potency of compounds of this invention to block the direct contractile effects of ET-1 on the rat prostate in vivo. In this protocol, an ET-1 selective endothelin antagonist demonstrated to cause a specific inhibition of ET-1 to contract the prostate, will be useful in the treatment of urinary obstruction in benign prostatic hyperplasia.

Accordingly the novel compounds of the present invention are useful in human therapy for treating asthma, hypertension, renal failure particularly post-ischemic renal renal, cyclosporin nephrotoxicity, vasospasm, cerebral and cardiac ischemia, myocardial infarction, or endotoxin shock caused by or associated with endothelin, by administration to a patient in need of such treatment of a therapeutically effective amount thereof.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the an will recognize, the dosage range will generally be about 0.5 mg to 1.0 g. per patient per day which can be administered in single or multiple doses. Preferably, the dosage range will be about 0.5 mg to 500 mg. per patient per day; more preferably about 0.5 mg to 200 mg. per patient per day.

The compounds of this invention can also be administered in combination with $A_2$-adrenosine receptor agonists, α-adrenergic antagonists, angiotensin II antagonists, angiotensin convening enzyme inhibitors, β-adrenergic antagonists, atriopeptidase inhibitors (alone or with ANP), calcium channel blockers, diuretics, potassium channel agonists, renin inhibitors, sertonin antagonists, sympatholytic agents, as well as other antihypertensive agents. For example, the compounds of this invention can be given in combination with such compounds as A-69729, FK 906, FK 744, UK-73900, CSG 22492C, amiloride, atenolol, atriopeptin, bendroflumethiazide, chlorothalidone, chlorothiazide, clonidine, cromakalin, cryptenamine acetates and cryptenamine tannates, deserpidine, diazoxide, doxazosin, guanabenz, guanethidine, guanethidine sulfate, hydralazine hydrochloride, hydrochlorothiazide, isradipine, ketanserin, losartan, metolazone, metoprolol, metoprolol tartate, methyclothiazide, methyldopa, methyldopate hydrochloride, minoxidil, nadolol, pargyline hydrochloride, pinacidil, pindolol, polythiazide, prazosin, propranolol, rauwolfia serpentina, rescinnamine, reserpine, sodium nitroprusside, spironolactone, terazosin, timolol maleate, trichlormethiazide, trimethophan camsylate, verapamil, benzthiazide, quinethazone, ticrynafan, triamterene, acetazolamide, aminophylldine, cyclothiaide, ethacrynic acid, furosemide, merethoxylline procaine, sodium ethacrynate, captopril, delapfil hydrochloride, enalapril, enalaprilat, fosinopril sodium, lisinopril, pentopril, quinapril, quinapril hydrochloride, ramapril, teprotide, zofenopril, zofenopril calcium, diflusinal, diltiazem, felodipine, nicardipine, nifedipine, niludipine, nimodipine, nisoldipine, nitrendipine, and the like, as well as admixtures and combinations thereof. Combinations useful in the management of congestive heart failure include, in addition, compounds of this invention with cardiac stimulants such as dobutamine and xamoterol and phosphodiesterase inhibitors including amrinone and milrinone.

Typically, the individual daily dosages for these combinations can range from about one-fifth of the minimum recommended clinical dosages to the maximum recommended levels for those entities given singly. To illustrate these combinations, one of the endothelin antagonists of this invention effective clinically at a given daily dose range can be effectively combined, at levels which are less than that daily dose range, with the following compounds at the indicated per day dose range: hydrochlorothiazide (6–100 mg), chlorothiazide (125–500 mg), furosemide(5–80 mg), ethacrynic acid (5–200 mg), amiloride (5–20 mg), diltiazem(30–540 rag), felodipine(1–20 mg), nifedipine(5–12 mg), nitrendipine(5–60 mg), timolol maleate (1–20 mg), propanolol (10–480 mg), and methyldopa($^{125-2000}$ mg). In addition triple drug combinations of hydrochlorothiazide(6–100 mg) plus amiloride (5–20 mg) plus endothelin antagonists of this invention, or hydrochlorothiazide(6–100 mg) plus timolol maleate (1–20 mg) plus endothelin antagonists of this invention, or hydrochlorothiazide(6–100 mg) plus nifedipine (5–60 mg) plus endothelin antagonists of this invention are effective combinations to control blood pressure in hypertensive patients. Naturally, these dose ranges can be adjusted on a unit basis as necessary to permit divided daily dosage and the dose will vary depending on the nature and severity of the disease, weight of the patient, special diets and other factors.

The present invention also relates to pharmaceutical compositions for treating asthma, hypertension, renal failure, particularly post-ischemic renal failure, cyclosporin nephrotoxicity, vasospasm, cerebral and cardiac ischemia, benign prostatic hyperplasia, myocardial infarction, or endotoxin shock caused by or associated with endothelin, comprising a therapeutically effective amount of the novel compound of this invention together with a pharmaceutically acceptable carrier therefor.

About 0.5 mg to 1.0 g. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as cornstarch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage uniform is a capsule, it may contain, in addition to materials of the above type, a liquid carder such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of Formula I and their incorporation into pharmaceutical compositions and as such are not to be considered as limiting the invention set forth in the claims appended hereto.

EXAMPLE 1

Methyl 3-allyl-4-hydroxybenzoate
Step A: Preparation of methyl 4-allyloxybenzoate To a nitrogen flushed 5 L three neck round bottom flask fitted with a mechanical stirrer, condenser, and a nitrogen inlet was charged 608 g (4 mol of methyl 4-hydroxybenzoate, 520 ml (727 g, 6.00 mol, 1.5 eq) of allyl bromide, 663 g (9.6 mol of anhydrous potassium carbonate, and 2.3 L of acetone. The mixture was refluxed with vigorous stirring for 90 min. Additional potassium carbonate, (50 g) was added, and 25 g added again after an additional 50 min. After 20 min (total reaction time of 160 min), the suspension was allowed to cool to ambient temperature and stirred overnight. The mixture was filtered and the cake washed with 3 L of acetone. The solution was concentrated to obtain 788.6 g (theoretical yield 768.9 g) of a pale yellow, almost colorless oil which was used without purification in the next step. The product was a single spot on TLC (silica-1:1 EtOAc/Hex) and the NMR was consistent with methyl 4-allyloxybenzoate.

Step B: Preparation of methyl 3-allyl-4-hydroxybenzoate

To a nitrogen flushed magnetically stirred 3 L single neck round bottom flask fitted with a condenser, and a nitrogen inlet was charged the methyl 4-allyloxybenzoate, 400 mL of 1,2-dichlorobenzene, and 10 g of BHT. The solution was heated and distillate collected until the head temperature reached that of 1,2-dichlorobenzene (180° C. The solution was then refluxed for 6.5 hr, then cooled to 140° C. and aged overnight. The hot solution was then poured into 2.5 L of hexanes and the resulting suspension aged overnight with stirring. The suspension was filtered, and the cake washed with hexanes. The solid was air dried affording 747.7 g (97.3% yield) as a white solid having a faint odor of o-dichlorobenzene.

$^1$H-NMR (300 MHz, CDCl$_3$, ppm): δ3.42 (dt J=6.4,1.4 Hz, 2H), 3.87 (s, 3H), 5.11–5.18 (m, 2H), 5.87 (bs, 1H), 5.93–6.06 (m, 1H), 6.83 (d, J=7.9 Hz, 1H), 7.79–7.85 (m, 2H).

EXAMPLE 2

Methyl 4-hydroxy-3-n-propylbenzoate

Step A: Preparation of methyl 4-hydroxy-3-n-propylbenzoate

A solution of 363 g of methyl 3-allyl-4-hydroxybenzoate in 1.5 L of methanol was hydrogenated for 1 hr in a Parr® type shaker at 40 psi and ambient temperature using 1.5 g of 10% palladium on Carbon as the catalyst. The reaction was filtered through Solka-Floc® and the cake washed with 1 L of methanol. The combined filtrate, was concentrated and the oil flushed with ether. Hexanes (1.5 L) were added and the resulting suspension cooled to 0° C. The product was collected by filtration, washed with hexanes and dried affording 176.6 g of methyl 4-hydoxy-3-n-propylbenzoate. A second crop of 166.4 g was obtained by concentrating the filtrate, diluting with hexanes and filtering, bringing the total to 343 g (94.3% yield).

$^1$H-NMR (300 MHz, CDCl$_3$, ppm): δ0.94 (t J=7.4 Hz, 3H), 1.63 (m, 2H), 2.59 (t J=7.7 Hz, 2H), 3.86 (s, 3H), 5.87 (s, 1H), 6.84 (d J=8.4 Hz 1H), 7.76 (dd J=8.4, 2.2 Hz, 1H), 7.81 (d J=2.2 Hz, 1H).

EXAMPLE 3

Ethyl 3,4-methylenedioxy-d,1-mandelate.

Step A: α-Trimethylsilyloxy-3,4-methylenedioxyphenylacetonitrile

To a nitrogen flushed magnetically stirred 3 L single neck round bottom flask fitted with a nitrogen inlet was charged 285 g (1.9 mol) of piperonal, 200 g (2.0 mol) of trimethylsilylcyanide, 0.2 g of potassium cyanide, 0.2 g of 18-crown-6 and 500 mL of methylene chloride. The mixture was stirred at ambient temperature for 75 min, during which time the reaction exothermed to 35° C. A second charge of 5 g of piperonal was added and the reaction stirred an additional 75 min. The reaction mixture was diluted with ether and 250 mL of saturated sodium bicarbonate solution was added. The mixture was stirred for 20 min before partitioning. The organic layer was washed with another 250 mL portion of saturated sodium bicarbonate, twice with brine (300 mL), dried with sodium surfate, filtered and concentrated, leaving 489.6 g (481.4 g theoretical yield) of the title compound as a pale yellow oil. This was used as is without purification in the next step.

Step B: Preparation of ethyl 3,4-methylenedioxy-d,1-mandelate

To a nitrogen flushed magnetically stirred 3 L single neck round bottom flask fitted with a gas inlet was charged the product obtained from the previous step and 1 L of absolute ethanol. The solution was cooled to 0° C. and HCl gas gently bubbled through the solution for 1 hr. After a few minutes the reaction solidified to a white mass which was aged at room temperature overnight. 1 L of methylene chloride, and 1 L of water were added. The mixture was shaken for ca. 5 min dissolving some of the white solid. The mixture was decanted and the procedure repeated several more times until all of the solid had been dissolved. The layers were separated and the aqueous layer back extracted once with methylene chloride. The combined organic layer was washed with brine, dried with magnesium sulfate and filtered through a pad of silica. The solution was concentrated, flushed with ether and diluted with hexanes. The white slurry was cooled to 0° C. then filtered. The cake was washed with 1:2 ether/hexanes followed by hexanes. The product was dried affording 347.2 g of the title compound as a white solid. A second crop of 24 g was obtained by concentrating the mother liquors, bringing the total to 371.4 g (85.8% yield).

$^1$H-NMR (300 MHz, CDCl$_3$, ppm): δ1.22 (t, J=7.2 Hz, 3H), 3.41.(d, J=5.6 Hz, 1H), 4.10–4.31 (m, 2H), 5.03 (d, J=5.6 Hz, 1H), 5.94 (s, 2H), 6.77 (d, J=8.5 Hz, 1H), 6.85–6.90 (m, 2H).

EXAMPLE 4

Ethyl α-bromo-3,4-methylenedioxyphenylacetate

Step A: Preparation of ethyl α-bromo-3,4-methylenedioxyphenylacetate

To a nitrogen flushed 5 L three neck round bottom flask fitted with a mechanical stirrer, a dropping funnel and a nitrogen inlet was charged 433.8 g (1.93 mol) of ethyl 3,4-methylenedioxy-d,1-mandelate and 3.5 L of ether. The suspension was cooled to 0°–5° C. and a solution of 179 g (0.66 mol) of PBr$_3$ in 500 mL of ether was added over a period of 30 min. The reaction was aged for 2.5 hr at 0°–5° C. during which time, an additional 24.2 g (0.09 mol) of PBr$_3$ was added. The solid initially present slowly dissolved leaving a clear yellow solution. The reaction was quenched by careful addition of 800 mL of saturated sodium bicarbonate solution and 200 mL of water. The layers were separated and the aqueous layer extracted once with ether. The combined organic phase was washed once with saturated sodium bicarbonate solution, 10% sodium bisulfite solution, brine, dried with magnesium sulfate, and filtered through a pad of silica. The solution was concentrated to 507.6 g (91.4% ) of a pale yellow oil. Essentially a single spot on TLC (silica-1:1 Et$_2$O/Hex), NMR indicated a small amount of ether was present. This was used as is without purification in the next step.

$^1$H-NMR (300 MHz, CDCl$_3$, ppm): δ1.27 (t, J=7.2 Hz, 3H), 4.10–4.35 (m, 2H), 5.26 (s, 1H), 5.96 (s, 2H), 6.72 (d, J=8. Hz, 1H), 6.94 (dd, J=8.0, 1.8 Hz, 1H), 7.11 (d, J=1.8 Hz, 1H).

EXAMPLE 5

α-(4-Carbomethoxy-2-n-propylphenoxy)-3,4-methylenedioxyphenylacetic acid sodium salt Step A: Preparation of ethyl α-(4-carbomethoxy-2-n-propylphenoxy)-3,4-methylenedioxyphenylacetate To a 2 L three necked 24/40 round bottom flask equipped with a mechanical stirrer, a nitrogen inlet and a dropping funnel was first added a solution of 36.0 g (0.185 mol) of methyl 4-hydroxy-3--n-propylbenzoate dissolved in 700 mL of anhydrous DMF followed by 66.4 g (0.204 mol) of cesium carbonate. The flask was purged with nitrogen and the reaction mixture was stirred at room temperature for 2 hours. A solution of 58.5 g (0.204 mol) of ethyl α-bromo-3,4-methylenedioxyphenylacetate dissolved in 100 mL of DMF was then added via an addition funnel over a 15 minute period. The reaction mixture was stirred an additional 1 hour at room temperature then quenched by addition to 5 L of a 5% aqueous citric acid solution. The organic product was extracted into diethylether (2×4 L), the organic layers were separated, washed with saturated aqueous NaCl, dried (MgSO$_4$), filtered, and evaporated. The residue was applied to a silica gel (2 kg; 70–230 mesh) column equilibrated in 10% CH$_2$Cl$_2$-hexane. The column was then eluted successively with 12 L of 10% CH$_2$Cl$_2$-hexane, 12 L of 5% EtOAc-hexane, 4 L of 7.5% EtOAc-hexane, 12 L of 10% EtOAc-hexane, and finally 8 L of 20% EtOAc-hexane. Combination of the purified fractions and evaporation in vacuo afforded 76.3 g (74.2 theoretical) of the title compound as a pale yellow oil which was used without further purification in the next step.

Step B: Preparation of α-(4-carbomethoxy-2-n-propylphenoxy)-3,4-methylenedioxyphenylacetic acid sodium salt A 1 L 3 necked 24/40 round bottom flask equipped with a mechanical stirrer, a dropping funnel, and a nitrogen inlet was charged with a solution of 76.3 g 0.185 mol) of the semi-purified product of Step A dissolved in 500 mL of methanol. The flask was purged with nitrogen, the stirrer was started, and 37 mL of a 5.0N aqueous solution of sodium hydroxide was added over a 30 minute period via an addition funnel. The reaction mixture was stirred at room temperature for an additional 30 minutes at which point TLC analysis (CH$_2$Cl$_2$-MeOH-NH$_4$OH 90:10:1) indicated that the starting material had been consumed. The reaction mixture was adjusted to pH=4 with 6N HCl, and the bulk of the organic solvent was removed in vacuo. The precipitated organic product and the aqueous layer were next partitioned between CH$_2$Cl$_2$ (1 L) and water (1 L) which produced a copious emulsion. The reaction mixture was then aged overnight in a refrigerator which resulted in crystallization of the organic product. The crystalline solid was separated from the two phase mixture by filtration and washed with CH$_2$Cl$_2$. The solid was slurried again in diethyl ether, filtered, washed with hexane, and then dried in a vacuum to afford 65 g (85.3%) of the title compound as a white crystalline solid.

$^1$H-NMR (400 MHz, CD$_3$OD, ppm): δ0.93 (t, J=7.2 Hz, 3H), 1.62–1.75 (m, 2H), 2.63–2.70 (m, 1H), 2.77–2.81 (m, 1H), 3.84 (s, 3H), 5.54 (s, 1H), 5.94 (s, 2H), 6.81 (d, J=7.6 Hz, 1H), 6.89 (d, J=9.2 Hz, 1H), 7.08 (d, J=1.6 Hz, 1H), 7.11 (br s, 1H), 7.78–7.81 (m, 2H).

Microanalysis for C$_{20}$H$_{20}$O$_7$Na$_{0.75}$·1.25 H$_2$O. Calc'd: C=58.29; H=5.50; Na=4.18 Found: C=58.19; H=5.17; Na=3.93

EXAMPLE 6

N-(4-iso-propylbenzenesulfonyl)-α-(4-carbomethoxy-2-n-propylphenoxy)-3,4-methylenedioxyphenylacetamide Step A: Preparation of ethyl α-(4-carbomethoxy-2-n-propylphenoxy)-3,4-methylenedioxyphenylacetate To a nitrogen flushed 5 L three neck round bottom flask fitted with a mechanical stirrer, condenser, and a nitrogen inlet was charged 326 g (1.68 mol) of methyl 4-hydoxy-3-n-propylbenzoate, 507.6 g (1.73 mol) of ethyl α-bromo-3,4-methylenedioxyphenylacetate from above, 235 g (1.70 mol) of anhydrous potassium carbonate, and 1.7 L of acetone. The mixture was refluxed with vigorous stirring for 9 hr. The suspension was allowed to cool to ambient temperature and stirred overnight. The mixture diluted with 2 L of ether, cooled to 0° C. and filtered through Super-Cel$^R$. The cake washed with ether and the combined filtrate concentrated. The residue was redissolved in ether and the organic layer washed with once with 1N HCl, saturated sodium bicarbonate solution, 10% sodium bisulfite solution, brine, dried with magnesium sulfate, treated with charcoal and filtered through a plug of silica. The pale yellow solution was concentrated to 697.3 g (theoretical 678 g) of a thick yellow oil which was used without purification in the next step. NMR was consistent with the title compound.

$^1$H-NMR (300 MHz, CDCl$_3$, ppm): δ0.95 (t, J=7.3 Hz, 3H), 1.17 (t, J=7.1 Hz, 3H), 1.61–1.81 (m, 2H), 2.63–2.80 (m, 2H), 3.85 (s, 3H), 4.07–4.23 (m, 2H), 5.58 (s, 1H), 5.96 (s, 2H), 6.71 (d, J=8.5 Hz, 1H), 6.76 (d, J=8.0 Hz, 1H), 7.02 (d,d, J=8.0, 1.7 Hz, 1H), 7.05 (d, J=1.7 Hz, 1H), 7.79 (d,d, J=8.5, 2.2 Hz, 1H), 7.84 (d, J=2.2 Hz, 1H).

Step B: Preparation of α-(4-carbomethoxy-2-n-propylphenoxy)-3,4-methylenedioxyphenylacetic acid.

To a nitrogen flushed 5 L 3 neck round bottom flask equipped with a mechanical stirrer, a dropping funnel, and a nitrogen inlet was charged with 697.3 g (1.68 mol) of the crude product of Step A and 2 L of methanol. 500 mL of 5.0N (1.5 eq) aqueous sodium hydroxide was added over a 20-minute period via an addition funnel. The reaction mixture was stirred at room temperature for an additional 1 hr at which point TLC analysis (CH$_2$Cl$_2$-MeOH-NH$_4$OH 90:10:1) indicated that the starting material had been consumed. The reaction mixture neutralized with 420 mL of 6N HCl, and the bulk of the organic solvent was removed in vacuo. The residue was dissolved in ether and extracted with a combination of aqueous NaOH and NaHCO$_3$. The aqueous layer was extracted with ether and the combined organic layer was washed with aqueous NaHCO$_3$. The aqueous layer was acidified with HCl and extracted with ether. The ether solution was dried with magnesium sulfate, filtered, and concentrated to afford 708.9 g (theoretical 625 g) of the title compound as a viscous orange oil. NMR indicated that it was ca. 85% product by weight (15% ether) thus providing a corrected yield of 602.6 g (96.4% yield)

$^1$H-NMR (300 MHz, CD$_3$OD, ppm): δ0.93 (t, J=7.4 Hz, 3H), 1.56–1.77 (m, 2H), 2.68 (t, 2H), 3.84 (s, 3H), 5.57 (s, 1H), 5.95 (s, 2H), 6.42 (bs, 1H), 6.71 (d, J=8.5 Hz, 1H), 6.79 (d, J=7.9 Hz, 1H), 6.99–7.05 (m, 2H), 7.78 (d,d, J=8.5, 2.2 Hz, 1H), 7.82 (d, J=2.2, 1H).

Step C: Preparation of N-(4-iso-propylbenzenesulfonyl)-α-(4-carbomethoxy-2-n-propylphenoxy)-3,4-methylenedioxyphenylacetamide potassium salt.

To a nitrogen flushed 5 L 3 neck round bottom flask equipped with a mechanical stirrer, a dropping funnel, a condenser and a nitrogen inlet was charged 1 L of THF and 350 g (2.16 mol, 1.42 eq) of carbonyl diimidazole (CDI). The mixture was heated to reflux and a solution of 663.6 g (1.52 mol of acid from Step B and 1 L of THF was added dropwise over a period of 30 min. The reaction was monitored for coversion of the acid to the acyl imidazolide by NMR. An additional 85 g of CDI was added over 45 min. The solution was cooled and 291 g (1.48 mol) 4-iso-propylbenzenesulfonamide was added as a solid in one portion and the solution aged 20 min. DBU 230 mL (234 g, 1.54 mol) was added dropwise over 10 min resulting in an exotherm to 45° C. The reaction was aged at room temperature for 3 hr then concentrated in vacuo. The residue was partitioned between 2.75 L of 2.5N HCl and 3 L of ether. The aqueous layer was extracted with 1 L of ether, and the combined organic layer washed with 2N HCl and saturated potassium bicarbonate solution. The ethereal layer was transferred to a 5 L 3 neck round bottom flask equipped with a mechanical stirrer. 1 L of aqueous potassium bicarbonate solution was added and the mixture stirred overnight at room temperature. The resulting thick suspension was filtered and the cake washed with 500 mL of water followed by 1 L of ether. The product was then slurried in the funnel with additional ether and sucked dry yielding 741 g of a tan solid The solid was recharged to a 5 L 3 neck round bottom flask equipped with a mechanical stirrer to which was added 1L of ethyl acetate and 500 mL of saturated potassium bicarbonate solution. The slurry was stirred at room temperature for 1 hr, diluted with 3 L of ether, and the slurried stirred at room temperature overnight. The product was filtered, washed with 500 mL of water and 1 L of ether and dried in vacuo. The yield was 592 g of the title compound as a white crystalline solid. A second crop of 47.6 g was obtained from the mother liqours bringing the total to 639.6 g (74% of theory)

$^1$H-NMR (300 MHz, CD$_3$OD, ppm): $\delta$0.88 (t, J=7.4 Hz, 3H), 1.21 (d, J=6.9 Hz, 6H), 1.52–1.66 (m, 2H), 2.50–2.76 (m, 2H), 2.90 (sept, J=6.9 Hz, 1H), 3.84 (s, 3H), 5.35 (s, 1H), 5.94 (s, 2H), 6.69 (d, J=8.6 Hz, 1H), 6.76 (d, J=8.5 Hz, 1H), 7.04 (m, 2H), 7.20 (d, J=, 8.4 Hz, 2H), 7.61 (dd, J=8.5, 2.20, Hz, 1H), 7.67 (d, J=8.4, 2H), 7.71 (d, J=2.1 Hz, 1H).

EXAMPLE 7

N-(4-iso-propylbenzenesulfonyl)-$\alpha$-(4-carboxy-2-n-propylphenoxy)-3,4-methylenedioxyphenylacetamide dipotassium salt Method A:

Step A: Preparation of N-(4-iso-propylbenzenesulfonyl)-$\alpha$-(4-carboxy-2-n-propylphenoxy)-3,4-methylenedioxyphenylacetamide dipotassium salt A mixture of 204 g (0.345 mol) of the product of Example 6, 420 mL of 1.0N KOH in methanol and 500 mL of water was stirred at 60° C. under a nitrogen atmosphere. After 3 hours TLC analysis (90:10:1 CH$_2$Cl$_2$-MeOH—NH$_4$OH) indicated that ester hydrolysis was complete. The reaction mixture was cool slightly, then concentrated on a rotary evaporator to a weight of 500 g. 2.5 L of isopropanol was added and the solution reconcentrated to an oil. The residue was flushed with an additional 2–3 L of isopropanol until crystallization began. The slurry was concentrated to ca. 1.5 L and cooled to 30° C., filtered and washed with 300 mL of IPA and 500 mL of ether. The product was dried affording 185 g of semi-pure title compound as a white crystalline solid. A second crop of 17 g was obtained from the filtrate after cooling. The material was recrystallized as follows: 168 g was dissolved in 3 L of absolute ethanol at reflux, filtered hot, and the flask and funnel rinsed with an additional 500 mL of ethanol. 70 mL of water was added and the solution cooled to 0° C. over 2 hr then aged at 0° C. for 6 hr. The product was collected by filtration, washed with ethanol, then air. The yield was 160.8 g of the title compound as a white crystalline solid.

$^1$H-NMR (400 MHz, CD$_3$OD, ppm): $\delta$0.88 (t, J=7.2 Hz, 3H), 1.21 (d, J=7.0 Hz, 3H), 1.22 (d, J=7.0 Hz, 3H), 1.56–1.63 (m, 2H), 2.52–2.59 (m, 1H), 2.67–2.74 (m, 1H), 2.91 (sept, J=7.0 Hz, 1H), 5.33 (s, 1H), 5.92 (d, J=1.2 Hz, 1H), 5.93 (d, J=1.2 Hz, 1H), 6.72 (d, J=8.5 Hz, 1H), 6.76 (d, J=8.5 Hz, 1H), 7.04. (d, J=7.5 Hz, 1H), 7.05 (s, 1H), 7.21 (d, J=8.5 Hz, 2H), 7.64 (dd, J=2.0, 8.5 Hz, 1H), 7.67 (d, J=8.5 Hz, 2H), 7.73 (d, J=2.0 Hz, 1H).

Microanalysis for C$_{28}$H$_{27}$NSO$_8$K$_2$.3.4 H$_2$O. KF=9.00 (calc for 3.4 H$_2$O=9.04) Calc'd: C=49.67; H=5.03; N=2.07; K=11.55; S=4.74. Found: C=49.30; H=4.95; N=2.06; K=11.85; S=4.82

Method B:

Step A Preparation of N-(4-iso-propylbenzenesulfonyl)-$\alpha$-(4-carboxy-2-n-propylphenoxy)-3,4-methylenedioxyphenylacetamide A mixture of 205 g (0.345 mol) of the product of Example 6,425 mL of 1.0N KOH in methanol and 500 mL of water was stirred at 60° C. under a nitrogen atmosphere. After 1.75 hours TLC analysis (90:10:1 CH$_2$Cl$_2$-MeOH-NH$_4$OH) indicated that ester hydrolysis was complete. The reaction mixture was cooled slightly, then concentrated on a rotary evaporator. The concentrate was acidified with 400 mL of 2N HCl and extracted first with 6 L of ether-EtOAc-CH$_2$Cl$_2$ 4:1:1, then with 3 L of 1:2 EtOAc-CH$_2$Cl$_2$. The organic layers were washed with 250 mL of 2N HCl, then with 3×500 mL of water, dried with magnesium sulfate, filtered, and concentrated, during which, the product began to crystallize. The solution was concentrated to a white slurry of ca. 750 mL, diluted with 1 L of hexanes, cooled to 0° C., aged 1 hr then filtered. The product was air dried affording 170.0 g (91% yield) of the title compound as a white crystalline solid.

$^1$H-NMR (400 MHz, CD$_3$OD, ppm): $\delta$0.88 (t, J=7.2 Hz, 3H), 1.21 (d, J=7.00 Hz, 3H), 1.22 (d, J=7.0 Hz, 3H), 1.56–1.63 (m, 2H), 2.52–2.59 (m, 1H), 2.67–2.74 (m, 1H), 2.91 (sept, J=7.0 Hz, 1H), 5.33 (s, 1H), 5.92 (d, J=1.2 Hz, 1H), 5.93 (d, J=1.2 Hz, 1H), 6.72 (d, J=8.5 Hz, 1H), 6.76 (d, J=8.5 Hz, 1H), 7.04 (d, J=7.5 Hz, 1H), 7.05 (s, 1H), 7.21 (d, J=8.5 Hz, 2H), 7.64 (dd, J=2.0, 8.5 Hz, 1H), 7.67 (d, J=8.5 Hz, 2H), 7.73 (d, J=2.0 Hz, 1H).

Microanalysis for C$_{28}$H$_{29}$NO$_8$S Calc'd: C=6233; H=5.42; N=2.60; S=5.94. Found: C=62.15; H=5.48; N=2.54; S=5.99

Step B: Preparation of N-(4-iso-propylbenzenesulfonyl)-$\alpha$-(4-carboxy-2-n-propylphenoxy )-3,4-methylenedioxyphenylacetamide dipotassium salt 159.7 g (0.296 mol) of acid from Step A was suspended in 3 L of absolute ethanol. To this was added 590 mL of 1.0N KOH in methanol over 20 min while simultaneously warming the mixture to 50° C. The clear and colorless solution was cooled to 0° C. during which it was added with 20 mg of the title compound. The suspension was stirred for 2 hr at 0° C., 1 L of ether was added and the suspension filtered. The solid was dried affording 168.4 g of the title compound as a white crystalline solid. A second crop of 22.3 g of comparable quality material was obtained by concentrating the mother liquors to ca. 1 L, diluting with 1 L of ether, filtering, and recrystallizing the solid (27 g) so obtained from 200 mL of 98% ethanol. Thus affording after drying a total of 190.7 g (96.8% yield corrected for water content) of the title compound.

Microanalysis for C$_{28}$H$_{27}$K$_2$NO$_8$S.2.75 H$_2$O. KF=7.45 (calc for 2.75 H$_2$O=7.44) Calc'd: C=50.55; H=4.92; N=2.11; K=11.75; Found: C=50.69; H=4.56; N=2.05; K=11.20; S=4.71

EXAMPLE 8

(−)-N-(4-iso-propylbenzenesulfonyl)-$\alpha$-(4-carboxy-2-n-propylphenoxy)-3,4-methylenedioxyphenylacetamide dipotassium salt Step A: Preparation of N-(4-iso-propylbenzenesulfonyl)-$\alpha$-(4-carboxy-2-n-propylphenoxy)-3,4-methylenedioxyphenylacetamide di-R-(+)-$\alpha$-methylbenzylamine salt 32.4 g of the acid from Example 6 was dissolved in 500 mL of isopropanol, and 15.5 mL of R-(+)-$\alpha$-methylbenzyl amine was added. The solution was allowed to stand at room temperature overnight. The mixture was filtered and the cake washed with a small amount of isopropanol. The solid was recrystallized 4 more times from isopropanol affording 4.5 g of the title compound.

Step B: Preparation of (−)-N-(4-iso-propylbenzenesulfonyl)-$\alpha$-(4-carboxy-2-n-propylphenoxy)-3,4-methylenedioxyphenylacetamide dipotassium salt The $\alpha$-methylbenzylamine salt from the above example was partitioned bet,ween ethyl acetate and 10% aqueous NaHSO$_4$, the organic layer was separated, dried with MgSO$_4$, filtered and concentrated. The residue was dissolved in methanol-water at room temperature, and basicified with ca. 12 mL of 1N NaOH in methanol, diluted with water and filtered through a 0.45 micron membrane filter. The solution was desalted and purified on a Waters Millipore Delta Prep 4000 liquid chromatograph equipped with an M1000 Prep-Pak module containing a 47×300 mm Delta-Pak C18 15 μm 100A column cartridge. Two solvent resevoirs were employed: solvent system A (95–5 water-acetonitrile), and solvent system B (5–95 water-acetonitrile), and the column effluent was monitored simultaneously at 210 and 280 nm with a Waters model 490 UV-visible detector. The sample was pump-injected onto the column and desalted by elution (50 mL/min) with several column volumes of solvent system A. A gradient elution was then begun which had as initial conditions 100% solvent system A-0% solvent system B and reached after 30 minutes 50% solvent system A-50% solvent system B, and the fractions were collected with an ISCO Foxy 200 fraction collector. The purified fractions were combined in round bottom flasks, frozen in a −78° C. dry ice-acetone bath, and lyophilized. Combination of the purified product afforded 4.8 g of the title compound as a white lyophilized powder.

$^1$H-NMR (400 MHz, CD$_3$OD, ppm): δ0.88 (t, J=7.2 Hz, 3H), 1.21 (d, J=7.0 Hz, 3H), 1.22 (d, J=7.0 Hz, 3H), 1.56–1.63 (m, 2H), 2.52–2.59 (m, 1H), 2.67–2.74 (m, 1H), 2.91 (sept, J=7.5 Hz, 1H), 5.33 (s, 1H), 5.92 (d, J=1.2 Hz, 1H), 5.93 (d, J=1.2 Hz, 1H), 6.72 (d, J=8.50 Hz, 1H), 6.76 (d, J=8.5 Hz, 1H), 7.04 (d, J=7.5 Hz, 1H), 7.05 (s, 1H), 7.21 (d, J=8.5 Hz, 2H), 7.64 (dd, J=2.0, 8.5 Hz, 1H), 7.67 (d, J=8.5 Hz, 2H), 7.73 (d, J=2.0 Hz, 1H).

Microanalysis for C$_{28}$H$_{27}$NSO$_8$K$_2$.H$_2$O. Calc'd: C=53.06; H=4.61; N=2.21; K=12.34. Found: C=52.81; H=4.56; N=2.17; K=12.02. [α]D=−48.9° (c=0.90, H$_2$O).

EXAMPLE 9

α-[4-[[(4,5-Dihydro-1-methyl-4-oxo-1H-imidazol-2-y)amino]carbonyl]2-n-propylphenoxy]-N-(4-iso-propylbenzenesulfonyl)-3,4-(methylenedioxy)phenylacetamide Step A: Preparation of ethyl α-(4-carbomethoxy-2-n-propylphenoxy)-3,4-(methylenedioxy)phenylacetate To a 2 L three necked 24/40 round bottom flask equipped with a mechanical stirrer, a nitrogen inlet and a dropping funnel was first added a solution of 36.0 g (0.185 mol) of methyl 4-hydroxy-3-n-propylbenzoate dissolved in 700 mL of anhydrous DMF followed by 66.4 g (0.204 mol) of cesium carbonate. The flask was purged with nitrogen and the reaction mixture was stirred at room temperature for 2 hours. A solution of 58.5 g (0.204 mol) of ethyl α-bromo-3,4-methylenedioxyphenylacetate dissolved in 100 mL of DMF was then added via an addition funnel over a 15 minute period. The reaction mixture was stirred an additional 1 hour at room temperature then quenched by addition to 5 L of a 5% aqueous citric acid solution. The organic product was extracted into diethyl ether (2×4 L), the organic layers were separated, washed with saturated aqueous NaCl, dried (MgSO$_4$), filtered, and evaporated. The residue was applied to a silica gel (2 kg; 70–230 mesh) column equilibrated in 10% CH$_2$Cl$_2$-hexane. The column was then eluted successively with 12 L of 10% CH$_2$Cl$_2$-hexane, 12 L of 5% EtOAc-hexane, 4 L of 7.5% EtOAc-hexane, 12 L of 10% EtOAc-hexane, and finally 8 L of 20% EtOAc-hexane. Combination of the purified fractions and evaporation in vacuo afforded 76.3 g (74.2 theoretical) of the rifle compound as a pale yellow oil which was used without further purification in the next step.

Step B: Preparation of α-(4-carbomethoxy-2-n-propylphenoxy)-3,4-(methylenedioxy)phenylacetic acid A 1 L 3 necked 24/40 round bottom flask equipped with a mechanical stirrer, a dropping funnel, and a nitrogen inlet was charged with a solution o,f 76.3 g 0.185 mol) of the semi-purified product of Step A dissolved in 500 mL of methanol. The flask was purged with nitrogen, the stirrer was started, and 37 mL of a 5.0N aqueous solution of sodium hydroxide was added over a 30 minute period via an addition funnel. The reaction mixture was stirred at room temperature for an additional 30 minutes at which point TLC analysis (CH$_2$Cl$_2$-MeOH-NH$_4$OH 90:10:1) indicated that the starting material had been consumed. The reaction mixture was adjusted to pH=4 with 6N HCl, and the bulk of the organic solvent was removed in vacuo. The precipitated organic product and the aqueous layer were next partitioned between CH$_2$Cl$_2$ (1 L) and water (1 L) which produced a copious emulsion. The reaction mixture was then aged overnight in a refrigerator which resulted in crystallization of the organic product. The crystalline solid was separated from the two phase mixture by filtration and washed with CH$_2$Cl$_2$. The solid was slurried again in diethyl ether, filtered, washed with hexane, and then dried in a vacuum to afford 65 g (94%) of the title compound as a white crystalline solid.

$^1$H-NMR (400 MHz, CD$_3$OD, ppm): δ0.93 (t, J=7.20 Hz, 3H), 1.62–1.75 (m, 2H), 2.63–2.70 (m, 1H), 2.77–2.81 (m, 1H), 3.84 (s, 3H), 5.54 (s, 1H), 5.94 (s, 2H), 6.81 (d, J=7.60 Hz, 1H), 6.89 (d, J=9.20 Hz, 1H), 7.08 (d, J=1.60 Hz, 1H). 7.11 (br s, 1H), 7.78–7.81 (m, 2H), Step C: Preparation of N-(4-iso-propylbenzenesulfonyl)-α-(4-carbomethoxy-2-n-propylphenoxy)-3,4-(methylenedioxy)phenylacetamide An oven dried three-necked 24/40 1 L round-bottom flask was equipped with a mechanical stirrer, a nitrogen inlet, and a septum. The flask was flushed with nitrogen, then charged with 20.06 g (53.9 mmol) of the product of Step B, 400 mL of anhydrous THF, and 9.76 mL (70.0 mmol) of triethylamine. The flask and its contents were stirred and cooled to −78° C. with an external dry ice-acetone bath and then 7.30 mL (59.3 mmol) of trimethylacetyl chloride was added slowly via a syringe. After the addition was complete, the dry ice-acetone bath was replaced with an ice-water bath and the reaction was stirred at 0° C. for 1 hour. A separate oven dried 3 necked 24/40 2 L round-bottom flask was equipped with a mechanical stirrer a septum and a nitrogen inlet. The flask was flushed with nitrogen then charged with 16.102 g (80.8 mmol) of 4-iso-propylbenzenesulfOnamide and 300 mL of anhydrous methyl sulfoxide. The stirrer was started and a 162 mL of a 1.0M solution of lithium bis(trimethylsilylamide) in THF was slowly (mildly exothermic) added via a syringe through the septum. After the addition was complete, the reaction mixture was stirred at room temperature for an additional 30 minutes. The contents of the first reaction mixture including a fine white precipitate that was suspended in the reaction mixture were then slowly transfered to the stirred solution of the deprotonated sulfonamide in the second flask via a wide diameter cannula. The combined reaction mixture was then stirred for an additional 14 hours under a nitrogen atmosphere. The reaction was the quenched with 1.0N HCl and the majority of the volatile solvents were removed in vacuo. The residue was partitioned between EtOAc and 1.0N HCl, then organic layer was separated, washed with saturated aqueous NaCl, dried (MgSO$_4$), filtered and evaporated in vacuo. The residue was purified on a silica gel (3 kg; 70–230 mesh) chromatography column (15 cm×150 cm) eluted with (90:10:1 CH$_2$Cl$_2$-MeOH-NH$_4$OH). Combination of the purified fractions and evaporation in vacuo afforded 18.367 g (62%) of the title compound.

$^1$H-NMR (400 MHz, CD$_3$OD, ppm): δ0.88 (t, J=7.60 Hz, 3H), 1.24 (d, J=7.00 Hz, 3H), 1.25 (t, J=7.00 Hz, 3H), 1.55–1.60 (m, 2H), 2.59–2.66 (m, 2H), 2.97 (sept, J=7.00 Hz, 1H), 3.83 (s, 3H), 5.52 (s, 1H), 5.97 (s, 2H), 6.50 (d, J=8.80 Hz, 1H), 6.80 (d, J=8.00 Hz, 1H), 6.89 (d, J=1.60 Hz, 1H), 6.94 (dd, J=2.00, 8.00 Hz, 1H), 7.14 (d, J=8.80 Hz, 2H), 7.59 (dd, J=2.20, 8.80 Hz, 1H), 7.75 (d, J=2.20, 1H), 7.79 (d, J=8.80 Hz, 2H).

Step D: Preparation of N-(4-iso-propylbenzenesulfonyl)-α-(4-carboxy-2-n-propylphenoxy)-3,4-(methylenedioxy)phenylacetamide To a solution of 18.367 g (33.2 mmol) of the product of Step C dissolved in 100 mL of methanol was added a solution of 6.56 g (116.9 mmol) of potassium hydroxide in 25 mL of water and the reaction mixture was stirred at 60° C. under a nitrogen atmosphere. After 6 hours TLC analysis (80:15:1 CHCl$_3$-MeOH-NH$_4$OH) indicated that ester hydrolysis was complete. The reaction mixture was cooled to room temperature, diluted with 100 mL water, filtered through a 0.45 micron filter and then divided into two equal volume portions. The fractions were individually desalted and purified on a Waters Millipore Delta Prep 3000 liquid chromatograph equipped with an M1000 Prep-Pak module containing a 47×300 mm Delta-Pak C18 15 μm 100A column cartridge. Two solvent resevoirs were employed: solvent system A (95-5 water-acetonitrile), and solvent system B (5-95 water-acetonitrile), and the column effluent was monitored simultaneously at 210 and 280 nm with a Waters model 490 UV-visible detector. Each fraction was pump-injected onto the column and desalted by elution (50 mL/min) with several column volumes of solvent system A. A gradient elution was then begun which had as initial conditions 100% solvent system A-0% solvent system B and reached after 30 minutes 50% solvent system A-50% solvent system B, and the fractions were collected with an ISCO Foxy 200 fraction collector. The purified fractions were combined in round bottom flasks, frozen in a −78° C. dry ice-acetone bath, and lyophilized. Combination of the purified product afforded 18.719 g (92%) of the title compound as a white lyophilized powder.

$^1$H-NMR (400 MHz, CD$_3$OD, ppm): δ0.88 (t, J=7.20 Hz, 3H), 1.21 (d, J=7.00 Hz, 3H), 1.22 (d, J=7.00 Hz, 3H), 1.56–1.63 (m, 2H), 2.52–2.59 (m, 1H), 2.67–2.74 (m, 1H), 2.91 (sept, J=7.00 Hz, 1H), 5.33 (s, 1H), 5.92 (d, J=1.20 Hz, 1H), 5.93 (d, J=1.20 Hz, 1H), 6.72 (d, J=8.50 Hz, 1H), 6.76 (d, J=8.50 Hz, 1H), 7.04 (d, J=7.50 Hz, 1H), 7.05 (s, 1H), 7.21 (d, J=&50 Hz, 2H), 7.64 (dd, J=2.00, 8.50 Hz, 1H), 7.67 (d, J=8.50 Hz, 2H), 7.73 (d, J=2.00 Hz, 1H).

Microanalysis for C$_{28}$H$_{27}$NSO$_8$K$_2$.H$_2$O. Calc'd: C=53.06; H=4.61; N=2.21; K=12.34. Found: C=52.81; H=4.56; N=2.17; K=12.02.

The free acid form is readily prepared by partitioning the dipotassium salt between aqueous sodium bisulfate and EtOAc. The EtOAc phase is separated and dried over anhydrous Na$_2$SO$_4$, filtered and concentrated to give the free acid product, as described in Example 7, Method B, Step A.

Step E: Preparation of α-[4-[[(4,5-dihydro-1-methyl-4-oxo-1H-imidazol-2-yl)amino]carbonyl]-2-n-propylphenoxy]-N-(4-isopropylbenzenesulfonyl)-3,4-methylenedioxyphenylacetamide To a solution of 200 mg (0.370 mmol) of N-(4-isopropylbenzenesulfonyl)-α-(4-carboxy-2-n-propylphenoxy)-3,4-methylenedioxyphenylacetamide (from Step D) in 1 mL of dry THF was added 90 mg (0.556 mmol) of 1,1-carbonyldiimidazole. The solution was stirred at reflux under N$_2$ for 2 hours. The cooled solution was evaporated to dryness. The residue was dissolved in 1 mL of acetonitrile and treated with 63 mg (0.556 mmol) of 2-amino-4,5-dihydro-1-methyl-1H-imidazol-4-one (creatinine) and 129 μL (93.7 mg; 0.925 mmol) of triethylamine. The mixture was stirred at reflux overnight. The cooled reaction mixture was quenched by addition of 1N HCl and extracted twice with EtOAc. The combined organic extracts were dried over MgSO$_4$, and filtered. The filtrate was concentrated, and the residue was flash chromatographed (silica gel, 27×3.5 cm; elution with 500 mL of 99:1:1 CHCl$_3$-MeOH-concentrated NH$_4$OH followed by 1 L of 85:15:1 CHCl$_3$-MeOH-concentrated NH$_4$OH) to give 142 mg (60%) of the title compound as a yellow solid, mp 137°–139 ° C.; homogeneous by TLC in 85:15:1 CHCl$_3$-MeOH-concentrated NH$_4$OH. ESI mass spectrum m/e 635 (M+H)$^+$.

400 MHz $^1$H NMR (CD$_3$OD) δ0.88 (t, J=7.3 Hz, 3 H), 1.20 (d, J=7.1 Hz, 6 H), 1.60 (m, 2 H), 2.5–2.8 (complex m, 2 H), 2.89 (m, 1 H), 3.21 (s, 3 H), 4.05 (s, 2 H), 5.38 (s, 1 H), 5.94 (s, 2 H), 6,.72–6.77 (m, 2 H), 7.03–7.05 (,m, 2 H), 7.20 (d, J=8.4 Hz, 2 H), 7.66 (d, J=8.4 Hz, 2H), 7.91–7.93 (m, 2 H).

Also within the scope of this invention are the compounds prepared from (−)-N-(4-iso-propylbenzenesulfonyl)-α-(4-carboxy-2-n-propylphenoxy)-3,4-methylenedioxyphenylacetamide dipotassium salt (Example 8), by hydrolysing to the free acid according to the procedures described above and reacting with the desired heterocyclic amine according to the procedure described in Example 9.

Additional examples, which are listed in Table I, were prepared according to the procedures described above in Example 9.

TABLE I

| Example No. (Ref. for prep. of amine) | —(CH$_2$)$_p$—E—R$^{16}$ | melting point (°C.) | ESI-MS m/e (M + H)$^+$ |
|---|---|---|---|
| 10 | | 108–110 | 606 |
| 11 | | 169–171 | 622 |
| 12 | | 191–193.5 | 623 |
| 13 (1) | | 243–244 | 634 |
| 14 (2) | | 147.5–149.5 | 619 |
| 15 | | 161–163 | 638 |
| 16 | | 187–189 | 620 |
| 17 | | 154–156 | 619 |
| 18 (3) | | 136–138 | 619 |

TABLE I-continued

[Structure: R¹⁶—E—(CH₂)ₚ—NH—C(=O)—(3-propyl-4-substituted phenyl); with central CH bearing benzodioxole, connected to C(=O)—NH—S(=O)₂—(4-isopropylphenyl)]

| Example No. (Ref. for prep. of amine) | —(CH₂)ₚ—E—R¹⁶ | melting point (°C.) | ESI-MS m/e (M + H)⁺ |
|---|---|---|---|
| 19 (4) | H-N-N=N triazole with =C(CH₃)-CONH₂ | 160–162 | 649 |
| 20 | —CH₂—(furan-2-yl) | 114–116 | 619 |
| 21 | —CH₂—(thiophen-2-yl) | 122–124 | 635 |
| 22 | —CH₂—(N-ethyl-pyrrolidin-2-yl) | 235–237 | 650 |

Additional compounds of this Formula which can be prepared using the procedure described in Example 9 with the appropriate amine starting material, R¹⁶-E—(CH₂)ₚ-NH₂, wherein the R¹⁶⁻ᴱ⁻⁽ᶜᴴ²⁾ₚ-substituent is as defined below:

| Example No. (Ref. for prep. of amine) | —(CH₂)ₚ—E—R¹⁶ | melting point (°C.) | ESI-MS m/e (M + H)⁺ |
|---|---|---|---|
| 23 (5) | 2-isopropylidene-imidazolin-5-one-N-CH₂— | 176–179 | 659 |
| 24 (6) | 2-isopropylidene-oxazolin-5-one-N-CH₂— | — | — |
| 25 (7) | 2-isopropylidene-4-methyl-thiazolin-5-one-N— | — | — |
| 26 (8) | —CH₂—(isopropylidene-oxazole) | 127–129 | 621 |
| 27 (9) | —CH₂—(isopropylidene-thiazole) | — | — |
| 28 (10) | —CH₂—(isopropylidene-imidazole-NH) | 220–222 | 619 |
| 29 (11) | isopropylidene-N-methyl-triazole | 165–167.5 | 620 |

References for the preparation of the heterocyclic amines used in the preparations of the compounds of this invention, which were not commercially available can be prepared according to the procedures described in the cited reference.

1. Wolf, V. et al., Chem. Ber., 95 (1962), 2419–23.
2. Lawson, J. Chem. Soc., 1956 307.
3. Chu; Lynch, J.Med. Chem., 18 (1975), 161.
4. Schwartz, J.; Hornyak, M.; Suts, T., Chem. Ind. (London) (3) 92–3 1970.
5. Kwon, Chul-Hoon; Iqbal, Muhammad Tahir; Wurpel, John, N. D., J. Med. Chem., 34 (1991) 6, 1845–9.
6. Traube; Ascher, Chem Bet., 46 (1913), 2079.
7. Hurst, Derek T.; Stacey, Anthony D.; Netherclift, Mark; Rahim, Amjad; Hamden, Michael R. Aust. J. Chem. 41 (1988) 8, 1221–29.
8. Gregory, G. I.; Seale, P. W.; Warburton, W. K.; Wilson, M. J., J. Chem. Soc., Perkins Trans. 1(1), 47–51 (1973). [Note: 3-Cyano1,2,4-oxadiazole, which is prepared according this reference, may be reduced to the 3-aminomethyl using lithium aluminum hydride]
9. Jones, et al., J. Amer. Chem. Soc, 72 (1950) 4526.
10. Bastiaansen; Godefroi, J. Orb Chem., 43 (1978), 1603.
11. Barascut, J. L; Claramunt, R. M.; Elguero, J. Bull. Soc. Chim. Fr. (1973), 1849–1853.

What is claimed is:

1. A compound of structural formula I:

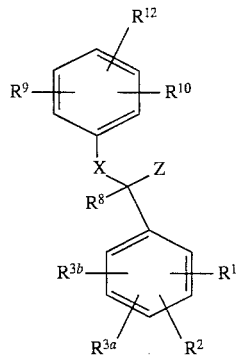

or a pharmaceutically acceptable salt thereof, wherein:

$R^1$, $R^2$, $R^{3a}$ and $R^{3b}$ are independently:
- (a) H,
- (b) F, Cl, Br, or I,
- (c) —$NO_2$,
- (d) —$NH_2$,
- (e) —NH($C_1$–$C_4$)-alkyl,
- (f) —N[($C_1$–$C_4$)-alkyl]$_2$,
- (g) —$SO_2NHR^7$,
- (h) —$CF_3$,
- (i) ($C_1$–$C_6$)-alkyl,
- (j) —$OR^7$,
- (k) —$S(O)_n$—($C_1$–$C_4$)-alkyl,
- (l) —NHCO—($C_1$–$C_4$)-alkyl,
- (m) —NHCO—O($C_1$–$C_4$)-alkyl,
- (n) —$CH_{2O}$—($C_1$–$C_4$)-alkyl,
- (o) —O—$(CH_2)_m$—$OR^7$,
- (p) —$CONR^7R^{11}$,
- (q) —$COOR^7$, or
- (r) -phenyl;

$R^1$ and $R^2$ on adjacent carbon atoms can be joined together to form a ring structure:

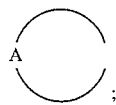

A represents:
- a) —Y—C($R^4$)=C($R^5$)—,
- b) —Y—C($R^4$)=N—,
- c) —Y—N=C($R^4$)—,
- d) —Y—[C($R^6$)($R^6$)]$_s$—Y—,
- e) —Y—C($R^6$)($R^6$)—C($R^6$)($R^6$)—,
- f) —C($R^4$)=C($R^5$)—Y—,
- g) —N=C($R^4$)—Y—,
- h) —C($R^6$)($R^6$)—C($R^6$)($R^6$)—Y—, or
- i) —C($R^4$)=C($R^5$)—C($R^4$)=C($R^5$)—;

n is 0, 1 or 2;

m is 2, 3 or 4;

s is 1 or 2;

Y is —O—, —$S(O)_n$— and $NR^7$;

$R^4$ and $R^5$ are independently:
- (a) H,
- (b) ($C_1$–$C_6$)-alkyl or ($C_2$–$C_6$)-alkenyl each of which is unsubstituted or substituted with one or two substituents selected from the group consisting of:
  - i) —OH,
  - ii) —O—($C_1$–$C_4$)-alkyl,
  - iii) —$S(O)_n$—($C_1$–$C_4$)-alkyl,
  - iv) —$NR^7$—($C_1$–$C_4$)-alkyl,
  - v) —$NHR^7$,
  - vi) —$COOR^7$,
  - vii) —$CONHR^7$,
  - viii) —$OCOR^{11}$, or
  - ix) —$CONR^7R^{11}$,
- (c) ($C_3$–$C_7$)-cycloalkyl,
- (d) F, Cl, Br, I,
- (e) $CF_3$,
- (f) —$COOR^7$,
- (g) —$CONR^7R^{11}$,
- (h) —$NR^7R^{11}$,
- (i) —$NR^7CONR^7R^{11}$,
- (j) —$NR^7COOR^{11}$,
- (k) —$SO_2NR^7R^{11}$,
- (l) —O—($C_1$–$C_4$)-alkyl,
- (m) —$S(O)_n$—($C_1$–$C_4$)-alkyl, or
- (n) —$NHSO_2R^{11}$;

$R^6$ is:
- (a) H,
- (b) ($C_1$–$C_4$)-alkyl unsubstituted or substituted with one of the following substituents:
  - i) —OH,
  - ii) —$NR^7R^{11}$,
  - iii) —$COOR^7$,
  - iv) —$CONHR^7$, or
  - v) —$CONR^7R^{11}$, or
- (c) Cl, or F;

$R^7$ is:
- (a) H,
- (b) ($C_1$–$C_6$)-alkyl,
- (c) phenyl,
- (d) ($C_1$–$C_6$)-alkylphenyl, or
- (e) ($C_3$–$C_7$)-cycloalkyl;

$R^8$ is:
- (a) H,
- (b) ($C_1$–$C_6$)-alkyl, unsubstituted or substituted with a substituent selected from the group consisting of:
  - (i) -phenyl,
  - (ii) —($C_3$–$C_7$)-cycloalkyl,
  - (iii) —$NR^7R^{11}$,
  - (iv) -morpholin-4-yl,
  - (v) —OH,
  - (vi) —$CO_2R^7$, or
  - (vii) —$CON(R^7)_2$,
- (c) phenyl, unsubstituted or substituted with a substituent selected from the group consisting of:

i) ($C_1$–$C_4$)-alkyl
ii) —O—($C_1$–$C_4$)-alkyl
iii) —CONR$^7$R$^{11}$,
iv) F, Cl, B r or I, or
v) —COOR$^7$;

R$^9$ and R$^{10}$ are independently:
(a) H,
(b) ($C_1$–$C_6$)-alkyl, unsubstituted or substituted with ($C_3$–$C_7$)-cycloalkyl or —CO$_2$R$^7$,
(c) ($C_2$–$C_6$)-alkenyl,
(d) ($C_2$–$C_6$)-alkynyl,
(e) Cl, Br, F, I,
(f) ($C_1$–$C_6$)-alkoxy,
(g) perfluoro-($C_1$–$C_6$)-alkyl,
(h) ($C_3$–$C_7$)-cycloalkyl, unsubstituted or substituted with ($C_1$–$C_6$)-alkyl,
(i) phenyl,
(j) ($C_1$–$C_6$)-alkyl-S(O)$_n$—(CH$_2$)$_n$—,
(k) hydroxy-($C_1$–$C_6$)-alkyl,
(l) —CN,
(m) —CO$_2$R$^7$,
(n) —OH,
(o) —NR$^7$R$^{11}$,
(p) —[($C_1$–$C_6$)-alkyl]NR$^7$R$^{11}$,
(q) —NO$_2$,
(r) —(CH$_2$)$_n$—SO$_2$—N(R$^7$)$_2$,
(s) —NR$^7$CO—($C_1$–$C_4$)-alkyl, or
(t) —CON(R$^7$)$_2$;

R$^9$ and R$^{10}$ on adjacent carbons can join together to form a fused phenyl ring, unsubstituted or substituted with a substituent selected from the group consisting of: ($C_1$–$C_6$)-alkyl, ($C_1$–$C_6$)-alkoxy, ($C_3$–$C_7$)-cycloalkyl and ($C_1$–$C_6$)-alkyl-($C_3$–$C_7$)-cycloalkyl, R$^{11}$ is
(a) ($C_1$–$C_6$)-alkyl, unsubstituted or substituted with a substituent selected from the group consisting of:
  (i) —OR$^7$,
  (ii) —N[R$^7$]$_2$,
  )iii) —NH$_2$,
  (iv) —COOR$^7$,
  (v) —N[CH$_2$CH$_2$]$_2$Q,
  (vi) —CF$_3$, or
  (vii) —CON(R$^7$)$_2$;
(b) aryl, wherein aryl is defined as phenyl or naphthyl which is unsubstituted or substituted with one or two substituents selected from the group consisting of:
  i) ($C_1$–$C_4$)-alkyl,
  ii) —O—($C_1$–$C_4$)-alkyl,
  iii) —CO[NR$^7$]$_2$,
  iv) F, Cl, Br or I,
  v) —COOR$^7$,
  vi) —NH$_2$,
  vii) —NH[($C_1$–$C_4$)-alkyl],
  viii) —N[($C_1$–$C_4$)-alkyl]$_2$, or
  ix) —CON[CH$_2$CH$_2$]$_2$Q;
(c) —($C_1$–$C_4$)-alkylaryl, wherein aryl is as defined above,
(d) ($C_3$–$C_7$)-cycloalkyl,
(e)

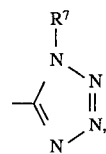

or
(f) CF$_3$;

R$^7$ and R$^{11}$ on the same nitrogen atom they can join together to form a ring selected from the group consisting of: morpholinyl, piperazinyl, or pyrrolyl, or Q is O, or —NR$^7$;
R$^{12}$ is —CONR$^7$(CH$_2$)$_p$—E—R$^{16}$;
p is 0 to 4;
E is a single bond, NH, O, S, with the proviso that E is a single bond when p is 0 or 1;
X is
(a) —O—,
(b) —S(O)$_n$—,
(c) —NR$^7$—,
(d) —CH$_2$O—,
(e) —CH$_2$S(O)$_n$—,
(f) —CH$_2$NR$^7$—,
(g) —OCH$_2$—,
(h) —N(R$^7$)CH$_2$—,
(i) —S(O)$_n$CH$_2$—, or
(j) -single bond;

Z is:
(a) —CO$_2$H,
(b) —CO$_2$R$^{13}$,
(c) —CONH—(tetrazol-5-yl),
(d) —CONHSO$_2$OR$^{11}$
(e) —CONHSO$_2$NR$^7$R$^{11}$,
(f) —CONHSO$_2$-aryl, wherein aryl is defined as phenyl or naphthyl which is unsubstituted or substituted with one, two or three substituents selected from the group consisting of:
  i) ($C_1$–$C_4$)-alkyl,
  ii) —O—(Cl–$C_4$)-alkyl,
  iii) —CONR$^7$R$^{11}$,
  iv) F, Cl, Br or I,
  v) —COOR$^7$,
  vi) —NH$_2$,
  vii) —NH[($C_1$–$C_4$)-alkyl],
  viii) —N[($C_1$–$C_4$)-alkyl]$_2$,
  ix) -phenyl,
  x) —OH,
  xi) —OCH$_2$CH$_2$OH,
  xii) —CF$_3$;
(g) —CONHSO$_2$—($C_1$–$C_8$)-alkyl, wherein the alkyl group is unsubstituted or substituted as defined in R$^4$(b),
(h) —CONHSO$_2$—($C_1$–$C_4$)-perfluoroalkyl,
(i) -tetrazol-5-yl,
(j) —CONHSO$_2$-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl or quinolinyl, which is unsubstituted or substituted with one, two or three substituents selected from the group consisting of:
  i) ($C_1$–$C_4$)-alkyl,
  ii) —O—($C_1$–$C_4$)-alkyl,
  iii) —CONR$^7$R$^{11}$, iv) F, Cl, Br or I,
v) —COOR$^7$,
vi) —NR$^7$CONR$^7$R$^{11}$, and
vii) —NR$^7$COOR$^{11}$,;
(k) —SO$_2$NHCO—aryl, wherein aryl is defined in Z(d) above,
(l) —SO$_2$NHCO—(C$_1$-C$_8$)-alkyl, wherein the alkyl group is unsubstituted or substituted as defined in R$^4$(b),
(m) —SO$_2$NHCO—(C$_1$-C$_4$)-perfluoroalkyl,
(n) —SO$_2$NHCO—heteroaryl, wherein heteroaryl is as defined in Z(g) above,
(o) —SO$_2$NHCON(R$^{11}$)$_2$ wherein the R$^{11}$ groups are the same or different,
(p) —PO(OR$^7$)$_2$, wherein the R$^7$ groups are the same or different, or
(q) —PO(R$^{11}$)OR$^7$;

R$^{13}$ is:
(a) (C$_1$-C$_4$)-alkyl,
(b) CHR$^{14}$—O—COR$^{15}$,
(c) CH$_2$CH$_2$—N[(C$_1$-C$_2$)-alkyl]$_2$,
(d) CH$_2$CH$_2$—N[CH$_2$CH$_2$]$_2$O,
(e) (CH$_2$CH$_2$O)$_y$—O—[(C$_1$-C$_4$)-alkyl], wherein y is 1 or 2,
(f) phenyl, naphthyl, CH$_2$-phenyl or CH$_2$-naphthyl, where phenyl or naphthyl is substituted or unsubstituted with CO$_2$-(C$_1$-C$_4$)-alkyl, (g) 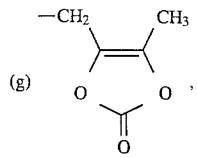

(h) 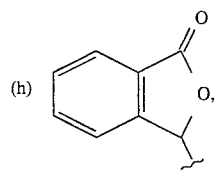

(i) 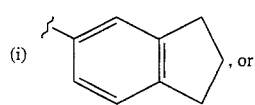, or (j) 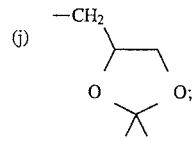

and

R$^{14}$ and R$^{15}$ independently are (C$_1$-C$_6$)-alkyl or phenyl;
R$^{16}$ is a saturated or partially or fully unsaturated 5-membered heterocycle substituted-with one, two or three heteroatoms selected from: N, O, and S, wherein the carbon skeleton of the heterocycle is mono- or di-substituted with R$^9$ or an oxo group and the sp$^3$ nitrogen atoms of the saturated or partially unsaturated heterocycle are substituted with R$^8$, and with the proviso that R$^{16}$ is not an N-linked pyrrolidine; and
R$^{17}$ is:
(a) H,
(b) (C$_1$-C$_6$)-alkyl, unsubstituted or substituted with (C$_3$-C$_7$)-cycloalkyl or —CO$_2$R$^7$,
(c) (C$_2$-C$_6$)-alkenyl,
(d) (C$_2$-C$_6$)-alkynyl,
(e) Cl, Br, F, I,
(f) (C$_1$-C$_6$)-alkoxy,
(g) perfluoro-(C$_1$-C$_6$)-alkyl,
(h) (C$_3$-C$_7$)-cycloalkyl, unsubstituted or substituted with (C$_1$-C$_6$)-alkyl,
(i) phenyl,
(j) (C$_1$-C$_6$)-alkyl-S(O)$_n$-(CH$_2$)$_n$—,
(k) hydroxy-(C$_1$-C$_6$)-alkyl,
(l) —CN,
(m) —CO$_2$R$^7$,
(n) —OH,
(o) —NR$^7$R$^{11}$,
(p) —[(C$_1$-C$_6$)-alkyl]NR$^7$R$^{11}$,
(q) —NO$_2$,
(r) —(CH$_2$)$_n$—SO$_2$—N(R$^7$)$_2$,
(s) —NR$^7$CO—(C$_1$-C$_4$)-alkyl, or
(t) —CON(R$^7$)$_2$.

2. The compound of claim 1 of structural formula I:

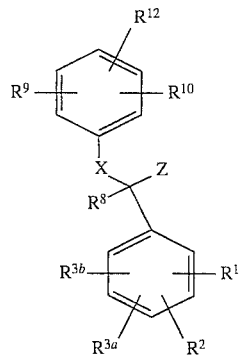 I or a pharmaceutically acceptable salt thereof, wherein:
R$^1$, R$^2$, R$^{3a}$ and R$^{3b}$ are independently:
(a) H,
(b) F, Cl, Br, or I,
(c) —NO$_2$,
(d) —NH$_2$,
(e) —NH(C$_1$-C$_4$)-alkyl,
(f) —N[(C$_1$-C$_4$)-alkyl]$_2$,
(g) —SO$_2$NHR$^7$,
(h) —CF$_3$,
(i) (C$_1$-C$_6$)-alkyl,
(j) —OR$^7$,
(k) —S(O)$_n$—(C$_1$-C$_4$)-alkyl,
(l) —NHCO—(C$_1$-C$_4$)-alkyl,
(m) —NHCO—O(C$_1$-C$_4$)-alkyl,
(n) —CH$_2$O—(C$_1$-C$_4$)-alkyl,
(o) —O—(CH$_2$)$_m$—OR$^7$,
(p) —CONR$^7$R$^{11}$, or
(q) —COOR$^7$;

R$^1$ and R$^2$ on adjacent carbon atoms can be joined together to form a ring structure:

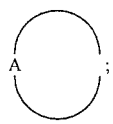

A represents:
a) —Y—C(R$^4$)=C(R$^5$)—,
b) —Y—C(R$^4$)=N—,
c) —Y—N=C(R$^4$)—,
d) —Y—[C(R$^6$)(R$^6$)]$_s$—Y—,
e) —Y—C(R$^6$)(R$^6$)—C(R$^6$)(R$^6$)—, f) —C(R⁴)=C(R⁵)—Y—,
g) —N=C(R⁴)—Y—,
h) —C(R⁶)(R⁶)—C(R⁶)(R⁶)—Y—, or
i) —C(R⁴)=C(R⁵)—C(R⁴)=C(R⁵)—;

m is 2, 3 or 4,
n is 0, 1 or 2,
s is 1 or 2,
Y is —O—, —S(O)$_n$— and NR⁷;
R⁴ and R⁵ are independently:
  (a) H,
  (b) (C₁–C₆)-alkyl or (C₂–C₆)-alkenyl each of which is unsubstituted or substituted with one or two substituents selected from the group consisting of:
    i) —OH,
    ii) —O—(C₁–C₄)-alkyl,
    iii) —S(O)$_n$—(C₁–C₄)-alkyl,
    iv) —NR⁷—(C₁–C₄)-alkyl,
    v) —NHR⁷,
    vi) —COOR⁷,
    vii) —CONHR⁷,
    viii) —OCOR¹¹, or
    ix) —CONR⁷R¹¹,
  (c) (C₃–C₇)-cycloalkyl,
  (d) F, Cl, Br, I,
  (e) CF₃,
  (f) —COOR⁷,
  (g) —CONR⁷R¹¹,
  (h) —NR⁷R¹¹,
  (i) —NR⁷CONR⁷R¹¹,
  (j) —NR⁷COOR¹¹,
  (k) —SO₂NR⁷R¹¹,
  (l) —O—(C₁–C₄)-alkyl,
  (m) —S(O)$_n$—(C₁–C₄)-alkyl, or
  (n) —NHSO₂R¹¹;
R⁶ is:
  (a) H,
  (b) (C₁–C₄)-alkyl unsubstituted or substituted with one or two substituents selected from the group consisting of:
    i) —OH,
    ii) —NR⁷R¹¹,
    iii) —COOR⁷,
    iv) —CONHR⁷, or
    v) —CONR⁷R¹¹, or
  (c) Cl, or F;
R⁷ is:
  (a) H,
  (b) (C₁–C₆)-alkyl,
  (c) phenyl,
  (d) (C₁–C₆)-alkylphenyl, or
  (e) (C₃–C₇)-cycloalkyl;
R⁸ is:
  (a) H,
  (b) (C₁–C₆)-alkyl, unsubstituted or substituted with one or two substituents selected from the group consisting of:
    (i) -phenyl,
    (ii) —(C₃–C₇)-cycloalkyl,
    (iii) —NR⁷R¹¹,
    (iv) -morpholin-4-yl,
    (v) —OH,
    (vi) —CO₂R⁷, or
    (vii) —CON(R⁷)₂, or
  (c) phenyl;
R⁹ and R¹⁰ are independently:
  (a) H,
  (b) (C₁–C₆)-alkyl, unsubstituted or substituted with (C₃–C₇)-cycloalkyl or —CO₂R⁷,
  (c) (C₂–C₆)-alkenyl,
  (d) (C₂–C₆)-alkynyl,
  (e) Cl, Br, F, I,
  (f) (C₁–C₆)-alkoxy,
  (g) perfluoro-(C₁–C₆)-alkyl,
  (h) (C₃–C₇)-cycloalkyl, unsubstituted or substituted with (C₁–C₆)-alkyl,
  (i) phenyl,
  (j) (C₁–C₆)-alkyl—S(O)$_n$—(CH₂)$_n$—,
  (k) hydroxy-(C₁–C₆)-alkyl,
  (l) —CN,
  (m) —CO₂$^{R7}$,
  (n) —OH,
  (o) —NR⁷R¹¹,
  (p) —[(C₁–C₆)-alkyl]NR⁷R¹¹,
  (q) —NO₂,
  (r) —(CH₂)$_n$—SO₂—N(R⁷)₂,
  (s) —NR⁷CO—(C₁–C₄)-alkyl, or
  (t) —CON(R⁷)₂;
R⁹ and R¹⁰ on adjacent carbons can join together to form a fused phenyl ring, unsubstituted or substituted with a substituent selected from the group consisting of: (C₁–C₆)-alkyl, (C₁–C₆)-alkoxy, (C₃–C₇)-cycloalkyl and (C₁–C₆)-alkyl-(C₃–C₇)-cycloalkyl,
R¹¹ is
  (a) (C₁–C₆)-alkyl, unsubstituted or substituted with a substituent selected from the group consisting of:
    i) —OR⁷,
    ii) —N[R⁷]₂,
    iii) —NH₂,
    iv) —COOR⁷,
    v) —N[CH₂CH₂]₂Q,
    vi) —CF₃, or
    vii) —CON(R⁷)₂;
  (b) aryl, wherein aryl is defined as phenyl or naphthyl which is unsubstituted or substituted with one or two substituents selected from the group consisting of:
    i) (C₁–C₄)-alkyl,
    ii) —O—(C₁–C₄)-alkyl,
    iii) —CO[NR⁷]₂,
    iv) F, Cl, Br or I,
    v) —COOR⁷,
    vi) —NH₂,
    vii) —NH[(C₁–C₄)-alkyl],
    viii) —N[(C₁–C₄)-alkyl]₂, or
    ix) —CON[CH₂CH₂]₂Q;
  (c) —(C₁–C₄)-alkylaryl, wherein aryl is as defined above,
  (d) (C₃–C₇)-cycloalkyl,
  (e)

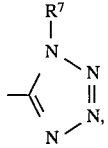

or
  (f) CF₃;
R⁷ and R¹¹ on the same nitrogen atom they can join together to form a ring selected from the group consisting of: morpholinyl, piperazinyl, or pyrrolyl, or
Q is O, or —NR⁷;

$R^{12}$ is —CONR$^7$(CH$_2$)$_p$—E—R$^{16}$;

p is 0 to 4;

E is a single bond, NH, O, S, with the proviso that E is a single bond when p is 0 or 1;

X is
- (a) —O—,
- (b) —S(O)$_n$—,
- (c) —NR$^7$—,
- (d) —CH$_2$O—,
- (e) —CH$_2$S(O)$_n$—,
- (f) —CH$_2$NR$^7$—,
- (g) —OCH$_2$—,
- (h) —N(R$^7$)CH$_2$—,
- (i) —S(O)$_n$CH$_2$—, or
- (j) -single bond;

Z is:
- (a) —CO$_2$H,
- (b) —CO$_2$R$^{13}$,
- (c) —CONH—(tetrazol-5-yl),
- (d) —CONHSO$_2$OR$^{11}$,
- (e) —CONHSO$_2$NR$^7$R$^{11}$,
- (f) —CONHSO$_2$—aryl, wherein aryl is defined as phenyl or naphthyl which is unsubstituted or substituted with one, two or three substituents selected from the group consisting of:
  - i) (C$_1$–C$_4$)-alkyl,
  - ii) —O—(C$_1$–C$_4$)-alkyl,
  - iii) —CONR$^7$R$^{11}$,
  - iv) F, Cl, B r or I,
  - v) —COOR$^7$,
  - vi) —NH$_2$,
  - vii) —NH[(C$_1$–C$_4$)-alkyl],
  - viii) —N[(C$_1$–C$_4$)-alkyl]$_2$,
  - ix) -phenyl,
  - x) —OH,
  - xi) —OCH$_2$CH$_2$OH,
  - xii) —CF$_3$;
- (g) —CONHSO$_2$—(C$_1$–C$_8$)-alkyl, wherein the alkyl group is unsubstituted or substituted as defined in R$^4$(b),
- (h) —CONHSO$_2$—(C$_1$–C$_4$)-perfluoroalkyl,
- (i) -tetrazol-5-yl,
- (j) —CONHSO$_2$-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl or quinolinyl, which is unsubstituted or substituted with one, two or three substituents selected from the group consisting of:
  - i) (C$_1$–C$_4$)-alkyl,
  - ii) —O—(C$_1$–C$_4$)-alkyl,
  - iii) —CONR$^7$R$^{11}$,
  - iv) F, Cl, Br or I,
  - v) —COOR$^7$,
  - vi) —NR$^7$CONR$^7$R$^{11}$, and
  - vii) —NR$^7$COOR$^{11}$;
- (k) —SO$_2$NHCO-aryl, wherein aryl is defined in Z(d) above,
- (l) —SO$_2$NHCO—(C$_1$–C$_8$)-alkyl, wherein the alkyl group is unsubstituted or substituted as defined in R$^4$(b),
- (m) —SO$_2$NHCO—(C$_1$–C$_4$)-perfluoroalkyl,
- (n) —SO$_2$NHCO—heteroaryl, wherein heteroaryl is as defined in Z(g) above,
- (o) —SO$_2$NHCON(R$^{11}$)$_2$ wherein the R$^{11}$ groups are the same or different,
- (p) —PO(OR$^7$)$_2$, wherein the R$^7$ groups are the same or different, or
- (q) —PO(R$^{11}$)OR$^7$;

$R^{13}$ is:
- (a) (C$_1$–C$_4$)-alkyl,
- (b) CHR$^{14}$—O—COR$^{15}$,
- (c) CH$_2$CH$_2$—N[(C$_1$–C$_2$)-alkyl]$_2$,
- (d) CH$_2$CH$_2$—N[CH$_2$CH$_2$]$_2$O,
- (e) (CH$_2$CH$_2$O)$_y$—O—[(C$_1$–C$_4$)-alkyl], wherein y is 1 or 2,
- (f) phenyl, naphthyl, CH$_2$-phenyl or CH$_2$-naphthyl, where phenyl or naphthyl is substituted or unsubstituted with

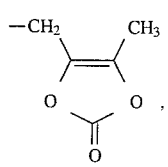 (g)

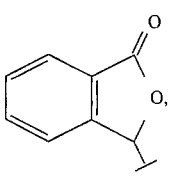 (h)

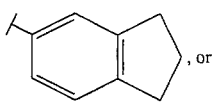 (i) , or

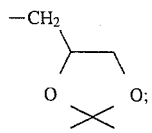 (j) ;

$R^{14}$ and $R^{15}$ independently are (C$_1$–C$_6$)-alkyl or phenyl; and $R^{16}$ is a saturated or partially or fully unsaturated 5-membered heterocycle substituted with one, two or three heteroatoms selected from: N, O, and S, which is selected from the group consisting of:

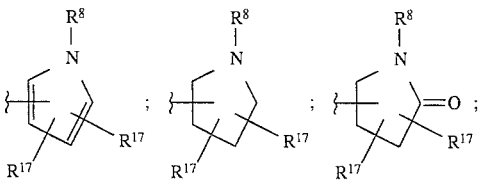

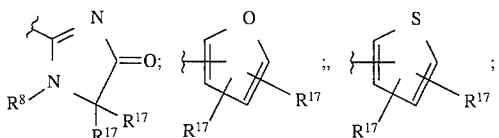

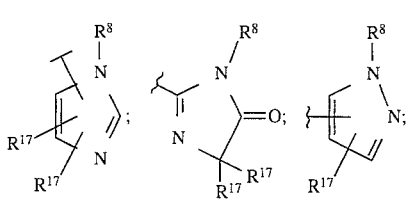

-continued

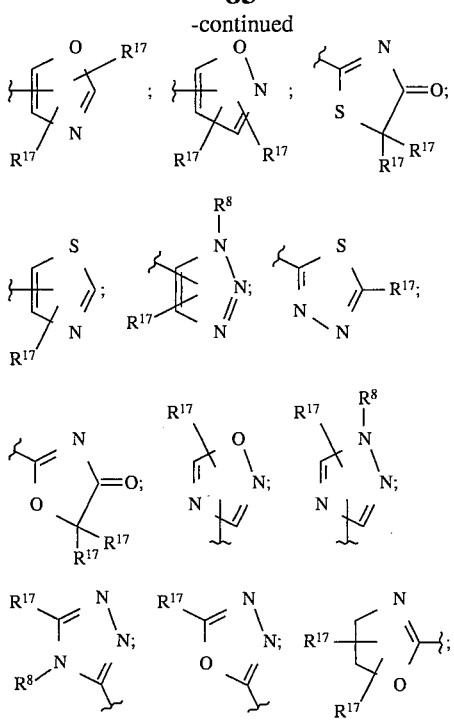

and

R[17] is:
(a) H,
(b) $(C_1-C_6)$-alkyl, unsubstituted or substituted with $(C_3-C_7)$-cycloalkyl or $-CO_2R^7$,
(c) $(C_2-C_6)$-alkenyl,
(d) $(C_2-C_6)$-alkynyl,
(e) Cl, Br, F, I,
(f) $(C_1-C_6)$-alkoxy,
(g) perfluoro-$(C_1-C_6)$-alkyl,
(h) $(C_3-C_7)$-cycloalkyl, unsubstituted or substituted with $(C_1-C_6)$-alkyl,
(i) phenyl,
(j) $(C_1-C_6)$-alkyl-$S(O)_n-(CH_2)_n-$,
(k) hydroxy-$(C_1-C_6)$-alkyl,
(l) —CN,
(m) $-CO_2R^7$,
(n) —OH,
(o) $-NR^7R^{11}$,
(p) $-[(C_1-C_6)\text{-alkyl}]NR^7R^{11}$,
(q) $-NO_2$,
(r) $-(CH_2)_n-SO_2-N(R^7)_2$,
(s) $-NR^7CO-(C_1-C_4)$-alkyl, or
(t) $-CON(R^7)_2$.

3. The compound of claim 2 of structural formula II:

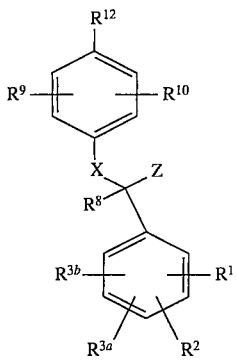

II or a pharmaceutically acceptable salt thereof, wherein:
$R^1$, $R^2$, $R^{3a}$ and $R^{3b}$ are independently:
(a) H,
(b) F, Cl, Br, or I,
(c) $-NO_2$,
(d) $-NH_2$,
(e) $-NH(C_1-C_4)$-alkyl,
(f) $-N[(C_1-C_4)\text{-alkyl}]_2$,
(g) $-SO_2NHR^7$,
(h) $-CF_3$,
(i) $(C_1-C_6)$-alkyl,
(j) $-OR^7$,
(k) $-S(O)_n-(C_1-C_4)$-alkyl,
(l) $-NHCO-(C_1-C_4)$-alkyl,
(m) $-NHCO-O(C_1-C_4)$-alkyl,
(n) $-CH_2O-(C_1-C_4)$-alkyl,
(o) $-O-(CH_2)_m-OR^7$,
(p) $-CONR^7R^{11}$, or
(q) $-COOR^7$;

$R^1$ and $R^2$ on adjacent carbon atoms can be joined together to form a ring structure:

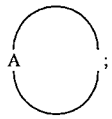

A represents:
a) $-Y-C(R^4)=C(R^5)-$,
b) $-Y-C(R^4)=N-$,
c) $-Y-N=C(R^4)-$,
d) $-Y-[C(R^6)(R^6)]_s-Y-$,
e) $-Y-C(R^6)(R^6)-C(R^6)(R^6)-$,
f) $-C(R^4)=C(R^5)-Y-$,
g) $-N=C(R^4)-Y-$,
h) $-C(R^6)(R^6)-C(R^6)(R^6)-Y-$, or
i) $-C(R^4)=C(R^5)-C(R^4)=C(R^5)-$;

m is 2, 3 or 4,
n is 0, 1 or 2,
s is 1 or 2,
Y is $-O-$, $-S(O)_n-$ and $NR^7$;
$R^4$ and $R^5$ are independently:
(a) H, (b) $(C_1-C_6)$-alkyl or $(C_2-C_6)$-alkenyl each of which is unsubstituted or substituted with one or two substituents selected from the group consisting of:
  i) —OH,
  ii) —O—$(C_1-C_4)$-alkyl,
  iii) —S(O)$_n$—$(Cl-C_4)$-alkyl,
  iv) —NR$^7$—$(C_1-C_4)$-alkyl,
  v) —NHR$^7$,
  vi) —COOR$^7$,
  vii) —CONHR$^7$,
  viii) —OCOR$^{11}$, or
  ix) —CONR$^7$R$^{11}$,
(c) $(C_3-C_7)$-cycloalkyl,
(d) F, Cl, Br, I,
(e) CF$_3$,
(f) —COOR$^7$,
(g) —CONR$^7$R$^{11}$,
(h) —NR$^7$R$^{11}$,
(i) —NR$^7$CONR$^7$R$^{11}$,
(j) —NR$^7$COOR$^{11}$,
(k) —SO$_2$NR$^7$R$^{11}$,
(l) —O—$(C_1-C_4)$-alkyl,
(m) —S(O)$_n$—$(C_1-C_4)$-alkyl, or
(n) —NHSO$_2$R$^{11}$;

R$^6$ is:
(a) H,
(b) $(C_1-C_4)$-alkyl unsubstituted or substituted with one or two substituents selected from the group consisting of:
  i) —OH,
  ii) —NR$^7$R$^{11}$,
  iii) —COOR$^7$,
  iv) —CONHR$^7$, or
  v) —CONR$^7$R$^{11}$, or
(c) Cl, or F;

R$^7$ is:
(a) H,
(b) $(C_1-C_6)$-alkyl,
(c) phenyl,
(d) $(C_1-C_6)$-alkylphenyl, or
(e) $(C_3-C_7)$-cycloalkyl;

R$^8$ is:
(a) H,
(b) $(C_1-C_6)$-alkyl, unsubstituted or substituted with one or two substituents selected from the group consisting of:
  (i) -phenyl,
  (ii) —$(C_3-C_7)$-cycloalkyl,
  (iii) —NR$^7$R$^{11}$,
  (iv) -morpholin-4-yl,
  (v) —OH,
  (vi) —CO$_2$R$^7$, or
  (vii) —CON(R$^7$)$_2$, or
(c) phenyl;

R$^9$ and R$^{10}$ are independently:
(a) H,
(b) $(C_1-C_6)$-alkyl, unsubstituted or substituted with $(C_3-C_7)$-cycloalkyl or —CO$_2$R$^7$,
(c) $(C_2-C_6)$-alkenyl,
(d) $(C_2-C_6)$-alkynyl,
(e) Cl, Br, F, I,
(f) $(C_1-C_6)$-alkoxy,
(g) perfluoro-$(C_1-C_6)$-alkyl,
(h) $(C_3-C_7)$-cycloalkyl, unsubstituted or substituted with $(C_1-C_6)$-alkyl,
(i) phenyl,
(j) $(C_1-C_6)$-alkyl-S(O)$_n$—(CH$_2$)$_n$—,
(k) hydroxy-$(C_1-C_6)$-alkyl,
(l) —CN,
(m) —CO$_2$R$^7$,
(n) —OH,
(o) —NR$^7$R$^{11}$,
(p) —[$(C_1-C_6)$-alkyl]NR$^7$R$^{11}$,
(q) —NO$_2$,
(r) —(CH$_2$)$_n$—SO$_2$—N(R$^7$)$_2$,
(s) —NR$^7$CO—$(C_1-C_4)$-alkyl, or
(t) —CON(R$^7$)$_2$;

R$^9$ and R$^{10}$ on adjacent carbons can join together to form a fused phenyl ring, unsubstituted or substituted with a substituent selected from the group consisting of: $(C_1-C_6)$-alkyl, $(C_1-C_6)$-alkoxy, $(C_3-C_7)$-cycloalkyl and $(C_1-C_6)$-alkyl-$(C_3-C_7)$-cycloalkyl, p1 R$^{11}$ is
(a) $(C_1-C_6)$-alkyl, unsubstituted or substituted with a substituent selected from the group consisting of:
  i) —OR$^7$,
  ii) —N[R$^7$]$_2$,
  iii) —NH$_2$,
  iv) —COOR$^7$,
  v) —N[CH$_2$CH$_2$]$_2$Q,
  vi) —CF$_3$, or
  vii) —CON(R$^7$)$_2$;
(b) aryl, wherein aryl is defined as phenyl or naphthyl which is unsubstituted or substituted with one or two substituents selected from the group consisting of:
  i) $(C_1-C_4)$-alkyl,
  ii) —O—$(C_1-C_4)$-alkyl,
  iii) —CO[NR$^7$]$_2$,
  iv) F, Cl, Br or I,
  v) —COOR$^7$,
  vi) —NH$_2$,
  vii) —NH[$(C_1-C_4)$-alkyl],
  viii) —N[$(C_1-C_4)$-alkyl]$_2$, or
  ix) —CON[CH$_2$CH$_2$]$_2$Q;
(c) —$(C_1-C_4)$-alkylaryl, wherein aryl is as defined above,
(d) $(C_3-C_7)$-cycloalkyl,
(e)

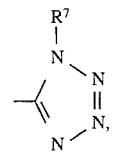

or
(f) CF$_3$;

R$^7$ and R$^{11}$ on the same nitrogen atom they can join together to form a ring selected from the group consisting of: morpholinyl, piperazinyl, or pyrrolyl, or Q is O, or —NR$^7$;

R$^{12}$ is —CONR$^7$(CH$_2$)$_p$—E—R$^{16}$;

p is 0 to 4;

E is a single bond, NH, O, S, with the proviso that E is a single bond when p is 0 or 1;

X is
(a) —O—,
(b) —S(O)$_n$—,
(c) —NR$^7$—,
(d) —CH$_2$O—,
(e) —CH$_2$S(O)$_n$—,
(f) —CH$_2$NR$^7$—,
(g) —OCH$_2$—,
(h) —N(R$^7$)CH$_2$—, (l) —S(O)$_n$CH$_2$—, or (j) -single bond;

Z is:
(a) —CO$_2$H,
(b) —CO$_2$R$^{13}$,
(c) —CONH—(tetrazol-5-yl),
(d) —CONHSO$_2$OR$^{11}$,
(e) —CONHSO$_2$NR$^7$R$^{11}$,
(f) —CONHSO$_2$—aryl, wherein aryl is defined as phenyl or naphthyl which is unsubstituted or substituted with one, two or three substituents selected from the group consisting of:
  i) (C$_1$–C$_4$)-alkyl,
  ii) —O—(C$_1$–C$_4$)-alkyl,
  iii) —CONR$^7$R$^{11}$,
  iv) F, Cl, Br or I,
  v) —COOR$^7$,
  vi) —NH$_2$,
  vii) —NH[(C$_1$–C$_4$)-alkyl],
  viii) —N[(C$_1$–C$_4$)-alkyl]$_2$,
  ix) —phenyl,
  x) —OH,
  xi) —OCH$_2$CH$_2$OH,
  xii) —CF$_3$;
(g) —CONHSO$_2$—(C$_1$–C$_8$)-alkyl, wherein the alkyl group is unsubstituted or substituted as defined in R$^4$(b),
(h) —CONHSO$_2$—(C$_1$–C$_4$)-perfluoroalkyl,
(i) -tetrazol-5-yl,
(j) —CONHSO$_2$-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl or quinolinyl, which is unsubstituted or substituted with one, two or three substituents selected from the group consisting of:
  i) (C$_1$–C$_4$)-alkyl,
  ii) —O—(C$_1$–C$_4$)-alkyl,
  iii) —CONR$^7$R$^{11}$,
  iv) F, Cl, Br or I,
  v) —COOR$^7$,
  vi) —NR$^7$CONR$^7$R$^{11}$, and
  vii) —NR$^7$COOR$^{11}$;
(k) —SO$_2$NHCO—aryl, wherein aryl is defined in Z(d) above,
(l) —SO$_2$NHCO—(C$_1$–C$_8$)-alkyl, wherein the alkyl group is unsubstituted or substituted as defined in R$^4$(b),
(m) —SO$_2$NHCO—(C$_1$–C$_4$)-perfluoroalkyl,
(n) —SO$_2$NHCO-heteroaryl, wherein heteroaryl is as defined in Z(g) above,
(o) —SO$_2$NHCON(R$^{11}$)$_2$ wherein the R$^{11}$ groups are the same or different,
(p) —PO(OR$^7$)$_2$, wherein the R$^7$ groups are the same or different, or
(q) —PO(R$^{11}$)OR$^7$;

R$^{13}$ is:
(a) (C$_1$–C$_4$)-alkyl,
(b) CHR$^{14}$—O—COR$^{15}$,
(c) CH$_2$CH$_2$—N[(C$_1$–C$_2$)-alkyl]$_2$,
(d) CH$_2$CH$_2$—N[CH$_2$CH$_2$]$_2$O,
(e) (CH$_2$CH$_2$O)$_y$—O—[(C$_1$–C$_4$)-alkyl], wherein y is 1 or 2,
(f) phenyl, naphthyl, CH$_2$-phenyl or CH$_2$-naphthyl, where phenyl or naphthyl is substituted or unsubstituted with CO$_2$—(C$_1$–C$_4$)-alkyl,

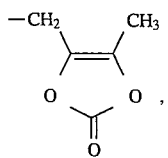 (g)

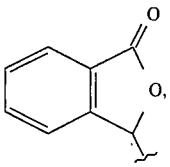 (h)

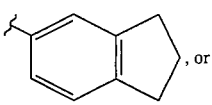 , or (i)

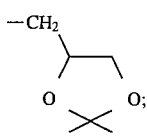 (j)

R$^{14}$ and R$^{15}$ independently are (C$_1$–C$_6$)-alkyl or phenyl; and

R$^{16}$ is a 5-membered partially or fully unsaturated heterocycle selected from the group consisting of:

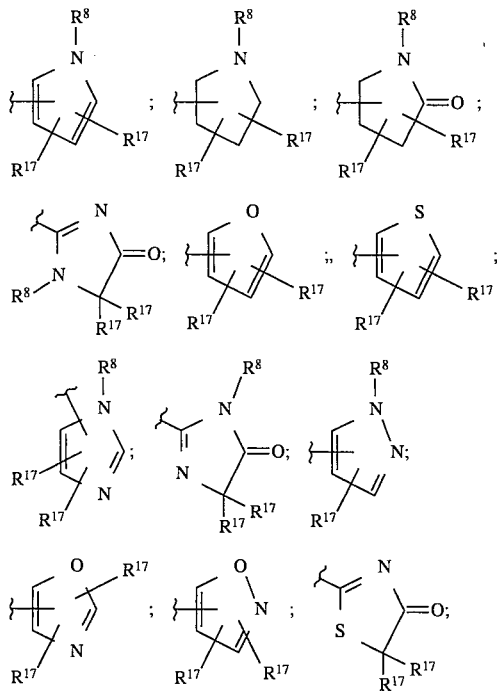

and
R¹⁷ is:
- (a) H,
- (b) (C₁–C₆)-alkyl, unsubstituted or substituted with (C₃–C₇)-cycloalkyl or —CO₂R⁷,
- (c) (C₂–C₆)-alkenyl,
- (d) (C₂–C₆)-alkynyl,
- (e) Cl, Br, F, I,
- (f) (C₁–C₆)-alkoxy,
- (g) perfluoro-(C₁–C₆)-alkyl,
- (h) (C₃–C₇)-cycloalkyl, unsubstituted or substituted with (C₁–C₆)-alkyl,
- (i) phenyl,
- (j) (C₁–C₆)-alkyl-S(O)$_n$—(CH₂)$_n$—,
- (k) hydroxy-(C₁–C₆)-alkyl,
- (l) —CN,
- (m) —CO₂R⁷,
- (n) —OH,
- (o) —NR⁷R¹¹,
- (p) —[(C₁–C₆)-alkyl]NR⁷R¹¹,
- (q) —NO₂,
- (r) —(CH₂)$_n$—SO₂—N(R⁷)₂,
- (s) —NR⁷CO—(C₁–C₄)-alkyl, or
- (t) —CON(R⁷)₂.

4. The compound of claim 2 of structural formula III:

III or a pharmaceutically acceptable salt thereof, wherein:

R¹, R², R³$^a$ and R³$^b$ are independently:
- (a) H,
- (b) F, Cl, Br, or I,
- (c) —NO₂,
- (d) (C₁–C₆)-alkyl,
- (e) —OR⁷,
- (f) —NHCO—(C₁–C₄)-alkyl,
- (g) —NHCO—O(C₁–C₄)-alkyl,
- (h) —O—(CH₂)$_m$—OR⁷,
- (i) —CONR⁷R¹¹, or
- (j) —COOR⁷;

R¹ and R² on adjacent carbon atoms can be joined together to form a ring structure:

A represents:
- a) —Y—C(R⁴)=C(R⁵)—,
- b) —Y—C(R⁴)=N—,
- c) —Y—N=C(R⁴)—,
- d) —Y—[C(R⁶)(R⁶)]$_s$—Y—,
- e) —Y—C(R⁶)(R⁶)—C(R⁶)(R⁶)—,
- f) —C(R⁴)=C(R⁵)—Y—,
- g) —N=C(R⁴)—Y—,
- h) —C(R⁶)(R⁶)—C(R⁶)(R⁶)—Y—, or
- i) —C(R⁴)=C(R⁵)—C(R⁴)=C(R⁵)—;

m is 2, 3 or 4,
n is 0, 1 or 2,
s is 1 or 2,
Y is —O—, —S— and NR⁷
R⁴ and R⁵ are independently:
- (a) H,
- (b) (C₁–C₆)-alkyl,
- (c) (C₃–C₇)-cycloalkyl,
- (d) F, Cl, Br, I,
- (e) —NR⁷COOR¹¹,
- (f) —SO₂NR⁷R¹¹,
- (g) —O—(C₁–C₄)-alkyl,
- (h) —S(O)$_n$—(C₁–C₄)-alkyl, or
- (i) —NHSO₂R¹¹;

R⁶ is:
- (a) H, or
- (b) (C₁–C₄)-alkyl, or
- (c) Cl, or F;

R⁷ is:
- (a) H,
- (b) (C₁–C₆)-alkyl,
- (c) phenyl, or
- (d) benzyl;

R⁸ is:
- (a) H,
- (b) (C₁–C₆)-alkyl, or
- (c) phenyl;

R⁹ and R¹⁰ are independently:
- (a) H,
- (b) (C₁–C₆)-alkyl, unsubstituted or substituted with (C₃–C₇)-cycloalkyl,
- (c) Cl, Br, F, I,
- (d) (C₁–C₆)-alkoxy, or
- (e) hydroxy-(C₁–C₆)-alkyl;

R¹¹ is
- (a) (C₁–C₆)-alkyl, unsubstituted or substituted with a substituent selected from the group consisting of:
  - i) —OR⁷,
  - ii) —N[R⁷]₂,
  - iii) —NH₂,
  - iv) —COOR⁷, v) —N[CH$_2$CH$_2$]$_2$Q,
vi) —CF$_3$, or
vii) —CON(R$^7$)$_2$;
(b) aryl, wherein aryl is defined as phenyl or naphthyl which is unsubstituted or substituted with one or two substituents selected from the group consisting of:
i) (C$_1$–C$_4$)-alkyl,
ii) —O—(C$_1$–C$_4$)-alkyl,
iii) —CO[NR$^7$]$_2$,
iv) F, Cl, Br or I,
v) —COOR$^7$,
vi) —NH$_2$,
vii) —NH[(C$_1$–C$_4$)-alkyl],
viii) —N[(C$_1$–C$_4$)-alkyl]$_2$,
ix) —CON[CH$_2$CH$_2$]$_2$Q, or
(c) —(C$_1$–C$_4$)-alkylaryl, wherein aryl is as defined above,
(d) (C$_3$–C$_7$)-cycloalkyl,
(e)

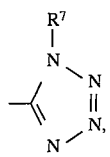

or
(f) CF$_3$;
R$^7$ and R$^{11}$ on the same nitrogen atom they can join together to form a ring selected from the group consisting of: morpholinyl, piperazinyl, or pyrrolyl, or
Q is O, or —NR$^7$;
R$^{12}$ is —CONR$^7$(CH$_2$)$_p$—E—R$^{16}$;
p is 0 to 4;
E is a single bond, NH, O, S, with the proviso that E is a single bond when p is 0 or 1;
X is
(a) —O—,
(b) —NR$^7$, or
(c) -single bond;
Z is:
(a) —CO$_2$H,
(b) —CO$_2$R$^{13}$,
(c) —CONH(tetrazol-5-yl),
(d) —CONHSO$_2$NR$^7$R$^{11}$,
(e) —CONHSO$_2$—aryl, wherein aryl is defined as phenyl or naphthyl which is unsubstituted or substituted with one, two or three substituents selected from the group consisting of:
i) (C$_1$–C$_4$)-alkyl,
ii) —O—(C$_1$–C$_4$)-alkyl,
iii) —CONR$^7$R$^{11}$,
iv) F, Cl, Br or I,
v) —COOR$^7$,
vi) —NH$_2$,
vii) —NH[(C$_1$–C$_4$)-alkyl],
viii) —N[(C$_1$–C$_4$)-alkyl]$_2$,
ix) -phenyl;
(f) —CONHSO$_2$—(C$_1$–C$_8$)-alkyl, wherein alkyl is unsubstituted or substituted as defined in R$^4$(b),
(g) —CONHSO$_2$-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl, or quinolinyl, which is unsubstituted or substituted with one, two or three substituents selected from the group consisting of:
i) (C$_1$–C$_4$)-alkyl,
ii) —O—(C$_1$–C$_4$)-alkyl,
iii) —CONR$^7$R$^{11}$,
iv) F, Cl, Br or I,
v) —COOR$^7$,
vi) —NR$^7$CONR$^7$R$^{11}$, and
vii) —NR$^7$COOR$^{11}$;
(h) -tetrazol-5-yl;
R$^{13}$ is: (C$_1$–C$_4$)-alkyl; and
R$^{16}$ is a 5-membered partially or fully unsaturated heterocycle selected from the group consisting of:

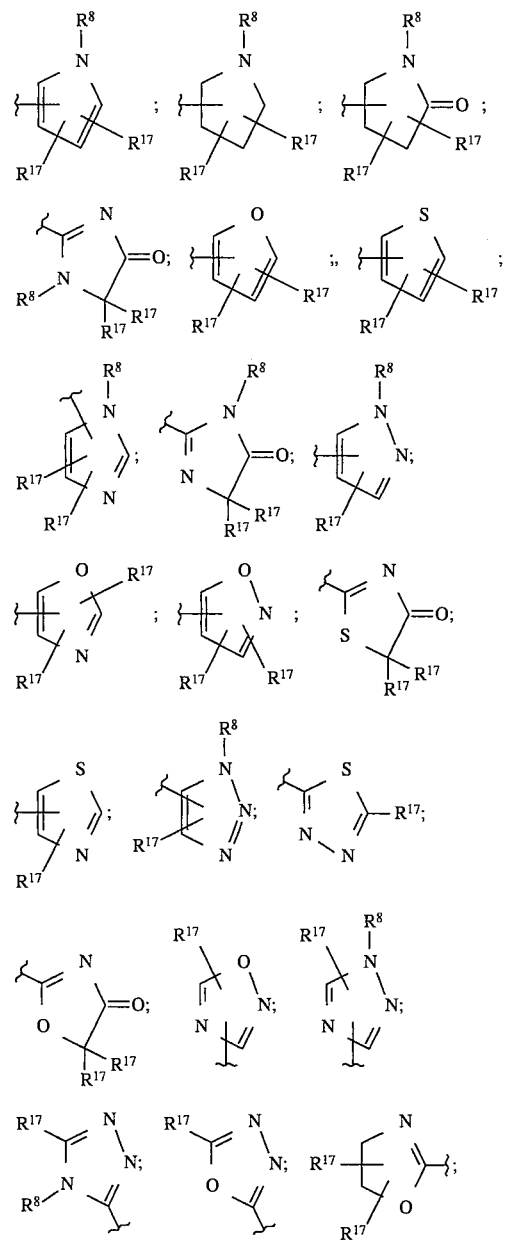

and
R$^{17}$ is:
(a) H,
(b) (C$_1$–C$_6$)-alkyl, unsubstituted or substituted with (C$_3$–C$_7$)-cycloalkyl,
(c) Cl, Br, F, I,
(d) (C$_1$–C$_6$)-alkoxy,
(e) perfluoro-(C$_1$–C$_6$)-alkyl, (f) hydroxy-$(C_1-C_6)$-alkyl,
(g) —CN,
(h) —$CO_2R^7$,
(i) —OH,
(j) —$NR^7R^{11}$,
(k) —$CON(R^7)_2$.

5. The compound of claim 2 of structural formula IV:

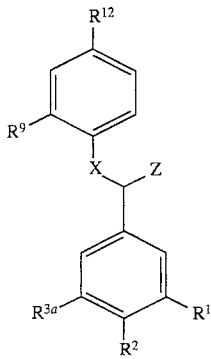

or a pharmaceutically acceptable salt thereof, wherein:
$R^1$ and $R^2$ taken together form the ring structure:

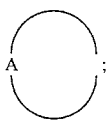

A represents:
 a) —Y—$[C(R^6)(R^6)]_s$—Y—, or
 b) —$C(R^4)$=$C(R^5)$—$C(R^4)$=$C(R^5)$—;
s is 1 or 2;
Y is —O—;
$R^{3a}$ is:
 (a) H,
 (b) F, Cl, Br, or I,
 (c) $(C_1-C_6)$-alkyl,
 (d) —$OR^7$,
 ((e) —O—$(CH_2)_m$—$OR^7$,
 (f) —$CONR^7R^{11}$, or
 (g) —$COOR^7$;
m is 2, 3 or 4;
$R^4$ and $R^5$ are independently:
 (a) H,
 (b) $(C_1-C_6)$-alkyl,
 (c) $(C_3-C_7)$-cycloalkyl,
 (d) F, Cl, Br, I,
 (e) —$NR^7COOR^{11}$,
 (f) —$SO_2NR^7R^{11}$,
 (g) —O—$(C_1-C_4)$-alkyl,
 (h) —$S(O)_n$—$(C_1-C_4)$-alkyl, or
 (i) —$NHSO_2R^{11}$;
n is 0, 1 or 2,
$R^6$ is:
 (a) H, or
 (b) $(C_1-C_4)$-alkyl, or
 (c) Cl, or F;
$R^7$ is:
 (a) H,
 (b) $(C_1-C_6)$-alkyl,
 (c) phenyl, or
 (d) benzyl;
$R^8$ is:
 (a) H,
 (b) $(C_1-C_6)$-alkyl, or
 (c) phenyl;
$R^9$ is:
 (a) H,
 (b) $(C_1-C_6)$-alkyl, unsubstituted or substituted with $(C_3-C_7)$-cycloalkyl,
 (c) Cl, Br, F, I,
 (d) $(C_1-C_6)$-alkoxy, or
 (e) hydroxy-$(C_1-C_6)$-alkyl;
$R^{11}$ is
 (a) $(C_1-C_6)$-alkyl, unsubstituted or substituted with a substituent selected from the group consisting of:
  i) —$OR^7$,
  ii) —$N[R^7]_2$,
  iii) —$NH_2$,
  iv) —$COOR^7$,
  v) —$N[CH_2CH_2]_2Q$,
  vi) —$CF_3$, or
  vii) —$CON(R^7)_2$;
 (b) aryl, wherein aryl is defined as phenyl or naphthyl which is unsubstituted or substituted with one or two substituents selected from the group consisting of:
  i) $(C_1-C_4)$-alkyl,
  ii) —O—$(C_1-C_4)$-alkyl,
  iii) —$CO[NR^7]_2$,
  iv) F, Cl, Br or I,
  v) —$COOR^7$,
  vi) —$NH_2$,
  vii) —$NH[(C_1-C_4)$-alkyl],
  viii) —$N[(C_1-C_4)$-alkyl]$_2$, or
  ix) —$CON[CH_2CH_2]_2Q$;
 (c) —$(C_1-C_4)$-alkylaryl, wherein aryl is as defined above,
 (d) $(C_3-C_7)$-cycloalkyl,
 (e)

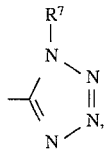

or
 (f) $CH_3$;
$R^7$ and $R^{11}$ on the same nitrogen atom they can join together to form a ring selected from the group consisting of: morpholinyl, piperazinyl, or pyrrolyl, or
Q is O, or —$NR^7$;
$R^{12}$ is —$CONR^7(CH_2)_p$—E—$R^{16}$;
p is 0 to 4;
E is a single bond, NH, O, S, with the proviso that E is a single bond when p is 0 or 1;
X is
 (a) —O—,
 (b) —$NR^7$—, or
 (c) -single bond;
Z is:
 (a) —$CO_2H$,
 (b) —$CO_2R^{13}$,
 (c) —CONH—(tetrazol-5-yl),
 (d) —$CONHSO_2NR^7R^{11}$,
 (e) —$CONHSO_2$—aryl, wherein aryl is defined as phenyl or naphthyl which is unsubstituted or substituted with one, two or three substituents selected from the group consisting of:

i) $(C_1-C_4)$-alkyl,
ii) —O—$(C_1-C_4)$-alkyl,
iii) —CONR$^7$R$^{11}$,
iv) F, Cl, Br or I,
v) —COOR$^7$,
vi) —NH$_2$,
vii) —NH[$(C_1-C_4)$-alkyl],
viii) —N[$(C_1-C_4)$-alkyl]$_2$,
ix) -phenyl;

(f) —CONHSO$_2$—$(C_1-C_8)$-alkyl, wherein alkyl is unsubstituted or substituted as defined in R$^4$(b), (g) —CONHSO$_2$-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl, or quinolinyl, which is unsubstituted or substituted with one, two, or three substituents selected from the group consisting of:
i) $(C_1-C_4)$-alkyl,
ii) —O—$(C_1-C_4)$-alkyl,
iii) —CONR$^7$R$^{11}$,
iv) F, Cl, B r or I,
v) —COOR$^7$,
vi) —NR$^7$CONR$^7$R$^{11}$, and
vii) —NR$^7$COOR$^{11}$;

(h) -tetrazol-5-yl;

R$^{13}$ is: $(C_1-C_4)$-alkyl; and

R$^{16}$ is a 5-membered partially or fully unsaturated heterocycle selected from the group consisting of:

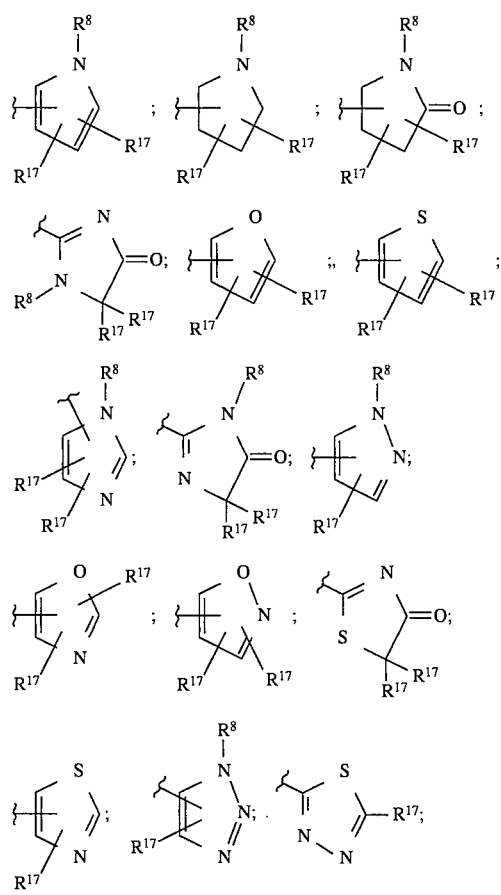

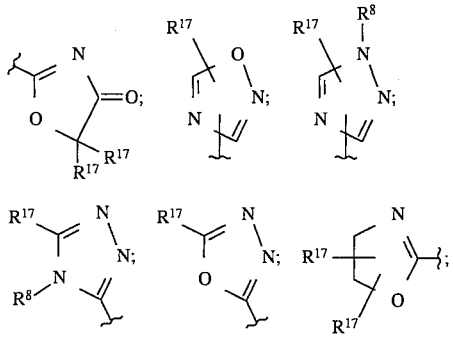

and

R$^{17}$ is:
(a) H,
(b) $(C_1-C_6)$-alkyl, unsubstituted or substituted with $(C_3-C_7)$-cycloalkyl,
(c) Cl, Br, F, I,
(d) $(C_1-C_6)$-alkoxyl,
(e) perfluoro-$(C_1-C_6)$-alkyl,
(f) hydroxy-$(C_1-C_6)$-alkyl,
(g) —CN,
(h) —CO$_2$R$^7$,
(i) —OH,
(j) —NR$^7$R$^{11}$,
(k) —CON(R$^7$)$_2$.

6. The compound of claim 5 of structural formula IV:

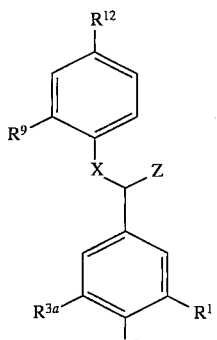

or a pharmaceutically acceptable salt thereof, wherein:

R$^1$, R$^2$, R$^{3a}$ and R$^{3b}$ are independently:
(a) H,
(b) F, Cl, Br, or I,
(c) —NO$_2$,
(d) $(C_1-C_6)$-alkyl,
(e) —OR$^7$,
(f) —NHCO—$(C_1-C_4)$-alkyl,
(g) —NHCO—O$(C_1-C_4)$-alkyl,
(h) —O—(CH$_2$)$_m$—OR$^7$,
(i) —CONR$^7$R$^{11}$, or
(j) —COOR$^7$;

m is 2, 3 or 4,

R$^4$ and R$^5$ are independently:
(a) H,
(b) $(C_1-C_6)$-alkyl,
(c) $(C_3-C_7)$-cycloalkyl,
(d) F, Cl, Br, I,
(e) —NR$^7$COOR$^{11}$,
(f) —SO$_2$NR$^7$R$^{11}$,
(g) —O—$(C_1-C_4)$-alkyl,
(h) —S(O)$_n$—$(C_1-C_4)$-alkyl, or
(i) —NHSO$_2$R$^{11}$;

n is 0, 1 or 2,

R⁶ is:
 (a) H,
 (b) $(C_1-C_4)$-alkyl, or
 (c) Cl or F;

R⁷ is:
 (a) H,
 (b) $(C_1-C_6)$-alkyl,
 (c) phenyl, or
 (d) benzyl;

R⁸ is:
 (a) H,
 (b) $(C_1-C_6)$-alkyl, or
 (c) phenyl;

R⁹ is:
 (a) H,
 (b) $(C_1-C_6)$-alkyl, unsubstituted or substituted with $(C_3-C_7)$-cycloalkyl,
 (c) Cl, Br, F, I,
 (d) $(C_1-C_6)$-alkoxy, or
 (e) hydroxy-$(C_1-C_6)$-alkyl;

R¹¹ is
 (a) $(C_1-C_6)$-alkyl, unsubstituted or substituted with a substituent selected from the group consisting of:
  i) —OR⁷,
  ii) —N[R⁷]₂,
  iii) —NH₂,
  iv) —COOR⁷,
  v) —N[CH₂CH₂]₂Q,
  vi) —CF₃, or
  vii) —CON(R⁷)₂;
 (b) aryl, wherein aryl is defined as phenyl or naphthyl which is unsubstituted or substituted with one or two substituents selected from the group consisting of:
  i) $(C_1-C_4)$-alkyl,
  ii) —O—$(C_1-C_4)$-alkyl,
  iii) —CO[NR⁷]₂,
  iv) F, Cl, Br or I,
  v) —COOR⁷,
  vi) —NH₂,
  vii) —NH[$(C_1-C_4)$-alkyl],
  viii) —N[$(C_1-C_4)$-alkyl]₂, or
  ix) —CON[CH₂CH₂]₂Q;
 (c) —$(C_1-C_4)$-alkylaryl, wherein aryl is as defined above,
 (d) $(C_3-C_7)$-cycloalkyl,
 (e)

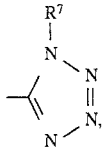

or
 (f) CF₃;

R⁷ and R¹¹ on the same nitrogen atom they can join together to form a ring selected from the group consisting of: morpholinyl, piperazinyl, or pyrrolyl, or Q is O, or —NR⁷;

R¹² is —CONR⁷ (CH₂)ₚ—E—R¹⁶;

p is 0 to 4;

E is a single bond, NH, O, S, with the proviso that E is a single bond when p is 0 or 1;

X is (a) —O—,
 (b) —NR⁷—, or
 (c) -single bond;

Z is:
 (a) —CO₂H,
 (b) —CO₂R¹³,
 (c) —CONH-(tetrazol-5-yl),
 (d) —CONHSO₂NR⁷R¹¹,
 (e) —CONHSO₂-aryl, wherein aryl is defined as phenyl or naphthyl which is unsubstituted or substituted with one, two or three substituents selected from the group consisting of:
  i) $(C_1-C_4)$-alkyl,
  ii) —O—$(C_1-C_4)$-alkyl,
  iii) —CONR⁷R¹¹,
  iv) F, Cl, Br or I,
  v) —COOR⁷,
  vi) —NH₂,
  vii) —NH[$(C_1-C_4)$-alkyl],
  viii) —N[$(C_1-C_4)$-alkyl]₂,
  ix) -phenyl;
 (f) —CONHSO₂—$(C_1-C_8)$-alkyl, wherein alkyl is unsubstituted or substituted as defined in R⁴(b),
 (g) —CONHSO₂-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl, or quinolinyl, which is unsubstituted or substituted with one, two or three substituents selected from the group consisting of:
  i) $(C_1-C_4)$-alkyl,
  ii) —O—$(C_1-C_4)$-alkyl,
  iii) —CONR⁷R¹¹,
  iv) F, Cl, Br or I,
  v) —COOR⁷,
  vi) —NR⁷CONR⁷R¹¹, and
  vii) —NR⁷COOR¹¹;
 (h) -tetrazol-5-yl;

R¹³ is: $(C_1-C_4)$-alkyl; and

R¹⁶ is a 5-membered partially or fully unsaturated heterocycle selected from the group consisting of:

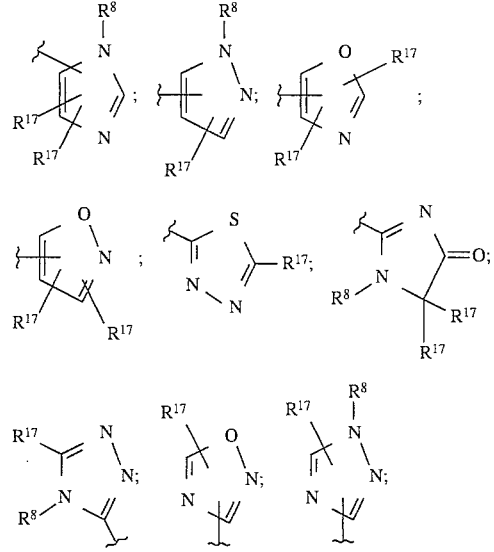

R¹⁷ is:
 (a) H,
 (b) $(C_1-C_6)$-alkyl, unsubstituted or substituted with $(C_3-C_7)$-cycloalkyl, (c) Cl, Br, F, I,
(d) $(C_1-C_6)$-alkoxy,
(e) perfluoro-$(C_1-C_6)$-alkyl,
(f) hydroxy-$(C_1-C_6)$-alkyl,
(g) —CN,
(h) —$CO_2R^7$,
(i) —OH,
(j) —$NR^7R^{11}$,
(k) —$CON(R^7)_2$.

7. The compound of claim 2 of structural formula V:

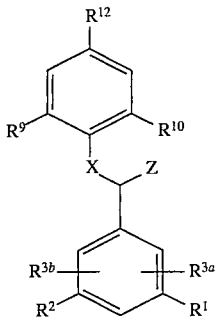

V or a pharmaceutically acceptable salt thereof, wherein:
$R^1$, $R^2$, $R^{3a}$ and $R^{3b}$ are independently:
(a) H,
(b) F, Cl, Br, or I,
(c) —$NO_2$,
(d) $(C_1-C_6)$-alkyl,
(e) —$OR^7$,
(f) —NHCO—$(C_1-C_4)$-alkyl,
(g) —NHCO—$O(C_1-C_4)$-alkyl,
(h) —O—$(CH_2)_m$—$OR^7$,
(i) —$CONR^7R^{11}$, or
(j) —$COOR^7$;

m is 2, 3 or 4,
$R^4$ and $R^5$ are independently:
(a) H,
(b) $(C_1-C_6)$-alkyl,
(c) $(C_3-C_7)$-cycloalkyl,
(d) F, Cl, Br, I,
(e) —$NR^7COOR^{11}$,
(f) —$SO_2NR^7R^{11}$,
(g) —O—$(C_1-C_4)$-alkyl,
(h) —$S(O)_n$—$(C_1-C_4)$-alkyl, or
(i) —$NHSO_2R^{11}$;

n is 0, 1 or 2,
$R^6$ is:
(a) H,
(b) $(C_1-C_4)$-alkyl, or
(c) Cl or F;

$R^7$ is:
(a) H,
(b) $(C_1-C_6)$-alkyl,
(c) phenyl, or
(d) benzyl;

$R^8$ is:
(a) H,
(b) $(C_1-C_6)$-alkyl, or
(c) phenyl;

$R^9$ and $R^{10}$ are independently:
(a) H,
(b) $(C_1-C_6)$-alkyl, unsubstituted or substituted with $(C_3-C_7)$-cycloalkyl,
(c) Cl, Br, F, I,
(d) $(C_1-C_6)$-alkoxy, or
(e) hydroxy-$(C_1-C_6)$-alkyl;

$R^{11}$ is
(a) $(C_1-C_6)$-alkyl, unsubstituted or substituted with a substituent selected from the group consisting of:
   i) —$OR^7$,
   ii) —$N[R^7]_2$,
   iii) —$NH_2$,
   iv) —$COOR^7$,
   v) —$N[CH_2CH_2]_2Q$,
   vi) —$CF_3$, or
   vii) —$CON(R^7)_2$;
(b) aryl, wherein aryl is defined as phenyl or naphthyl which is unsubstituted or substituted with one or two substituents selected from the group consisting of:
   i) $(C_1-C_4)$-alkyl,
   ii) —O—$(C_1-C_4)$-alkyl,
   iii) —$CO[NR^7]_2$,
   iv) F, Cl, B r or I,
   v) —$COOR^7$,
   vi) —$NH_2$,
   vii) —$NH[(C_1-C_4)$-alkyl],
   viii) —$N[(C_1-C_4)$-alkyl]$_2$, or
   ix) —$CON[CH_2CH_2]_2Q$;
(c) —$(C_1-C_4)$-alkylaryl, wherein aryl is as defined above,
(d) $(C_3-C_7)$-cycloalkyl,
(e)

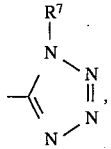

or
(f) $CF_3$;

$R^7$ and $R^{11}$ on the same nitrogen atom they can join together to form a ring selected from the group consisting of: morpholinyl, piperazinyl, or pyrrolyl, or Q is O, or —$NR^7$;
$R^{12}$ is —$CONR^7(CH_2)_p$—E—$R^{16}$;
p is 0 to 4;
E is a single bond, NH, O, S, with the proviso that E is a single bond when p is 0 or 1;
X is
(a) —O—,
(b) —$NR^7$—, or
(c) -single bond;

Z is:
(a) —$CO_2H$,
(b) —$CO_2R^{13}$,
(c) —CONH—(tetrazol-5-yl),
(d) —$CONHSO_2NR^7R^{11}$,
(e) —$CONHSO_2$—aryl, wherein aryl is defined as phenyl or naphthyl which is unsubstituted or substituted with one, two or three substituents selected from the group consisting of:
   i) $(C_1-C_4)$-alkyl,
   ii) —O—$(C_1-C_4)$-alkyl,
   iii) —$CONR^7R^{11}$,
   iv) F, Cl, B r or I,
   v) —$COOR^7$,
   vi) —$NH_2$,
   vii) —$NH[(C_1-C_4)$-alkyl],
   viii) —$N[(C_1-C_4)$-alkyl]$_2$, ix) -phenyl;

(f) —CONHSO$_2$—(C$_1$–C$_8$)-alkyl, wherein alkyl is unsubstituted or substituted as defined in R$^4$(b), (g) —CONHSO$_2$-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl, or quinolinyl, which is unsubstituted or substituted with one, two or three substituents selected from the group consisting of:
  i) (C$_1$–C$_4$)-alkyl,
  ii) —O—(C$_1$–C$_4$)-alkyl,
  iii) —CONR$^7$R$^{11}$,
  iv) F, Cl, Br or I,
  v) —COOR$^7$,
  vi) —NR$^7$CONR$^7$R$^{11}$, and
  vii) —NR$^7$COOR$^{11}$;

(h) -tetrazol-5-yl;

R$^{13}$ is: (C$_1$–C$_4$)-alkyl; and

R$^{16}$ is a 5-membered partially or fully unsaturated heterocycle selected from the group consisting of:

[structures]

and

R$^{17}$ is:
(a) H, (b) (C$_1$–C$_6$)-alkyl, unsubstituted or substituted with
(C$_3$–C$_7$)-cycloalkyl,
(c) Cl, Br, F, I,
(d) (C$_1$–C$_6$)-alkoxy,
(e) perfluoro-(C$_1$–C$_6$)-alkyl,
(f) hydroxy-(C$_1$–C$_6$)-alkyl,
(g) —CN,
(h) —CO$_2$R$^7$,
(i) —OH,
(j) —NR$^7$R$^{11}$,
(k) —CON(R$^7$)$_2$.

8. The compound of claim 2 of structural formula VI:

[structure VI]

or a pharmaceutically acceptable salt thereof, wherein:

R$^1$ and R$^2$ are represented by the following ring structure:

[ring structure A]

A represents:
  a) —Y—[C(R$^6$)(R$^6$)]$_s$—Y—, or
  b) —C(R$^4$)=C(R$^5$)=C(R$^4$)=C(R$^5$)—;

s is 1 or 2,

Y is —O—, —S— and NR$^7$;

R$^{3a}$ and R$^{3b}$ are independently:
  (a) H,
  (b) F, Cl, Br, or I,
  (c) —NO$_2$,
  (d) (C$_1$–C$_6$)-alkyl,
  (e) —OR$^7$,
  (f) —NHCO—(C$_1$–C$_4$)-alkyl,
  (g) —NHCO—O(C$_1$–C$_4$)-alkyl,
  (h) —O—(CH$_2$)$_m$—OR$^7$,
  (i) —CONR$^7$R$^{11}$, or
  (j) —COOR$^7$;

m is 2, 3 or 4,

R$^4$ and R$^5$ are independently:
  (a) H,
  (b) (C$_1$–C$_6$)-alkyl,
  (c) (C$_3$–C$_7$)-cycloalkyl,
  (d) F, Cl, Br, I, (e) —NR⁷COOR¹¹,
(f) —SO₂NR⁷R¹¹,
(g) —O—(C₁–C₄)-alkyl,
(h) —S(O)ₙ—(C₁–C₄)-alkyl, or
(i) —NHSO₂R¹¹;

n is 0, 1 or 2,

R⁶ is:
(a) H, or
(b) (C₁–C₄)-alkyl, or
(c) C or F;

R⁷ is:
(a) H,
(b) (C₁–C₆)-alkyl,
(c) phenyl, or
(d) benzyl;

R⁸ is:
(a) H,
(b) (C₁–C₆)-alkyl, or
(c) phenyl;

R⁹ and R¹⁰ are independently:
(a) H,
(b) (C₁–C₆)-alkyl, unsubstituted or substituted with (C₃–C₇)-cycloalkyl,
(c) Cl, Br, F, I,
(d) (C₁–C₆)-alkoxy, or
(e) hydroxy-(C₁–C₆)-alkyl;

R¹¹ is
(a) (C₁–C₆)-alkyl, unsubstituted or substituted with a substituent selected from the group consisting of:
 i) —OR⁷,
 ii) —N[R⁷]₂,
 iii) —NH₂,
 iv) —COOR⁷,
 v) —N[CH₂CH₂]₂Q,
 vi) —CF₃, or
 vii) —CON(R⁷)₂;
(b) aryl, wherein aryl is defined as phenyl or naphthyl which is unsubstituted or substituted with one or two substituents selected from the group consisting of:
 i) (C₁–C₄)-alkyl,
 ii) —O—(C₁–C₄)-alkyl,
 iii) —CO[NR⁷]₂,
 iv) F, Cl, Br or I,
 v) —COOR⁷,
 vi) —NH₂,
 vii) —NH[(C₁–C₄)-alkyl],
 viii) —N[(C₁–C₄)-alkyl]₂, or
 ix) —CON[CH₂CH₂]₂Q;
(c) —(C₁–C₄)-alkylaryl, wherein aryl is as defined above,
(d) (C₃–C₇)-cycloalkyl,
(e)

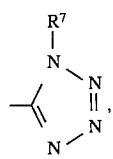

or
(f) CF₃;

R⁷ and R¹¹ on the same nitrogen atom they can join together to form a ring selected from the group consisting of: morpholinyl, piperazinyl, or pyrrolyl, or Q is O, or —NR⁷;

R¹² is —CONR⁷(CH₂)ₚ—E—R¹⁶;

p is 0 to 4;

E is a single bond, NH, O, S, with the proviso that E is a single bond when p is 0 or 1;

X is
(a) —O—,
(b) —NR⁷—, or
(c) -single bond;

Z is:
(a) —CO₂H,
(b) —CO₂R¹³,
(c) —CO NH-(tetrazazol-5-yl),
(d) —CONHSO₂NR⁷R¹¹,
(e) —CONHSO₂—aryl, wherein aryl is defined as phenyl or naphthyl which is unsubstituted or substituted with one, two or three substituents selected from the group consisting of:
 i) (C₁–C₄)-alkyl,
 ii) —O—(C₁–C₄)-alkyl,
 iii) —CONR⁷R¹¹,
 iv) F, Cl, Br or I,
 v) —COOR⁷,
 vi) —NH₂,
 vii) —NH[(C₁–C₄)-alkyl],
 viii) —N[(C₁–C₄)-alkyl]₂,
 ix) -phenyl;
(f) —CONHSO₂—(C₁–C₈)-alkyl, wherein alkyl is unsubstituted or substituted as defined in R⁴(b),
(g) —CONHSO₂-heteroaryl, wherein heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl, or quinolinyl, which is unsubstituted or substituted with one, two or three substituents selected from the group consisting of:
 i) (C₁–C₄)-alkyl,
 ii) —O—(C₁–C₄)-alkyl,
 iii) —CONR⁷R¹¹,
 iv) F, Cl, Br or I,
 v) —COOR⁷,
 vi) —NR⁷CONR⁷R¹¹, and
 vii) —NR⁷COOR¹¹;
(h) -tetrazol-5-yl;

R¹³ is: (C₁–C₄)-alkyl; and

R¹⁶ is a 5-membered partially or fully unsaturated heterocycle selected from the group consisting of:

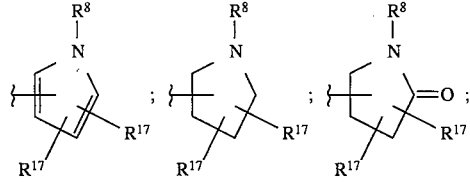

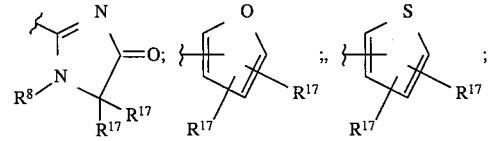

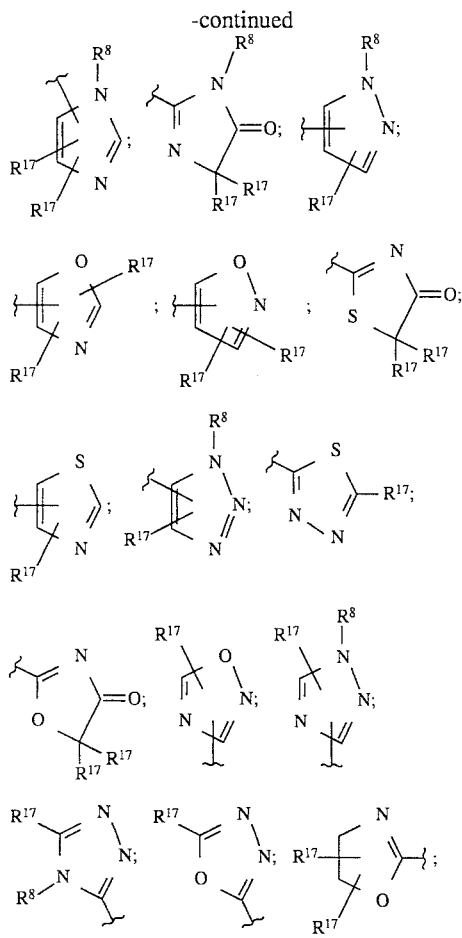

and
R$^{17}$ is:
(a) H,
(b) (C$_1$–C$_6$)-alkyl, unsubstituted or substituted with (C$_3$–C$_7$)-cycloalkyl or —CO$_2$R$^7$,
(c) (C$_2$–C$_6$)-alkenyl,
(d) (C$_2$–C$_6$)-alkynyl,
(e) Cl, Br, F, I,
(f) (C$_1$–C$_6$)-alkoxy,
(g) perfluoro-(C$_1$–C$_6$)-alkyl,
(h) (C$_3$–C$_7$)-cycloalkyl, unsubstituted or substituted with (C$_1$–C$_6$)-alkyl,
(i) phenyl,
(j) (C$_1$–C$_6$)-alkyl—S(O)$_n$—(CH$_2$)$_n$—,
(k) hydroxy-(C$_1$–C$_6$)-alkyl,
(l) —CN,
(m) —CO$_2$$^{R7}$,
(n) —OH,
(o) —NR$^7$R$^{11}$,
(p) —[(C$_1$–C$_6$)-alkyl]NR$^7$R$^{11}$,
(q) —NO$_2$,
(r) —(CH$_2$)$_n$—SO$_2$—N(R$^7$)$_2$,
(s) —NR$^7$CO—(C$_1$–C$_4$)-alkyl, or
(t) —CON(R$^7$)$_2$.

9. A compound which is selected from the group consisting of:

N-(4-isopropylbenzenesulfonyl)-α-[2-n-propyl-4-[[(1,2,4-triazol-3-yl)amino]carbonyl]phenoxy]-3,4-(methylenedioxy)phenylacetamide;

N-(4-isopropylbenzenesulfonyl)-α-[2-n-propyl-4-[[(thiazol-2-yl)amino]carbonyl]phenoxy]-3,4-(methylenedioxy)phenylacetamide;

N-(4-isopropylbenzenesulfonyl)-α-[2-n-propyl-4-[[(1,3,4-thiadiazol-2-yl)-amino]carbonyl]phenoxy]-3,4-(methylenedioxy)phenylacetamide;

N-(4-isopropylbenzenesulfonyl)-α-[2-n-propyl-4-[[(4,5-dimethyl-oxazol-2-yl)amino]carbonyl]phenoxy]-3,4-(methylenedioxy)phenylacetamide;

N-(4-isopropylbenzenesulfonyl)-α-[2-n-propyl-4-[[(4,5-dihydro-1-methyl-4-oxo-1H-imidazol-2-yl)amino]carbonyl]phenoxy]-3,4(methylenedioxy)phenylacetamide;

N-(4-isopropylbenzenesulfonyl)-α-[2-n-propyl-4-[[(1-methyl-1H-imidazol-2-yl)amino]carbonyl]phenoxy]-3,4-(methylenedioxy)phenylacetamide;

N-(4-isopropylbenzenesulfonyl)-α-[2-n-propyl-4-[[(4,5-dihydro-4-oxothiazol-2-yl)amino]carbonyl]phenoxy]-3,4-(methylenedioxy)phenylacetamide;

N-(4-isopropylbenzenesulfonyl)-α-[2-n-propyl-4-[[[(2-furyl)methyl]amino]carbonyl]phenoxy]-3,4-(methylenedioxy)phenylacetamide;

N-(4-isopropylbenzenesulfonyl)-α-[2-n-propyl-4-[[(5-methylisoxazol-3-yl)amino]carbonyl]phenoxy]-3,4-(methylenedioxy)phenylacetamide;

N-(4-isopropylbenzenesulfonyl)-α-[2-n-propyl-4-[[(5-methyl-1H-pyrazol-3-yl)amino]carbonyl]phenoxy]-3,4-(methylenedioxy)phenylacetamide;

N-(4-isopropylbenzenesulfonyl)-α-[2-n-propyl-4-[[(1-methyl-1H-pyrazol-5-yl)amino]carbonyl]phenoxy]-3,4-(methylenedioxy)phenylacetamide;

N-(4-isopropylbenzenesulfonyl)-α-[2-n-propyl-4-[[(4-cyano-1H-pyrazol-3-yl)amino]carbonyl]phenoxy]-3,4-(methylenedioxy)phenylacetamide;

N-(4-isopropylbenzenesulfonyl)-α-[2-n-propyl-4-[[(Δ$^2$-oxazolin-2yl)amino]carbonyl]phenoxy]-3,4-(methylenedioxy)-phenylacetamide;

N-(4-isopropylbenzenesulfonyl)-α-[2-n-propyl-4-[[[(2-thienyl)methyl]amino]carbonyl]phenoxy]-3,4-(methylenedioxy)phenylacetamide;

N-(4-isopropylbenzenesulfonyl)-α-[2-n-propyl-4-[[(4,5-dicyanoimidazol-2-yl)amino]carbonyl]phenoxy]-3,4-(methylenedioxy)phenylacetamide;

N-(4-isopropylbenzenesulfonyl)-α-[2-n-propyl-4-[[(5-methyl-1,2,4-triazol-3-yl)amino]carbonyl]phenoxy]-3,4-(methylenedioxy)phenylacetamide;

N-(4-isopropylbenzenesulfonyl)-α-[2-n-propyl-4-[[(1-methyl-1H-1,2,4-triazol-3-yl)amino]carbonyl]phenoxy]-3,4-(methylenedioxy)phenylacetamide;

N-(4-isopropylbenzenesulfonyl)-α-[2-n-propyl-4-[[(4-methyl-4-H-1,2,4-triazol-3-yl)amino]carbonyl]phenoxy]-3,4-(methylenedioxy)phenylacetamide;

N-(4-isopropylbenzenesulfonyl)-α-[2-n-propyl-4-[[(5trifluoromethyl-4-H-1,2,4-triazol-3-yl)amino]carbonyl]phenoxy]3,4-(methylenedioxy)phenylacetamide;

N-(4-isopropylbenzenesulfonyl)-α-[2-n-propyl-4-[[(imidazol-2-yl)amino]carbonyl]phenoxy]-3,4-(methylenedioxy)phenylacetamide;

N-(4-isopropylbenzenesulfonyl)-α-[2-n-propyl-4-[[[(imidazol-2-yl)methyl]amino]carbonyl]phenoxy]-3,4-(methylenedioxy)phenylacetamide;

N-(4-isopropylbenzenesulfonyl)-α-[2-n-propyl-4-[[(4-(amonocarbonyl)-1,2,3-triazol-5-yl)amino]carbonyl]phenoxy]-3,4-(methylenedioxy)phenylacetamide;

N-(4-isopropylbenzenesulfonyl)-α-[2-n-propyl-4-[[(4,5-dihydro-4-oxo-1H-imidazol-2-yl)amino]carbonyl]phenoxy]-3,4(methylenedioxy)phenylacetamide;

N-(4-isopropylbenzenesulfonyl)-α-[2-n-propyl-4-[[[(1-ethyl-pyrrolidin-2-yl)methyl]amino]carbonyl]phenoxy]-3,4(methylenedioxy)phenylacetamide;

N-(4-isopropylbenzenesulfonyl)-α-[2-n-propyl-4-[[[-(1,2,4,-oxadiazol-3-yl)methyl]amino]carbonyl]phenoxy]-3,4-(methylenedioxy)phenylacetamide.

10. A compound which is selected from the group consisting of:

N-(4-isopropylbenzenesulfonyl)-α-[2-n-propyl-4-[[(1,2,4-triazol-3-yl)amino]carbonyl]phenoxy]-3,4-(methylenedioxy)phenylacetamide;

N-(4-isopropylbenzenesulfonyl)-α-[2-n-propyl-4-[[(thiazol-2-yl)-amino]carbonyl]phenoxy]-3,4-(methylenedioxy)phenylacetamide;

N-(4-isopropylbenzenesulfonyl)-α-[2-n-propyl-4-[[(1,3,4-thiadiazol-2-yl)-amino]carbonyl]phenoxy]-3,4-(methylenedioxy)phenylacetamide;

N-(4-isopropylbenzenesulfonyl)-α-[2-n-propyl-4-[[(4,5-dimethyloxazol-2-yl)amino]carbonyl]phenoxy]-3,4-(methylenedioxy)phenylacetamide;

N-(4-isopropylbenzenesulfonyl)-α-[2-n-propyl-4-[[(4,5-dihydro-1-methyl-4-oxo-1H-imidazol-2-yl)amino]carbonyl]phenoxy]-3,4(methylenedioxy)phenylacetamide;

N-(4-isopropylbenzenesulfonyl)-α-[2-n-propyl-4-[[(1-methyl-1H-imidazol-2-yl)amino]carbonyl]phenoxy]-3,4-(methylenedioxy)phenylacetamide;

N-(4-isopropylbenzenesulfonyl)-α-[2-n-propyl-4-[[(4,5-dihydro-4-oxothiazol-2-yl)amino]carbonyl]phenoxy]-3,4-(methylenedioxy)phenylacetamide;

N-(4-isopropylbenzenesulfonyl)-α-[2-n-propyl-4-[[[(2-furyl)methyl]amino]carbonyl]phenoxy]-3,4-(methylenedioxy)phenylacetamide;

N-(4-isopropylbenzenesulfonyl)-α-[2-n-propyl-4-[[(5-methylisoxazol-3-yl)amino]carbonyl]phenoxy]-3,4-(methylenedioxy)phenylacetamide;

N-(4-isopropylbenzenesulfonyl)-α-[2-n-propyl-4-[[(5-methyl-1H-pyrazol-3-yl)amino]carbonyl]phenoxy]-3,4-(methylenedioxy)phenylacetamide;

N-(4-isopropylbenzenesulfonyl)-α-[2-n-propyl-4-[[(1-methyl-1H-pyrazol-5-yl)amino]carbonyl]phenoxy]-3,4-(methylenedioxy)phenylacetamide;

N-(4-isopropylbenzenesulfonyl)-α-[2-n-propyl-4-[[[(2-thienyl)methyl]amino]carbonyl]phenoxy]-3,4-(methylenedioxy)phenylacetamide;

N-(4-isopropylbenzenesulfonyl)-α-[2-n-propyl-4-[[(1-methyl-1-H-2,4-triazol-3-yl)amino]carbonyl]phenoxy]-3,4-(methylenedioxy)phenylacetamide;

N-(4-isopropylbenzenesulfonyl)-α-[2-n-propyl4-[[[(imidazol-2-yl)methyl]amino]carbonyl]phenoxy]-3,4-(methylenedioxy)phenylacetamide;

N-(4-isopropylbenzenesulfonyl)-α-[2-n-propyl-4-[[(4-(aminocarbonyl)-1,2,3-triazol-5-yl)amino]carbonyl]phenoxy]-3,4(methylenedioxy)phenylacetamide;

N-(4-isopropylbenzenesulfonyl)-α-[2-n-propyl-4-[[(4,5-dihydro-4-oxo-1H-imidazol-2-yl)amino]carbonyl]phenoxy]-3,4-(methylenedioxy)phenylacetamide;

N-(4-isopropylbenzenesulfonyl)-α-[2-n-propyl-4-[[[(1-ethyl-pyrrolidin-2-yl)methyl]amino]carbonyl]phenoxy]-3,4-(methylenedioxy)phenylacetamide;

N-(4-isopropylbenzenesulfonyl)-α-[2-n-propyl-4-[[[(1,2,4-oxadiazol-3-yl)methyl]amino]carbonyl]phenoxy]-3,4-(methylenedioxy)phenylacetamide.

11. A method of treating a condition in a mammal, the treatment of which is effected or facilitated by a decrease in endothelin mediated actions, comprising the administration, in an amount that is effective for antagonizing the effect of endothelin, of a compound of Formula I as recited in claim 1.

12. The method as recited in claim 11, wherein the condition is selected from the group consisting of: hypertension, pulmonary hypertension, Raynaud's disease, myocardial infarction, angina pectoris, congestive heart failure, acute renal failure, cerebral infarction, cerebral vasospasm, arteriosclerosis, vascular restenosis, asthma, benign prostatic hyperplasia, inflammatory bowel diseases, endotoxic shock, endotoxin-induced multiple organ failure or disseminated intravascular coagulation, or cyclosporin-induced renal failure or hypertension.

13. The method as recited in claim 12, wherein the condition is hypertension.

14. The method as recited in claim 13, wherein the mammal is human.

15. The method as recited in claim 12, wherein the condition is benign prostatic hyperplasia.

16. The method as recited in claim 15, wherein the mammal is human.

17. A method of treating cardiovascular disorders by administering to a person in need of such treatment a therapeutically effective amount of a compound of Formula I as recited in claim 1.

18. A method of treating benign prostatic hyperplasia by administering to a person in need of such treatment a therapeutically effective amount of an endothelin receptor antagonist as recited in claim 1.

19. The method as recited in claim 18, wherein the endothelin receptor antagonist is an endothelin-1 selective antagonist.

20. The method as recited in claim 11 comprising a pharmaceutical composition of therapeutically effective amount of the compound of formula I and a pharmaceutically acceptable carrier.

21. A pharmaceutical composition useful in the treatment of hypertension which comprises a pharmaceutically acceptable carrier and a pharmaceutically effective amount of a compound of claim 1.

22. The composition of claim 21 which includes another antihypertensive agent selected from: $A_2$-adrenosine receptor agonists, α-adrenergic antagonists, angiotensin II antagonists, angiotensin converting enzyme inhibitors, β-adrenergic antagonists, atriopeptidase inhibitors(alone or with ANP), calcium channel blockers, diuretics, potassium channel agonists, renin inhibitors, sertonin antagonists, sympatholytic agents, and other antihypertensive agents, which are members selected from the group consisting of:

A-69729, FK 906, FK 744, UK-73900, CSG 22492C, amiloride, atenolol, atriopeptin, bendroflumethiazide, chlorothalidone, chlorothiazide, clonidine, cromakalin, cryptenamine acetates and cryptenamine tannates, deserpidine, diazoxide, doxazosin, guanabenz, guanethidine, guanethidine sulfate, hydralazine hydrochloride, hydrochlorothiazide, isradipine, ketanserin, losartan, metolazone, metoprolol, metoprolol tartate, methyclothiazide, methyldopa, methyldopate hydrochloride, minoxidil, nadolol, pargyline hydrochloride, pinacidil, pindolol, polythiazide, prazosin, propranolol, *rauwolfia serpentina*, rescinnamine, reserpine, sodium nitroprusside, spironolactone, terazosin, timolol maleate, trichlormethiazide, trimethophan camsylate, verapamil, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril, quinapril hydrochloride, ramapril, teprotide, zofenopril, zofenopril calcium, diflusinal, diltiazem, felodipine, nicardipine, nifedipine, niludipine, nimodipine, nisoldipine, nitrendipine.

\* \* \* \* \*

UNITED STATES PATENT AND TRADEMARK OFFICE
CERTIFICATE OF CORRECTION

PATENT NO. : 5,538,991                            Page 1 of 3

DATED : July 23, 1996

INVENTOR(S) : Wallace T. Ashton, Linda L. Chang and William J. Greenlee

It is certified that error appears in the above-indentified patent and that said Letters Patent is hereby corrected as shown below:

In Column 86, In Claim 3, line 2 should read as follows:
-- (l) -CN, --

In Column 86, In Claim 3, line 15 delete p1.

In Column 86, In Claim 3, after line 15 insert on a new line:
-- $R^{11}$ is . --

In Column 87, In Claim 3, line 61 should read as follows:
-- (d) $CH_2CH_2$-$N[CH_2CH_2]_2O$, --

In Column 96, In Claim 5, line 22, should read as follows:
-- (d) $(C_1-C_6)$-alkoxy, --

In Column 103, In Claim 8, line 67, should read as follows:
-- Q is O, S or -$NR^7$; --

In Column 104, In Claim 8, line 14, should read as follows:
-- (c) -CONH-(tetrazol-5-yl), --

UNITED STATES PATENT AND TRADEMARK OFFICE
CERTIFICATE OF CORRECTION

PATENT NO. : 5,538,991
DATED : July 23, 1996
INVENTOR(S) : Wallace T. Ashton, Linda L. Chang and William J. Greenlee It is certified that error appears in the above-indentified patent and that said Letters Patent is hereby corrected as shown below:

In Column 82, in Claim 2, at lines 25-30, please delete the structures and replace them with the following:

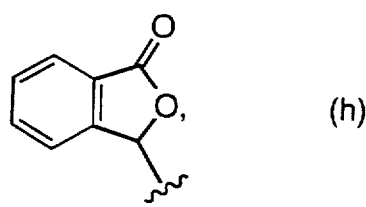  (h)

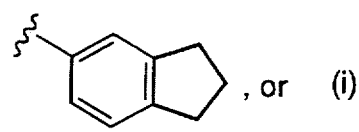 , or  (i)

In Column 82, in Claim 2, at lines 60-65, delete the structure on the left and insert:

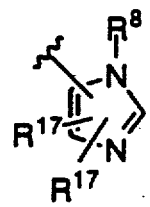

UNITED STATES PATENT AND TRADEMARK OFFICE
CERTIFICATE OF CORRECTION

PATENT NO. : 5,538,991　　　　　　　　　　　　Page 3 of 3
DATED      : July 23, 1996
INVENTOR(S): Wallace T. Ashton, Linda L. Change and William J. Greenlee It is certified that error appears in the above-indentified patent and that said Letters Patent is hereby corrected as shown below:

In Column 105, In Claim 8, line 52, should read as follows:
-- (m) -CO$_2$R$^7$, --

Signed and Sealed this

Twenty-first Day of January, 1997

Attest:

BRUCE LEHMAN

Attesting Officer　　　　Commissioner of Patents and Trademarks